United States Patent
Glover et al.

(10) Patent No.: US 12,402,797 B2
(45) Date of Patent: *Sep. 2, 2025

(54) MULTI-SENSOR CATHETER FOR RIGHT HEART AND PULMONARY ARTERY CATHETERIZATION

(71) Applicant: HemoCath Ltd., Toronto (CA)

(72) Inventors: Christopher Glover, Toronto (CA); Eric Caron, Toronto (CA); Des Regan, Taylors Hill (IE); Sylvain Abel, Shawinigan (CA)

(73) Assignee: HemoCath Ltd.

( * ) Notice: Subject to any disclaimer, the term of this patent is extended or adjusted under 35 U.S.C. 154(b) by 442 days.

This patent is subject to a terminal disclaimer.

(21) Appl. No.: 17/765,057

(22) PCT Filed: Sep. 29, 2020

(86) PCT No.: PCT/CA2020/051294
§ 371 (c)(1),
(2) Date: Mar. 30, 2022

(87) PCT Pub. No.: WO2021/062527
PCT Pub. Date: Apr. 8, 2021

(65) Prior Publication Data
US 2022/0338745 A1    Oct. 27, 2022

Related U.S. Application Data

(63) Continuation of application No. 16/587,815, filed on Sep. 30, 2019, now Pat. No. 11,272,847.

(51) Int. Cl.
*A61B 5/0205*    (2006.01)
*A61B 5/00*      (2006.01)
(Continued)

(52) U.S. Cl.
CPC ........ *A61B 5/0205* (2013.01); *A61B 5/14552* (2013.01); *A61B 5/6853* (2013.01);
(Continued)

(58) Field of Classification Search
CPC . A61B 5/0205; A61B 5/14552; A61B 5/6853; A61B 5/02154; A61B 5/02158;
(Continued)

(56) References Cited

U.S. PATENT DOCUMENTS

| | | |
|---|---|---|
| 4,543,961 A | 10/1985 | Brown |
| 4,621,929 A | 11/1986 | Philips |

(Continued)

FOREIGN PATENT DOCUMENTS

| | | |
|---|---|---|
| CN | 102202562 A | 9/2011 |
| EP | 1105181 A1 | 6/2001 |

(Continued)

OTHER PUBLICATIONS

Jeremy Fernando, "Pulmonary Artery Catheters", updated Dec. 22, 2014 (http://lifeinthefastlane.com/ccc/pulmonary-artery-catheters/); pp. 1-7.

(Continued)

*Primary Examiner* — Gary Jackson
*Assistant Examiner* — Sebastian X Lukjan
(74) *Attorney, Agent, or Firm* — Miltons IP/p.i.

(57) ABSTRACT

A system comprising a multi-sensor catheter for monitoring a cardiac hemodynamic condition, e.g. heart failure. The multi-sensor catheter comprises multi-lumen catheter tubing, first and second optical pressure sensors, and respective optical fibers and connectors. For right heart and pulmonary artery catheterization, a flow-directed multi-sensor catheter comprises a guidewire lumen, inflatable balloon tip, and sensor locations are configured for placement of a sensor in each of the right atrium and pulmonary artery, for measure- (Continued)

ment of central venous pressure in the right atrium and a pulmonary artery pressure. An optical fiber for oximetry may be included. The outside diameter is small enough for insertion through a vein of the arm. For monitoring of a cardiac shunt, sensors are configured for measuring pressures upstream and downstream of the cardiac shunt, e.g. in left and right atria, or left atrium and coronary sinus.

13 Claims, 26 Drawing Sheets

(51) Int. Cl.
    A61B 5/0215    (2006.01)
    A61B 5/1455    (2006.01)
    A61M 25/00     (2006.01)
    A61M 25/01     (2006.01)
    A61M 25/10     (2013.01)
(52) U.S. Cl.
    CPC .... *A61M 25/0026* (2013.01); *A61M 25/0105* (2013.01); *A61M 25/10* (2013.01); *A61B 5/02154* (2013.01); *A61B 5/02158* (2013.01); *A61B 2562/0233* (2013.01); *A61B 2562/0247* (2013.01); *A61B 2562/228* (2013.01); *A61M 2025/1061* (2013.01); *A61M 2205/3306* (2013.01); *A61M 2205/3344* (2013.01)
(58) Field of Classification Search
    CPC .... A61B 2562/0233; A61B 2562/0247; A61B 2562/228; A61B 5/02141; A61M 25/0026; A61M 25/0105; A61M 25/10; A61M 2025/1061; A61M 2205/3306
    See application file for complete search history.

(56) References Cited

U.S. PATENT DOCUMENTS

| | | |
|---|---|---|
| 4,730,622 A | 3/1988 | Cohen |
| 4,735,212 A | 4/1988 | Cohen |
| 4,850,358 A | 7/1989 | Millar |
| 4,873,989 A | 10/1989 | Einzig |
| 4,953,553 A | 9/1990 | Tremulis |
| 4,966,148 A | 10/1990 | Millar |
| 5,018,529 A | 5/1991 | Tenerz et al. |
| 5,115,127 A | 5/1992 | Bobb |
| 5,125,058 A | 6/1992 | Tenerz et al. |
| 5,152,291 A | 10/1992 | Dias |
| 5,178,153 A | 1/1993 | Einzig |
| 5,208,650 A | 5/1993 | Giallorenzi |
| 5,226,423 A | 7/1993 | Tenerz et al. |
| 5,392,117 A | 2/1995 | Belleville et al. |
| 5,514,128 A | 5/1996 | Hillsman et al. |
| 5,520,190 A | 5/1996 | Benedict et al. |
| 5,574,699 A | 11/1996 | Cuomo |
| 5,873,835 A | 2/1999 | Hastings et al. |
| 6,107,004 A | 8/2000 | Donadio, III |
| 6,112,598 A | 9/2000 | Tenerz et al. |
| 6,167,763 B1 | 1/2001 | Tenerz et al. |
| 6,254,550 B1 | 7/2001 | Mcnamara et al. |
| 6,336,906 B1 | 1/2002 | Hammarstrom et al. |
| 6,343,514 B1 | 2/2002 | Smith |
| 6,431,010 B1 | 8/2002 | Joffe |
| 6,585,660 B2 | 7/2003 | Dorando et al. |
| 6,615,667 B2 | 9/2003 | Smith |
| 6,976,965 B2 | 12/2005 | Corl et al. |
| 6,986,739 B2 | 1/2006 | Warren et al. |
| 7,097,620 B2 | 8/2006 | Corl et al. |
| 7,134,994 B2 | 11/2006 | Alpert et al. |
| 7,274,956 B2 | 9/2007 | Mott et al. |
| 7,329,223 B1 | 2/2008 | Ainsworth et al. |
| 7,450,989 B2 | 11/2008 | Svanerudh |
| 7,532,920 B1 | 5/2009 | Ainsworth et al. |
| 7,684,657 B2 | 3/2010 | Donlagic |
| 7,689,071 B2 | 3/2010 | Belleville et al. |
| 7,731,664 B1 | 6/2010 | Millar |
| 7,783,338 B2 | 8/2010 | Ainsworth et al. |
| 7,931,603 B2 | 4/2011 | Von Malmborg et al. |
| 7,967,761 B2 | 6/2011 | Smith |
| 7,967,762 B2 | 6/2011 | Corl et al. |
| 8,317,715 B2 | 11/2012 | Belleville et al. |
| 8,758,333 B2 | 6/2014 | Harlan |
| 8,936,401 B2 | 1/2015 | Belleville |
| 9,052,466 B2 | 6/2015 | Belleville et al. |
| 9,149,230 B2 | 10/2015 | Caron |
| 11,272,847 B2 * | 3/2022 | Glover ................. A61B 5/6853 |
| 11,406,271 B2 * | 8/2022 | Glawdel ................ A61F 2/2427 |
| 2003/0095263 A1 | 5/2003 | Varshneya et al. |
| 2003/0100824 A1 | 5/2003 | Warren et al. |
| 2004/0015138 A1 | 1/2004 | Currier et al. |
| 2004/0059211 A1 | 3/2004 | Patel et al. |
| 2004/0075841 A1 | 4/2004 | Van Neste et al. |
| 2004/0253365 A1 | 12/2004 | Warren et al. |
| 2006/0133715 A1 | 6/2006 | Belleville et al. |
| 2006/0287569 A1 * | 12/2006 | Schock ................. A61M 25/10 600/18 |
| 2007/0038173 A1 | 2/2007 | Simpson |
| 2008/0167535 A1 * | 7/2008 | Stivoric ................... F24F 11/30 374/E1.002 |
| 2008/0249388 A1 | 10/2008 | Kumhyr |
| 2008/0312597 A1 | 12/2008 | Uihlein |
| 2010/0228112 A1 | 9/2010 | Von Malmborg |
| 2010/0234698 A1 * | 9/2010 | Manstrom ............ A61M 25/09 600/478 |
| 2010/0241008 A1 | 9/2010 | Belleville et al. |
| 2011/0004198 A1 | 1/2011 | Hoch |
| 2011/0023617 A1 | 2/2011 | Yu et al. |
| 2011/0066047 A1 | 3/2011 | Belleville et al. |
| 2011/0092784 A1 | 4/2011 | Butler et al. |
| 2011/0234698 A1 | 9/2011 | Sakata et al. |
| 2012/0197097 A1 | 8/2012 | Chan |
| 2012/0227505 A1 | 9/2012 | Belleville et al. |
| 2013/0051731 A1 | 2/2013 | Belleville et al. |
| 2013/0218032 A1 | 8/2013 | Belleville |
| 2013/0317372 A1 | 11/2013 | Eberle et al. |
| 2014/0039325 A1 | 2/2014 | Belleville |
| 2014/0107624 A1 | 4/2014 | Belleville |
| 2014/0241669 A1 | 8/2014 | Belleville et al. |
| 2014/0243688 A1 | 8/2014 | Caron et al. |
| 2014/0248021 A1 | 9/2014 | Belleville et al. |
| 2014/0249386 A1 | 9/2014 | Caron et al. |
| 2015/0057532 A1 | 2/2015 | Belleville |
| 2016/0022159 A1 | 1/2016 | Caron et al. |
| 2017/0027458 A1 | 2/2017 | Glover et al. |

FOREIGN PATENT DOCUMENTS

| | | |
|---|---|---|
| EP | 1849409 A1 | 10/2007 |
| JP | H05329119 A | 12/1993 |
| JP | 2003507111 A | 2/2003 |
| JP | 2005291945 A | 10/2005 |
| JP | 2007296354 A | 11/2007 |
| JP | 2016077361 A | 5/2016 |
| WO | 0113789 A1 | 3/2001 |
| WO | 2010071737 A1 | 6/2010 |
| WO | 2011048509 A1 | 4/2011 |
| WO | 2011101813 A1 | 8/2011 |
| WO | 2012061935 A1 | 5/2012 |
| WO | 2012164481 A1 | 12/2012 |
| WO | 2015142623 A1 | 9/2015 |
| WO | 2016009317 A1 | 1/2016 |
| WO | 2016178171 A1 | 11/2016 |
| WO | 2019095049 A1 | 5/2019 |
| WO | 2019142152 A1 | 7/2019 |

OTHER PUBLICATIONS

"Swan-Ganz—right heart catheterization", NIH National Library of Medicine, online Medical Encyclopedia, Update Date Aug. 12,

(56) References Cited

OTHER PUBLICATIONS 2014 (https://www.nlm.nih.gov/medlineplus/ency/article/003870.htm); 4 pages.
"Pulmonary artery catheter", Wikipedia, version last modified May 8, 2016 (https://en.wikipedia.org/wiki/Pulmonary_artery_catheter); pp. 1-5.
Jan M. Headley, RN, BS, CCRN; "Invasive Hemodynamic Monitoring: Physiological Principles and Clinical Applications"; Edwards Life Sciences; Irvine, California, © 2002 (http://ht.edwards.com/resourcegallery/products/swanganz/pdfs/invasivehdmphysprincbook.pdf ); 40 pages.
B. Paunovic et al., "Pulmonary Artery Catheterization", (c) 2011, updated Jan. 3, 2016 (http://emedicine.medscape.com/article/1824547 (c) 2011); 10 pages.
"Right Heart Catheterization", Johns Hopkins Medicine Health Library, version downloaded Aug. 2016 (http://www.hopkinsmedicine.org/healthlibrary/test_procedures/cardiovascular/right_heart_catheterization_135,40/ ); 7 pages.
M. Kern, "Comparing FFR Tools New wires Pressure Microcatheter", Cath Lab Digest, vol. 24, Issue 5, May 2016 (http://www.cathlabdigest.com/article/Comparing-FFR-Tools-New-Wires-Pressure-Microcatheter); 4 pages.
de Vecchi et al., "Catheter induced Errors in Pressure Measurements in Vessels: An in-vitro and numerical study" IEEE Transactions on Biomedical Engineering, vol. 61, No. 6, Jun. 2014; pp. 1844-1850.
Robert G. Gray et al., "Feasibility of In Vivo Pressure Measurement using a pressure tip catheter via transventricular puncture", Asaio J. 2010 56(3) 194-199; May 1, 2011; pp. 1-14.
Eric Pinet, et al., FISO Technologies, "Temperature fiber-optic point sensors: Commercial technologies and industrial applications", MIDEM Conference Proceedings, Sep. 29-Oct. 1, 2010, Radenci, Slovenia, D. Đonlagić, I. Šorli, & P. Šorli (Eds), MIDEM (Pub.) ISBN 978-961-92933-0-0; pp. 31-43.
Boston Scientific—Comet(TM) FR Guidewire—Product Literature-Oct. 2015; 2 pages.
Volcano Prime Wire Prestige-Product literature-Nov. 2012; 1 page.
Javier Escaned, "Boston Scientific: Designing the pressure guidewire for contemporary PCI scenarios", European Heart House, Coronary Physiology in the Catheterization Laboratory (9th Edition) Thursday Apr. 23-Saturday Apr. 25, 2015; 15 pages.
Opsens Medical, Product Brochure "One Wire. Many possibilities" Opto Wire One, www.opsensmedical.com, 2014 Brochure; 5 pages.
Webb, et al., "Current Status of Transcatheter Aortic Valve Replacement", Journal of the American College of Cardiology, vol. 60, No. 6, 2012; pp. 483-492.
Roy, D. A. et al., "First-in-man assessment of a dedicated guidewire for transcatheter aortic valve implantation", EuroIntervention 2013, 8, pp. 1019-1025.
Volcano Prime Wire Prestige—Product Literature: Jan. 2015 and Feb. 2015; 3 pages.
St. Jude Medical—PressureWire Aeris; Agile Tip Technology; "Wireless FFR Measurement with Outstanding Handling Performance" Product Literature; 2013; 2 pages.
Pinet et al.; "Ultra-miniature all-glass Fabry-Perot pressure sensor manufactured at the tip of a multimode optical fiber"; FISO Technologies Inc.; Proceedings of SPIE, vol. 6770 (2007).
Hamel et al.; "Temperature and pressure Fiber-Optic sensors applied to minimally invasive diagnostics and therapies"; FISO Technologies Inc.; Whitepaper/Publication; (2006).
Pinet, Eric; "Pressure measurement with fiber-optic sensors; Commercial technologies and applications"; FISO Technologies Inc.; 21st International Conference on Optical Fiber Sensors, edited by Wojtek J. Bock et al.; Proc. of SPIE vol. 7753 (May 17, 2011).
Pinet, Eric; "Disposable fiber-optic sensors for clinical environments"; SPIE 2007.
Tenerz, L.; "A Fiberoptic Silicon Pressure Microsensor for Measurements in Coronary Arteries"; Radi Medical Systems; IEEE 1991.
Hamel et al.; "Pressure Fiber-Optic Sensors in Intra-aortic Balloon Pumping Therapy"; European Medical Device Manufacturer Editorial: Sensors and Transducers integrated in medical equipment or used in manufacturing process; FISO Technologies Inc.; Whitepaper/Publication; (2006).
FOP-F125 Pressure Sensor; FISO Technologies Inc.; Preliminary Datasheet dated 2008.
PressureWire Certus FFR Measurement System; Product information dated 2011 and 2009.
PressureWire Certus FFR Measurement System; Product information; 2011.
Vaguine et al.; "Multiple Sensor Optical Thermometry System for Application in Clinical Hyperthermia" IEEE Transactions on Biomedical Engineering vol. BME-31, No. 1, pp. 168-172; Jan. 1984.
Silvestri et al.; Optical fiber measurement systems for medical applications; p. 205-225; Oct. 5, 2011.
Chinese Office Action (with English Translation) issue on CN Application No. 201280059712.X; Nov. 3, 2015; 14 pages.
Harrison, G. J. et al.; Experimental Investigation; "Guidewire Stiffness: What's in a Name?" J. Endovasc. Ther. 2011:18, pp. 797-801.
St. Jude Medical—Product Literature: PressureWire Certus FFR Measurement System; 2011; 5 pages.
JPO Machine translation of JP2005-291945.
JPO Machine translation of JPH05-329119.
Extended European Search Report issued on related EP Application No. 20873090.3 dated Sep. 20, 2023; 17 pages.
International Search Report and Written Opinion of the International Searching Authority for PCT Application No. PCT/CA2020/051294; mailed Jan. 5, 2021; 16 pages.

* cited by examiner

A-A CUT-THROUGH VIEW OF FIGS. 1 AND 3

A-A CUT-THROUGH VIEW OF FIGS. 5, 6 AND 9

B-B CUT-THROUGH VIEW OF FIG. 6

A-A CUT-THROUGH VIEW OF FIG. 10

B-B CUT-THROUGH VIEW OF FIG. 10

A-A CUT-THROUGH VIEW OF FIG. 17

B-B CUT-THROUGH VIEW OF FIG. 17

A-A CUT-THROUGH VIEW OF FIG. 19

B-B CUT-THROUGH VIEW OF FIG. 19

CUT-THROUGH VIEW OF FIG. 17

CUT-THROUGH VIEW OF FIG. 17

CUT-THROUGH VIEW OF FIG. 1

A-A CUT-THROUGH VIEW OF FIG. 17

B-B CUT-THROUGH VIEW OF FIG. 17

MULTI-SENSOR CATHETER FOR RIGHT HEART AND PULMONARY ARTERY CATHETERIZATION

CROSS-REFERENCE TO RELATED APPLICATIONS

This application claims priority from U.S. patent application Ser. No. 16/587,815, filed Sep. 30, 2019, entitled "System and Apparatus comprising a Multi-Sensor Catheter for Right Heart and Pulmonary Artery Catheterization", which is a Continuation-in-Part of U.S. patent application Ser. No. 15/293,380, filed Oct. 14, 2016, entitled "System and Apparatus comprising a Multi-Sensor Catheter for Right Heart and Pulmonary Artery Catheterization"; both applications are incorporated herein by reference, in their entirety.

TECHNICAL FIELD

The present invention relates to a system and apparatus comprising a multi-sensor catheter for use in cardiology, and more particularly to a pulmonary artery catheter for right heart catheterization and related diagnostic measurements.

BACKGROUND

The above referenced related patent applications disclose multi-sensor guidewires and multi-sensor micro-catheters for use in interventional cardiology. For example, if a heart valve is found to be malfunctioning because it is defective or diseased, minimally invasive methods are known for repair and replacement of the heart valve, by introduction of a catheter intravascularly into the heart to access the heart valve. Percutaneous procedures for minimally invasive transcatheter heart valve diagnosis, repair and replacement avoid the need for open heart surgery. These procedures may be referred to as Transcatheter Valve Therapies (TVT).

TVT for valve repair include, for example, procedures such as, balloon valvuloplasty to widen an aortic valve which is narrowed by stenosis, or insertion of a mitral clip to reduce regurgitation when a mitral valve fails to close properly. Alternatively, if the valve cannot be repaired, a prosthetic replacement valve may be introduced. Minimally invasive Transcatheter heart Valve Replacement (TVR) procedures, including Transcatheter Aortic Valve Implantation (TAVI or TAVR) and Transcatheter Mitral Valve Implantation (TMVI), have been developed over the last decade and have become more common procedures in recent years.

While there have been many recent advances in systems and apparatus for TVT and for related diagnostic procedures, interventional cardiologists who perform these procedures have identified the need for improved apparatus for use in TVT, including apparatus for heart valve replacement. They are also seeking improved diagnostic equipment that provides real-time direct measurements, i.e. within the heart, of important hemodynamic cardiovascular parameters before, during and after TVT.

U.S. patent application Ser. No. 14/874,604 (U.S. Pat. No. 9,504,392) and U.S. patent application Ser. No. 14/354,624 (U.S. Pat. No. 9,149,230) disclose a multi-sensor micro-catheter and a multi-sensor guidewire. These multi-sensor micro-catheters and guidewires comprise a distal end portion containing multiple optical sensors arranged for measuring blood pressure at several sensor locations, e.g. simultaneously, in real-time. Optionally, they include an optical or electrical sensor for measuring blood flow. The disclosed multi-sensor micro-catheters and multi-sensor guidewires can be configured for use in minimally invasive surgical procedures for measurement of intra-vascular pressure gradients, and more particularly, for direct measurement of a transvalvular pressure gradient within the heart, for any one of the four heart valves.

For example, a transvalvular measurement of pressure across the aortic valve, i.e. with pressure sensors positioned to measure pressure concurrently in the ascending aorta and left ventricle, allows for assessment of aortic regurgitation, before and after a TAVI procedure.

A need for improved diagnostic apparatus for right heart catheterization (RHC) and pulmonary artery (PA) catheterization has also been identified. For example, RHC may be performed in an Intensive Care Unit (ICU) for monitoring of critically ill patients. In a Cardiac Catheterization Lab (Cath Lab), RHC may be used for monitoring and diagnosis, e.g. during TVT, and in the operating room (OR) for monitoring of important hemodynamic parameters during cardiac surgery or other high-risk surgery.

During RHC and PA catheterization, a special balloon tipped catheter, which may be referred to as a pulmonary artery catheter (PA catheter) or a Swan Ganz (SG) catheter, is introduced through one of the larger veins, e.g. through an internal jugular vein, subclavian vein in the neck, or a median cubital vein in the arm, into the superior vena cava, or through a femoral vein into the inferior vena cava. The catheter tip is then introduced from the vena cava into the right atrium of the heart, advanced through the tricuspid valve into the right ventricle, and then through the pulmonic valve (alternatively called the pulmonary valve) into the PA, which is the main artery that carries de-oxygenated blood from the heart to the lungs. One lumen of the PA catheter extends from the proximal end to an opening at the distal tip. This lumen is fluid filled and is connected at its proximal end to an externally placed pressure transducer to enable the pressure at the distal tip to be monitored. Thus, the pressure at the distal tip may be monitored by the catheter as it is advanced sequentially, firstly into the right atrium (RA), secondly into the right ventricle (RV) and thirdly into the PA. During these measurements, the balloon may be partially inflated to allow the balloon to "float" and be drawn into the PA by the blood flow. Subsequently, after further inflating the balloon, the balloon is drawn by the blood flow and wedges in a smaller pulmonary blood vessel for measurement of a Pulmonary Capillary Wedge Pressure (PCWP). PCWP is an indirect measure of the left atrial pressure (LAP) and left ventricular end-diastolic pressure (LVEDP). At each point a characteristic pressure waveform is observed, and pressure measurements are recorded. That is, as the catheter tip is advanced, the observed waveform will change sequentially and show the transition from a RA pressure waveform, a RV pressure waveform, a PA pressure waveform and then a PCWP waveform.

Conventional four lumen/four port PA/SG catheters provide: one lumen for pressure monitoring at the catheter tip using an externally connected pressure transducer; a balloon inflation lumen; a thermistor lumen; and a fluid injection lumen for measurement of blood flow by thermo-dilution. The port for the pressure transducer may also be used for blood sampling, e.g. for measurement of mixed venous oxygen saturation ($SvO_2$). Some available PA catheters include two pressure sensing lumens, which can be connected to two external pressure transducers for measurement of pressures in the right atrium and in the pulmonary artery. Advanced PA catheters or SG catheters may also include several additional lumens and ports, e.g. another port for fluid infusion, and/or one or more ports for cable connections to other types of monitoring equipment, e.g. for measurement of cardiac output, oximetry, or insertion of a cardiac pacing wire.

By way of example only, the following references provide further background information and details of insertion techniques, characteristic pressure waveforms, and indications for RHC and PA catheterization:
1) Jeremy Fernando, "Pulmonary Artery Catheters", updated 22 Dec. 2014;
2) "Swan-Ganz—right heart catheterization", NIH National Library of Medicine, online Medical Encyclopedia, Update Date Aug. 12, 2014;
3) "Pulmonary artery catheter", Wikipedia, version last modified 8 May 2016;
4) "Invasive Hemodynamic Monitoring: Physiological Principles and Clinical Applications" pp. 12-15; Jan M. Headley, RN, BS, CCRN, Edwards Life Sciences; Irvine, California, © 2002;
5) B. Paunovic et al., "Pulmonary Artery Catheterization", Medscape article no. 1824547, (c) 2011, updated 3 Jan. 2016;
6) "Right Heart Catheterization", Johns Hopkins Medicine Health Library, version downloaded August 2016;
7) "Comparing FFR Tools New wires Pressure Microcatheter", M. Kern, Cath Lab Digest, Volume 24, Issue 5, May 2016.

Conventional balloon tipped PA catheters that use a fluid filled catheter, which is coupled to an externally placed pressure transducer, are relatively inexpensive and durable. However, they measure pressure only at a single point, i.e. at the tip of the catheter. Thus, the cardiologist must reposition the catheter, i.e. by pushing and pulling the catheter tip back and forth to position the tip to make pressure measurements at different locations within the heart. During this procedure, there is some risk that repeatedly advancing and pulling-back the catheter for repositioning tip of the catheter for pressure sensing will interfere with, or disrupt, normal operation of the heart, e.g. cause cardiac arrhythmias (such as atrial or ventricular fibrillation), interfere with opening and closing of the heart valves, or risk damage to the heart tissues.

Also, fluid filled pressure sensing catheters have limited accuracy. Measurements may be affected by technical limitations such as reflection of the pressure wave at the tip and distortion if the catheter is kinked or sharply bent. Inertial artefacts and slow dynamic response (time lag, damping, hysteresis, resonances, frequency filtering) can distort the waveform, in time and amplitude, as it travels through the fluid filled lumen (de Vecchi et al., "Catheter induced Errors in Pressure Measurements in Vessels: An in-vitro and numerical study" IEEE Transaction on Biomedical Engineering, Vol. 61, No. 6, June 2014). Measurement errors as much as 20 mmHg have been reported (see ref. 2 in Robert G. Grey et al., "Feasibility of In Vivo Pressure Measurement using a pressure tip catheter via transventricular puncture", ASAIO J. 2010 56(3) 194-199. This reference also compares limitations of a Pressure Tipped Catheter (PTC) using a piezo-electric pressure sensor and a conventional fluid filled pressure sensing catheter.

Limitations of pressure sensing catheters with externally placed transducers are also discussed in United States patent application publication no. US2011/004198, to Hoch, which discloses a central venous catheter (CVC) using a piezo-electric pressure sensor. However, electrical pressure sensors of this type have some drawbacks for in vivo applications, where long thin electrical wires are carrying small electrical signals in humid environment, e.g. requirement for electrical isolation of electrical components, significant electrical drift and temperature sensitivity and electrical interference, such as, cross-talk between wires from multiple electrical sensors and from external electromagnetic sources within the operating room.

Thus, there is a need for improved or alternative PA catheters for direct measurements of cardiovascular parameters, including blood pressure measurements, during RHC and PA catheterization procedures.

An object of the present invention is to provide for improvements or alternatives to known systems and apparatus comprising multi-sensor catheters or multi-sensor guidewires.

SUMMARY OF INVENTION

The present invention seeks to mitigate one or more disadvantages of known systems and apparatus comprising multi-sensor catheters for measuring cardiac hemodynamic parameters.

Systems and apparatus are disclosed having particular applicability for cardiac catheterization for assessment of a cardiac hemodynamic condition, e.g. heart failure, during RHC and PA catheterization for concurrent measurement of blood pressure in the RA and PA.

A first aspect of the invention provides a flow-directed multi-sensor catheter for right heart and pulmonary artery catheterization, configured for the assessment of a cardiac hemodynamic condition, by direct monitoring of a right atrial pressure and a pulmonary artery pressure, comprising:
- a length of multi-lumen catheter tubing comprising a plurality of lumens extending between a proximal end and a distal end comprising an atraumatic distal tip;
- one of the lumens being a guidewire lumen having a proximal port and an opening at the distal tip of the catheter tubing, an inflatable balloon near the distal tip, and one of the lumens being a balloon inflation lumen, the inflatable balloon being coupled by the balloon inflation lumen to a balloon inflation port at the proximal end of the catheter tubing;
- a plurality of optical sensors and a plurality of optical fibers;
- a sensor end of each optical fiber being attached and optically coupled to an individual one of the plurality of optical sensors; each optical sensor and its optical fiber being inserted into a respective lumen of the multi-lumen catheter tubing;
- a proximal end of each of the plurality of optical fibers being coupled to an optical input/output connector at the proximal end of the catheter for connection to an optical control system;
- the plurality of optical sensors forming a sensor arrangement comprising first and second optical pressure sensors at respective sensor locations spaced apart lengthwise within a length of a distal end portion of the catheter tubing, with an aperture in the catheter tubing adjacent each optical pressure sensor for fluid contact; and
- wherein the pressure sensor locations are configured to position the first pressure sensor in the pulmonary artery and the second pressure sensor in the right atrium during right heart and pulmonary artery catheterization, for blood concurrent pressure measurements at each optical pressure sensor location.

The multi-lumen catheter tubing has an outside diameter that is small enough to enable insertion into the heart through a peripheral vein, e.g. insertion into the heart through a vein in the upper or lower arm. For example, the multi-lumen catheter tubing has an outside diameter of ≤5 French, and preferably an outside diameter of ≤4 French.

The multi-sensor catheter may further comprise an optical fiber for optical oximetry, which extends through one of the lumens from the optical input/output connector at the proximal end to an aperture for fluid contact at the distal tip, e.g. to enable concurrent measurement of $SvO_2$ in the PA, while optical pressure sensors measure RA and PA blood pressure.

In some embodiments, the multi-sensor catheter comprises three lumens. First and second lumens each accommodate one of the optical pressure sensors and its optical fiber, and a third lumen serves as the guidewire lumen. The third lumen may also be used for fluid sampling and injection. For example, the guidewire lumen may also be used for blood sampling at the tip of the catheter, e.g. for measurement of $SvO_2$, or for measurement of cardiac output by the Fick method.

Where a three lumen catheter comprises lumens identified as first, second and third lumens, and first and second optical sensors and optical fibers: the first lumen is both: the lumen for the second optical pressure sensor and its optical fiber; and the balloon inflation/deflation lumen coupled to the inflatable balloon; the second lumen is lumen for the second optical pressure sensor and its optical fiber; and the third lumen is the guidewire lumen. The guidewire lumen may also be used for fluid injection and fluid sampling. If the multi-sensor catheter further comprises a third optical fiber for optical oximetry, the optical fiber for oximetry extends through the second lumen (the same lumen as the second optical fiber and the second optical pressure sensor) from the optical input/output connector at the proximal end an aperture for fluid contact for oximetry at the distal tip.

Where a lumen has more than one function, e.g. the first lumen being for the first optical pressure sensor and a balloon inflation lumen, a portion of the lumen near the first optical pressure sensor is isolated from a portion of the lumen containing the balloon inflation port by one or more plugs or seals at the appropriate location in the lumen, e.g. a bolus of gel or sealant injected into the lumen around the optical fiber near the proximal end, and a bolus of sealant injected into the lumen to seal around the optical fiber between the balloon inflation port and the first optical pressure sensor. Where an optical fiber for oximetry is provided in the second lumen containing the second optical pressure sensor and its optical fiber, a bolus of sealant is injected into the second lumen to isolate the second pressure sensor from the aperture at the distal tip for the oximetry fiber.

In the embodiments, the optical pressure sensors comprise Fabry-Pérot Micro-Opto-Mechanical System (FP MOMS) sensors, e.g. having a diameter of 0.260 mm or less.

In some embodiments, the proximal end of the multi-lumen catheter comprises a hub, and the optical input/output connector comprises a multi-port optical connector; and the proximal ends of optical fibers for each optical sensor extending through a respective lumen of the multi-lumen catheter tubing, through the hub, and through a length of flexible tubing to respective optical ports of the multi-port optical connector.

In some embodiments, the proximal end of the multi-lumen catheter comprises a hub and the optical input/output connector comprises a multi-port optical connector; and distal ends of each lumen of the multi-lumen catheter containing an optical fiber are merged into a single lumen through the hub, said single lumen of the hub being connected to a length of flexible tubing through which the proximal ends of the optical fibers are connected to respective optical ports of the multi-port optical connector.

Another aspect of the invention provides a multi-sensor catheter configured for monitoring of a cardiac shunt, through direct monitoring of blood pressures upstream and downstream of the cardiac shunt, comprising:
  a length of multi-lumen catheter tubing comprising a plurality of lumens extending between a proximal end and a distal end comprising an atraumatic distal tip;
  one of the lumens being a guidewire lumen having a proximal port and an opening at the distal tip of the catheter tubing,
  a plurality of optical sensors and a plurality of optical fibers; a sensor end of each optical fiber being attached and optically coupled to an individual one of the plurality of optical sensors;
  each optical sensor and its optical fiber being inserted into a respective lumen of the multi-lumen catheter tubing;
  a proximal end of each of the plurality of optical fibers being coupled to an optical input/output connector at the proximal end of the catheter for connection to an optical control system; and
  the plurality of optical sensors forming a sensor arrangement comprising first and second optical pressure sensors at respective sensor locations spaced apart lengthwise within a distal end portion of the catheter tubing, with an aperture in the catheter tubing adjacent each optical pressure sensor for fluid contact; and
  wherein the pressure sensor locations are configured to place the first pressure sensor in the left atrium (LA) for monitoring of LA pressure and to place the second pressure sensor downstream of the cardiac shunt, for concurrent blood pressure measurements at each optical pressure sensor location.

When the cardiac shunt is an inter-atrial shunt between the LA and the right atrium (RA), the pressure sensor locations are configured to place the first pressure sensor in the LA for monitoring of LA pressure and the second pressure sensor in the RA for monitoring of central venous pressure CVP. When the cardiac shunt is between the LA and a coronary sinus, the pressure sensor locations are configured to place the first pressure sensor in the LA for monitoring of LA pressure and the second pressure sensor in the coronary sinus. The optical sensors may comprise a third optical pressure sensor, wherein the first, second and third optical pressure sensor locations are configured for concurrent measurements of blood pressure in the LA, and downstream of the cardiac shunt in the coronary sinus and in the RA.

A further aspect of the invention comprises a control system for multi-sensor catheters, such as, the multi-sensor PA catheters disclosed herein, in which digital outputs from first and second optical pressure sensors are converted by a circuit emulating two BP-22 outputs from two blood pressure transducers P1 and P2 to allow for connection directly to a BP-22 compliant PCM.

The control system comprises a light source and detector, and an optical interface for coupling, via respective input/output ports, to each of the optical fibers and optical sensors of a multi-sensor catheter or multi-sensor guidewire; data storage and processing means configured for processing optical data indicative of pressure values; and wherein, for right heart catheterization and pulmonary artery catheterization, the processing means is further configured for graphically displaying pressure data comprising a plurality of concurrent blood pressure waveforms. Thus, when the multi-sensor catheter comprises at least two optical pressure sensors, the system can process optical data from each sensor and display concurrent blood pressure waveforms from at least two of right atrium, right ventricle and pulmonary artery. In an embodiment, the control system includes a circuit emulating two BP-22 outputs for each optical pressure sensor, which converts digital outputs from each optical pressure sensor for direct connection to a BP-22 compliant PCM.

The concurrent blood pressure waveforms for each optical sensor may be displayed together for comparison, or displayed individually, for one or more time intervals, and during one or more cardiac cycles. Optionally, graphical flow velocity data may also be displayed concurrently. Advantageously, the processing means is further configured to derive and display hemodynamic parameters from the blood pressure data and flow velocity data. For example, during right heart and pulmonary artery catheterization with a multi-sensor catheter as disclosed herein comprising at least two optical pressure sensors, in addition to displaying blood pressure waveforms from the right atrium and pulmonary artery, a plurality of numeric values such as peak pressures, mean pressures, peak-to-peak pressure differentials for each curve, and pressure differentials or gradients between the pulmonary artery pressure and the central venous pressure in right atrium can be displayed in real time.

Accordingly, another aspect of the invention provides a computer program product embodied as a non-transitory computer readable medium storing instructions, for execution in a processor of a control system for a multi-sensor catheter, for processing optical data received concurrently from optical pressure sensors of a multi-sensor catheter, said optical data being indicative of blood pressure, and e.g. displaying a corresponding plurality of blood pressure waveforms, or displaying numeric data relating to selected hemodynamic parameters and indexes.

For example, a control system for a multi-sensor catheter comprising first and second optical pressure sensors comprises: a light source and detector, and an optical interface for coupling, via respective input/output ports, to each of the optical fibers and optical sensors of the multi-sensor catheter; data storage and a processor configured for processing optical data indicative of pressure values received from each of the first and second optical pressure sensors, e.g. from optical pressure sensors positioned in the right atrium and pulmonary artery, or positioned upstream and downstream of a cardiac shunt.

When the multi-sensor catheter comprises an optical oximeter, the data storage and processor is configured for processing optical data indicative blood oxygen levels received from the optical oximeter, which is e.g. located at a distal tip of the multi-sensor catheter.

The control system may be configured for processing using hardware and/or software.

For example, a computer program product is embodied as a non-transitory computer readable medium storing instructions, for execution in a processor of a control system for a multi-sensor catheter comprising first and second optical pressure sensors, for processing optical data received concurrently from the first and second optical pressure sensors said optical data being indicative of blood pressure, and communicating data, e.g. comprising blood pressure waveforms and/or numeric data relating to selected hemodynamic parameters, to a remote monitoring system.

The control system may comprise a circuit emulating two BP-22 outputs for each optical pressure sensor, which converts digital outputs from each optical pressure sensor for direct communication with a BP-22 compliant PCM.

In some embodiments, the control system comprises a portable unit, e.g. a compact wearable unit having a wireless communications interface for remote patient monitoring. A portable controller allows for more mobility for patients within a hospital situation or in a care facility. A compact wearable device allows for in-home use and remote monitoring. For example, the portable unit has a communications interface for communicating with a remote patient monitoring system 4151, directly through a communications interface to a hospital network or through a communications network 4200, e.g. via a personal computing device or an app on the patient's smartphone.

Thus, embodiments of systems and apparatus comprising a flow directed multi-sensor PA catheter are disclosed that mitigate one or more problems with known systems and apparatus for RHC and PA catheterization, which allow for diagnostic measurements and monitoring of a cardiac hemodynamic condition, such as heart failure, including measurement of blood pressure concurrently within the RA and PA.

In other embodiments, systems and apparatus comprising a multi-sensor catheter are disclosed, that allow for assessment of a cardiac hemodynamic condition after a cardiac shunt has been created, using direct measurement of blood pressures upstream and downstream of the cardiac shunt.

The foregoing and other objects, features, aspects and advantages of the present invention will become more apparent from the following detailed description, taken in conjunction with the accompanying drawings, of embodiments of the invention, which description is by way of example only.

BRIEF DESCRIPTION OF THE DRAWINGS

In the drawings, identical or corresponding elements in the different Figures have the same reference numeral.

DETAILED DESCRIPTION OF EMBODIMENTS

Figure 1:
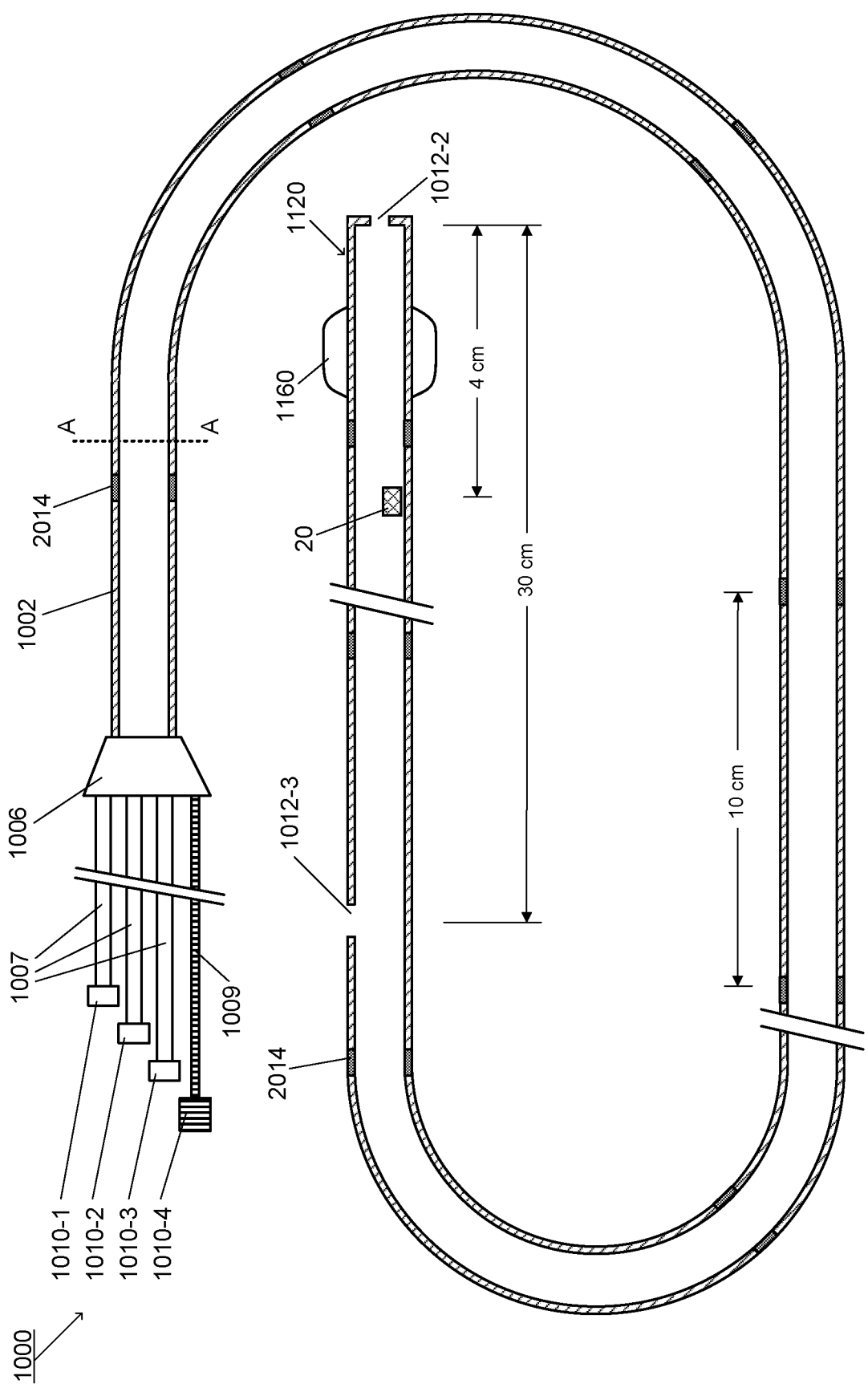
FIG. 1 (Prior Art) shows a schematic longitudinal cross-sectional view of a known type of conventional PA catheter, which may be referred to as a Swan Ganz catheter.
Figure 2:
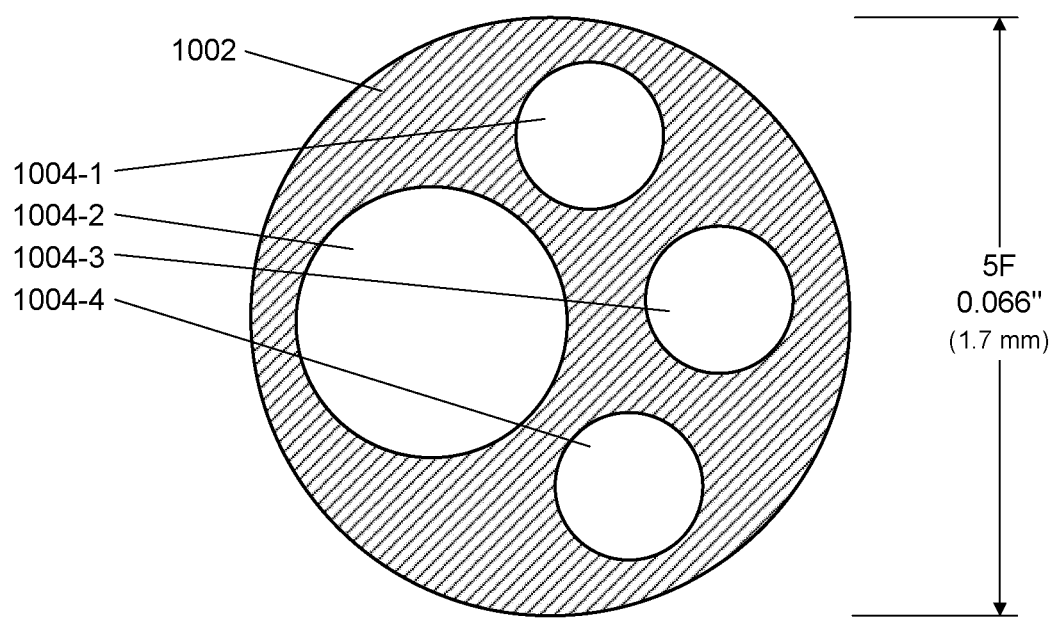
FIG. 2 (Prior Art) shows an enlarged transverse cross-sectional view of the PA catheter illustrated in FIG. 1 taken through plane A-A of FIG. 1 to show the lumens of the multi-lumen catheter tubing.

As illustrated schematically in the longitudinal cross-sectional view shown in FIG. 1, a conventional PA catheter 1000, which may be referred to as a Swan Ganz catheter, comprises a length of multi-lumen catheter tubing 1002 having at its distal end 1120 an inflatable balloon 1160. The catheter typically comprises a multi-lumen catheter tubing 1002, such as illustrated in FIG. 2, which is a cross-sectional view through plane A-A of FIG. 1. By way of example, the catheter tubing shown in FIG. 2 has four lumens 1004-1, 1004-2, 1004-3 and 1004-4, and an outside diameter of 5 French. Referring back to FIG. 1, there is a hub 1006 at the proximal end of the catheter with individual proximal ports 1010-1, 1010-2, 1010-3, and 1010-4. Ports 1010-1, 1010-2, 1010-3 are coupled by individual lengths of flexible tubing 1007 through the hub 1006 to respective lumens 1004-1, 1004-2 and 1004-3 of the catheter tubing 1002. Port 1010-4 is an electrical connector for a thermistor 20 which is located within the fourth lumen 1004-4 proximal to the balloon tip 1160, towards the distal end. Electrical connections for the thermistor 20 extend through lumen 1004-4 from the thermistor 20 to an electrical cable 1009 extending from the hub 1006. For simplicity of illustration of the longitudinal cross-sectional view shown in FIG. 1, the inner walls of the lumens are not shown.

Traditionally, the multi-lumen catheter tubing 1002 of a Swan Ganz catheter is colored yellow and each of the ports 1010-1 to 1010-4 is color coded. A first lumen 1004-1 provides for inflating the balloon and has a corresponding proximal port 1010-1 for coupling to an air-filled syringe for inflating and deflating the balloon. The balloon inflation port is conventionally colored red. The balloon 1160 typically has a volume of 0.5 ml to 1.5 ml and is connected to the balloon inflation lumen 1004-1. A second lumen 1004-2 is has an aperture 1012-2 opening at the distal tip 1120 and is connected at the proximal end to a proximal port 1010-2 (conventionally colored yellow) for connection to an externally placed pressure transducer, so that, when this lumen is filled with fluid, the blood pressure at the tip 1120 can be sensed. This port and lumen may also be used for sampling of blood at the tip of the catheter. For measurement of flow by thermo-dilution using the thermistor 20, there is third lumen 1004-3, which has a proximal injectate port (conventionally coloured blue) to allow for injection of a bolus of cold thermo-dilution fluid; this lumen has an injectate opening 1012-3 a distance of approximately 30 cm from the distal tip 1120. The fourth lumen 1004-4 accommodates the thermistor 20, i.e. an electrical temperature sensor, which is typically located at a distance of about 4 cm from the distal tip 1120; the electrical wires (not shown in FIG. 1) for the thermistor 20 extend through lumen 1004-4 to a proximal port 1010-4 (conventionally colored yellow) which comprises an electrical connector for the thermistor T. In this example, the second lumen 1004-2, which has an opening 1012-2 at the distal tip 1120 and respective proximal port 1010-2 has a larger diameter to allow for insertion of a guidewire, e.g. a standard 0.025 inch or 0.018 inch guidewire, to assist with introduction of the PA catheter into the right heart.

Figure 3:
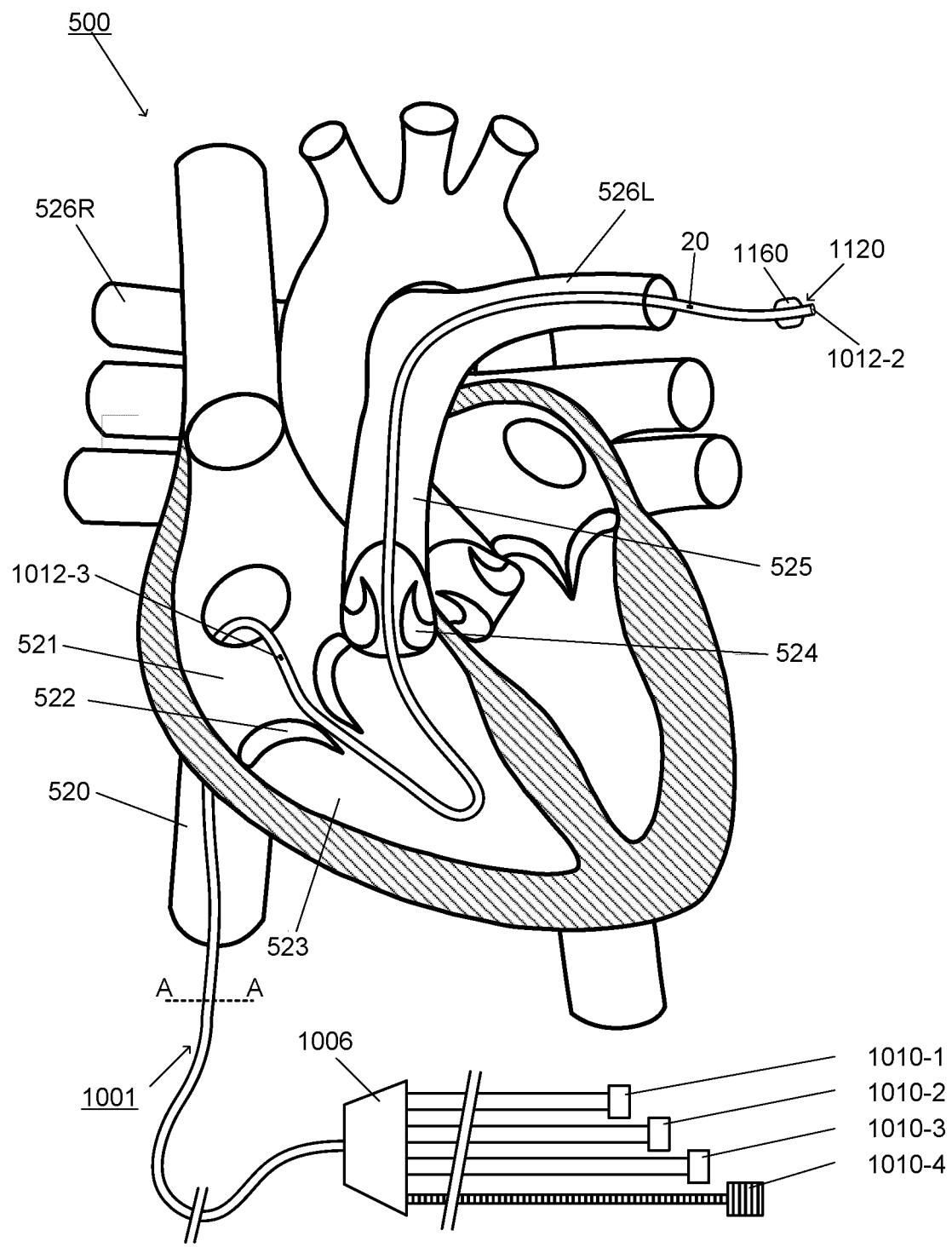
FIG. 3 (Prior Art) shows schematic partial cross-sectional view of a human heart to illustrate placement of a conventional PA catheter within the right heart and the PA for measurement of pressure in the PA and for measurement of blood flow by thermo-dilution.

FIG. 3 illustrates schematically a partial cross-sectional view of a human heart 500 with a PA catheter 1001 positioned within the right heart and left branch of the PA. The PA catheter 1001 comprises four lumens, e.g. as shown in FIG. 2, i.e. one for balloon inflation, one for pressure sensing, one for the thermistor and one for fluid injection for measurement of flow by thermo-dilution. Similar to the catheter shown in FIGS. 1 and 2, the four lumens are connected through a hub 1006 to proximal ports 1010-1, 1010-2, 1010-3 and 1010-4. The first lumen 1004-1 (see FIG. 2) opens to the inflatable balloon 1160 and the first lumen is connected to the balloon inflation/deflation port 1010-1 for connection to an air filled syringe; the second lumen 1004-2 (see FIG. 2) has an opening 1012-2 at the distal tip 1120 and a distal port 1010-2. The distal port 1010-2 that is used for the guidewire insertion can also be used either for connection to an external pressure transducer for measurement of blood pressure at the distal tip 1120, or, for blood sampling, such as for measuring mixed venous oxygen saturation (SvO$_2$). The third port 1010-3 is the proximal injection port which is connected to the third lumen 1004-3 (FIG. 2) for fluid injection into the right atrium 521 through opening 1012-3. The fourth port 1010-4 comprises an electrical connector for the thermistor 20 which is located in the fourth lumen 1004-4 (see FIG. 2) near the distal tip 1120.

To position the PA catheter 1001 as illustrated schematically in FIG. 3, the catheter tip 1120 is introduced into the right atrium (RA) 521, e.g. in this example upwards through the inferior vena cava 520, and through the atrioventricular (tricuspid) valve 522 and into the right ventricle (RV) 523. During introduction, partial inflation of the balloon 1160 allows for blood flow directed insertion. That is, with partial inflation of the balloon 1160 in the right ventricle 523, the tip 1120 of the catheter tends to be drawn by the blood flow through the pulmonic valve 524 into the PA 525 and then from the PA towards the right or left branches 526L and 526R of the PA, and towards smaller pulmonary vessels which lead to the lungs. Pressure sensing at the tip is achieved by the fluid filled lumen 1004-2 (FIG. 2) which has opening 1012-2 at the distal tip 1120, and a proximal port 1010-2 which is connected to the externally placed pressure transducer for monitoring pressure at the catheter tip 1120. The port 1010-4 provides for electrical connections for the thermistor 20 (T), which located about 4 cm proximally from the balloon tip 1160, for measurement of blood flow by thermo-dilution. As illustrated schematically in FIG. 3, the opening 1012-3 of the fluid injection lumen is positioned to allow for injection of a bolus of cold fluid into the right atrium of the heart, for detection of a temperature change by the thermistor 20 (T) when the cold fluid reaches the PA 525 and its left and right branches 526L and 526R, to measure blood flow by a conventional thermo-dilution technique.

Figure 4:
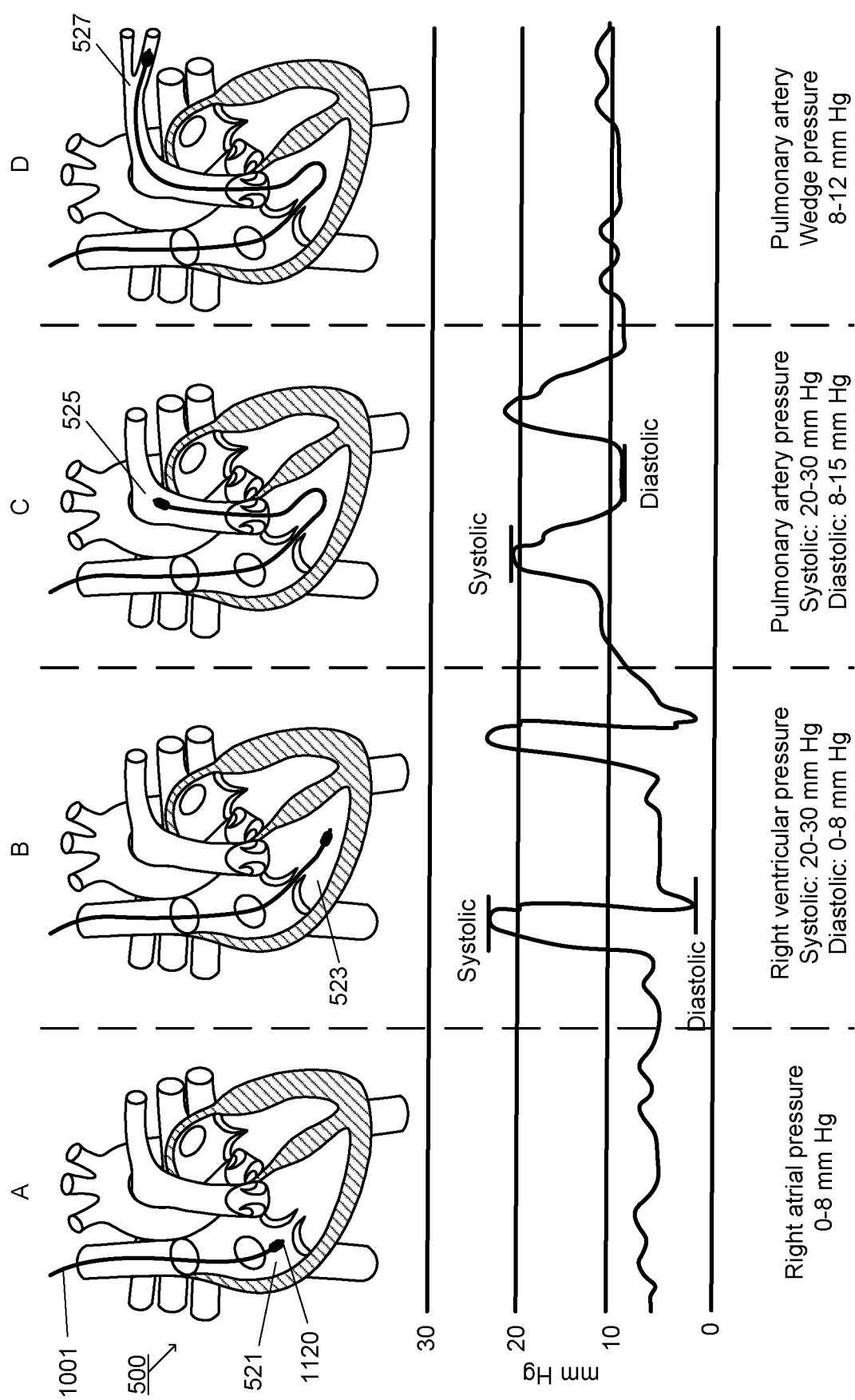
FIG. 4 (Prior Art) shows schematic diagrams of a human heart to illustrate schematically placement of the conventional PA catheter within the right heart and PA for pressure measurements, at each the following positions: A. in the right atrium (RA); B. in the right ventricle (RV); C. in the pulmonary artery (PA); and D. in a pulmonary capillary wedge position (PCWP); the underlying plots show examples of a sequence of typical blood pressure waveform for each of positions A, B, C and D.

In use of the PA catheter 1001, as illustrated in FIG. 4 (Prior Art), when the tip 1120 of the catheter 1001 is first introduced into the heart 500, e.g., through the superior vena cava as illustrated, and into the RA 521 (position A), a pressure measurement is made in the RA to assess the RA waveform. Then the tip of the catheter is advanced through the tricuspid valve 522 into the RV 523 (position B), and a pressure measurement is made within the RV to assess the RV waveform. The balloon is partially inflated so that the blood flow draws the balloon from the right ventricle 523, through the pulmonic valve 524 into the PA 525. When the tip of the catheter is in the PA (position C), the balloon is deflated, and another pressure measurement is made to assess the PA waveform. The tip of the catheter is then allowed to be drawn further into the PA and the balloon at the tip of the catheter is further inflated. When the inflated balloon wedges in a smaller branch 527 of the pulmonary vessels (position D) another pressure measurement is made, called the PA occlusion pressure, or pulmonary capillary "wedge" pressure (PCWP) waveform. PCWP provides an indirect measure of the left atrial pressure (LAP) and left ventricular end-diastolic pressure (LVEDP). As illustrated by the blood pressure waveform in the low part of FIG. 4, as the catheter tip is advanced, the observed waveform changes sequentially and show the transition from a RA pressure waveform, a RV pressure waveform, a PA pressure waveform and then a PCWP waveform. The cardiac output (CO), which is the amount of blood that the heart pumps per minute, may also be determined during a right-heart and PA catheterization. Pressure measurements may be made before and after administration of intravenous (IV) heart medications. The catheter may need to be repositioned several times to allow for several pressure measurements to be made at each of the different locations A, B, C and D within the heart and PA.

Limitations of conventional PA catheters of this type include:

Pressure measurements are made by a fluid filled pressure sensing catheter

Pressure is transmitted through fluid filled lumen to a remote pressure transducer; pressure measurements are not always accurate.

Pressure is measured at the distal tip only, so pressure can be measured only at one point or location at a time.

Pressure measurements are sensitive to relative positioning and re-positioning of the catheter and pressure transducer, e.g. raising or lowering it relative to the heart in order to set the zero pressure (0 cm H$_2$O) on the transducer.

Kinking or bending of the catheter may dampen the characteristic waveforms seen at each position;

There is time lag (and hysteresis) between pressure being applied to the opening at the tip of the pressure sensing lumen and transmission of pressure through the fluid filled lumen to the remote transducer.

Pullback and repositioning of the catheter for multiple measurements may cause cardiac arrhythmias.

A system and apparatus comprising a multi-sensor catheter for use in cardiology, which may include diagnostic measurements of cardiovascular parameters during right heart and PA catheterization, according to an embodiment will be illustrated and described, by way of example, with reference to a system 2000 comprising a multi-sensor PA catheter 2001, illustrated schematically in FIGS. 5 to 9.

Figure 5:
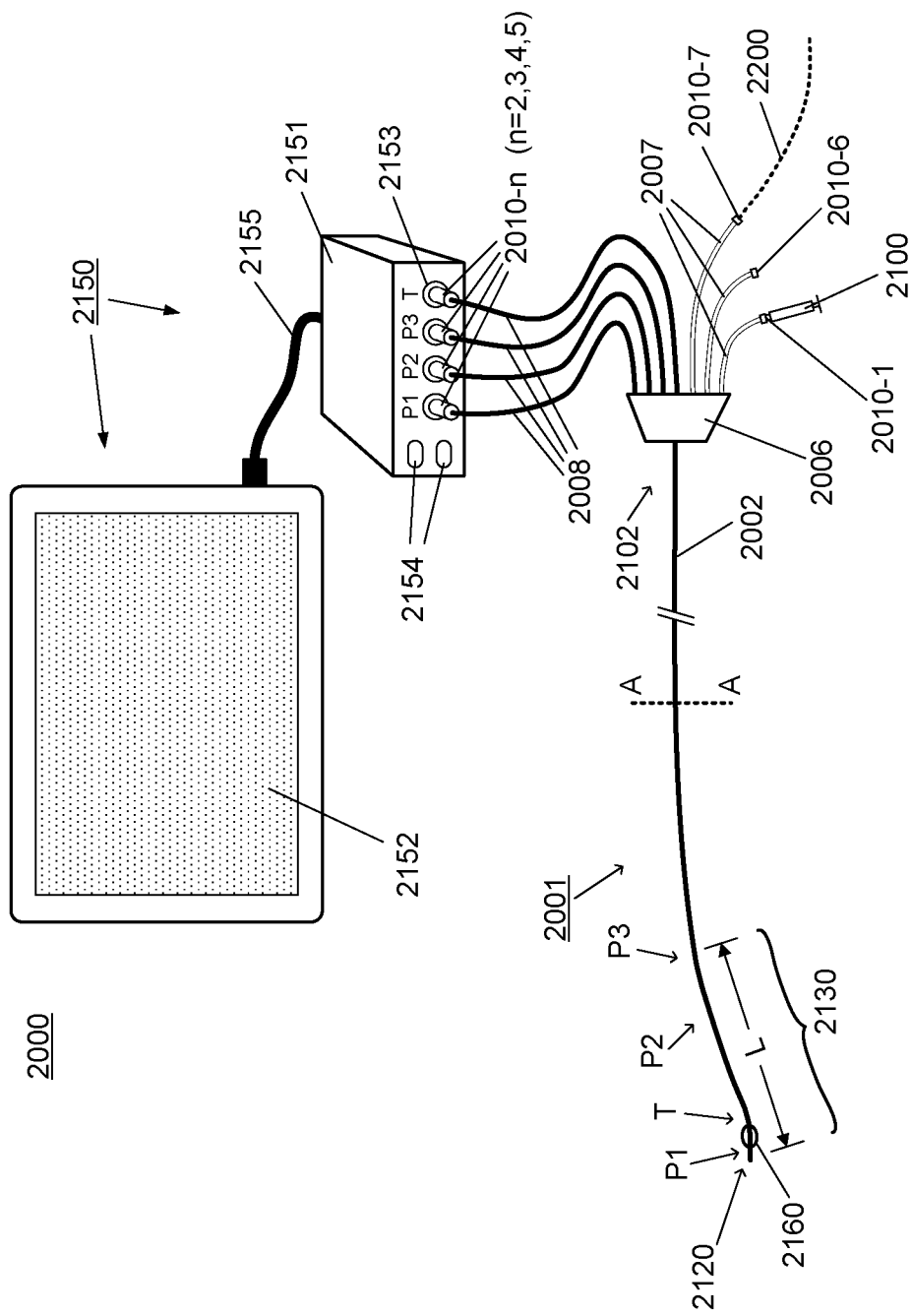
FIG. 5 illustrates schematically a system according to a first embodiment, comprising an apparatus for right heart and PA catheterization comprising a multi-sensor PA catheter, which is optically coupled to a control unit.

Firstly, referring to FIG. 5, this schematic diagram represents the system 2000 comprising an apparatus 2001 comprising a multi-sensor catheter for right heart and PA catheterization procedures, coupled to a control system 2150, which comprises a control unit 2151 and user interface, such as the illustrated touch screen display 2152. The multi-sensor catheter 2001 comprises some components of a conventional PA catheter, including multi-lumen catheter tubing 2002. In the multi-sensor catheter of this embodiment, the catheter tubing comprises seven lumens 2004-1 to 2004-7, as illustrated in the transverse cross-sectional view in FIG. 7, which is a cross-section through A-A of FIGS. 5, 6 and 9. Typically, the catheter tubing 2002 has an outside diameter in the range of about 3-8 French (see Table 1 below for equivalent dimensions in mm and inches), and extends to an atraumatic flexible tip 2120 comprising an inflatable balloon 2160, as shown schematically in FIGS. 5 and 6.

TABLE 1

| French (Gauge) | Diameter (mm) | Diameter (inches) |
|---|---|---|
| 2 | 0.667 | 0.027 |
| 3 | 1.000 | 0.039 |
| 4 | 1.333 | 0.053 |
| 5 | 1.667 | 0.066 |
| 6 | 2.000 | 0.079 |
| 7 | 2.333 | 0.092 |
| 8 | 2.667 | 0.105 |

By way of example, the catheter tubing may typically be about 110 cm in length from the distal tip 2120 to the proximal end, which comprises a connection hub 2006. This length is suitable for introduction of the catheter into the right heart and PA through the superior vena cava (e.g. reached through the subclavian vein or interior jugular vein in the neck, or through the median cubital vein in the arm) or the inferior vena cava (e.g. reached through a femoral vein). For some applications, the catheter length may be shorter, e.g. 60 cm, or longer than 110 cm.

Figure 6:
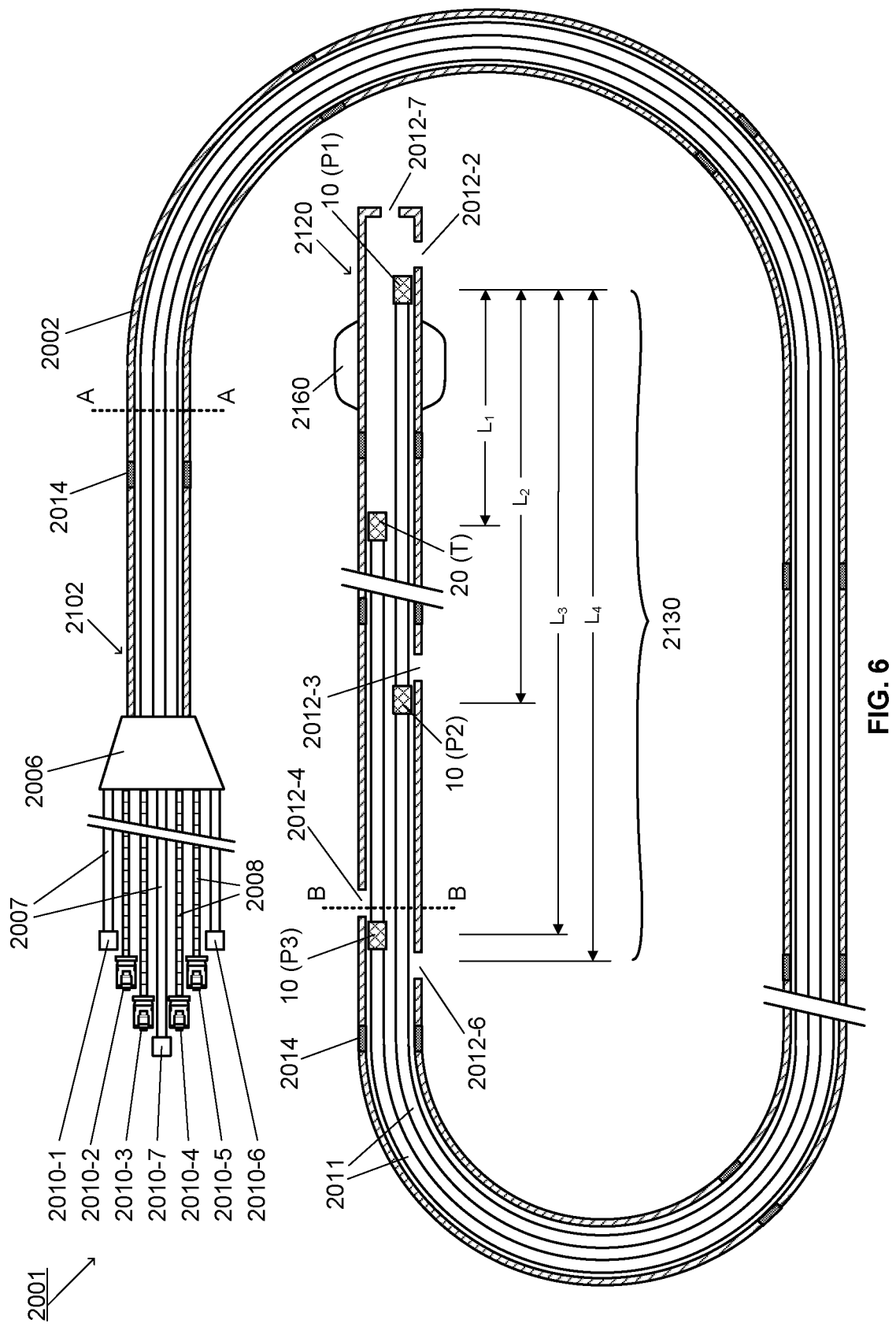
FIG. 6 shows a schematic longitudinal cross-sectional view of an apparatus for right heart and PA catheterization comprising a multi-sensor PA catheter according to the first embodiment.

The PA catheter 2001 differs from a conventional PA catheter, in that, internally, as illustrated schematically in the longitudinal cross-sectional view in FIG. 6, it also contains a multi-sensor arrangement comprising a plurality of optical pressure sensors 10 and an optical temperature sensor 20, and respective optical fibers 2011. The optical sensors 10 and 20 are not externally visible in FIG. 5, so the sensor positions are indicated schematically by P1, P2, P3 for the optical pressure sensors and T for the optical temperature sensor. The sensor positions P1, P2, P3 and T are located along a length L distal end portion 2130, near the distal tip 2120. As illustrated schematically in FIG. 5, the connection hub 2006 provides connection ports 2010-n, where n=1 to 7, for each of the seven lumens. Four of the connection ports, 2010-2, 2010-3, 2010-4, 2010-5 are optical connectors which are coupled via flexible optical connections 2008 through the hub 2006 to the optical fibers and sensors within their respective lumens, i.e. lumens 2004-2, 2004-3, 2004-4, 2004-5 shown in the transverse cross section in FIG. 7. The optical connectors each for the four optical sensors (P1, P2, P3 and T) plug into corresponding optical ports 2153 of the optical controller 2151 shown in FIG. 5.

Figure 7:
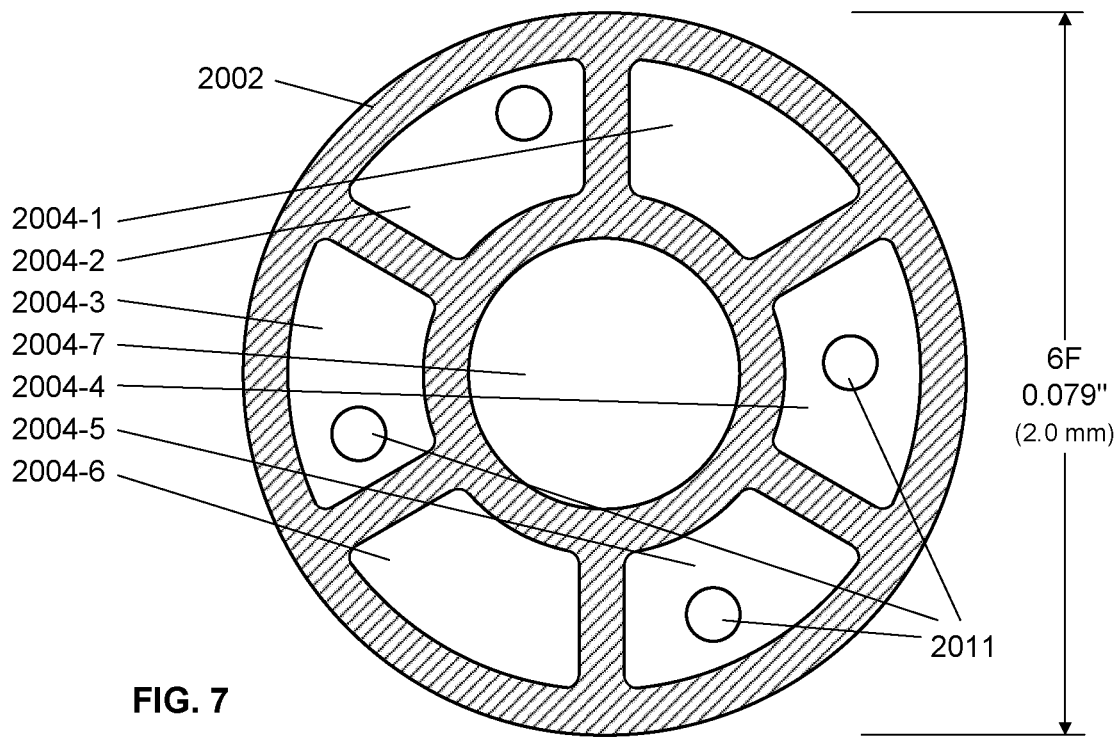
FIG. 7 shows an enlarged axial cross-sectional view of the multi-lumen catheter illustrated in FIGS. 5, 6 and 9 taken through plane A-A of FIGS. 5, 6 and 9.
Figure 8:
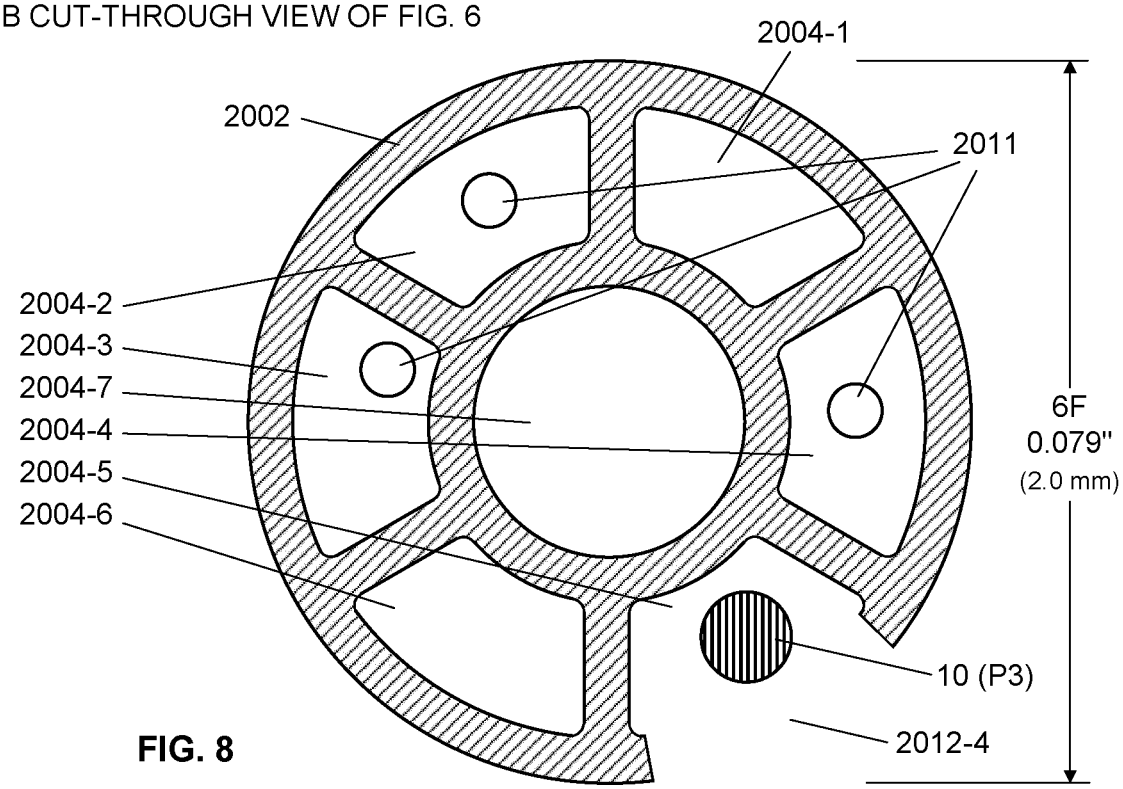
FIG. 8 shows an enlarged axial cross-sectional view of the multi-lumen catheter illustrated in FIG. 6 taken through plane B-B of FIG. 6.

Referring to the schematic longitudinal cross-sectional view shown in FIG. 6, and the transverse cross-sectional view shown in FIG. 7, for simplification of illustration, the internal walls of the lumens 2004-1 to 2004-7 are omitted from FIG. 6 and only the optical fibers 2011 and sensors 10 and 20 are shown within the catheter tubing; elements shown in FIG. 6 are not drawn to scale. Thus, in description of FIG. 6, references to the lumens 2004-1 to 2004-7 are made based on FIG. 7. Also, by way of example, FIG. 7 shows typical dimensions for catheter tubing comprising seven lumens and having an outside diameter of 6 French (0.079 inch/2.00 mm), and for optical fibers 2011 having a diameter of 0.155 mm.

As is conventional, the PA catheter 2001 has an inflatable balloon 2160 connected to a balloon inflation lumen 2004-1 which is coupled through the hub 2006 and flexible tubing 2007, to a balloon inflation/deflation port 2010-1. Another lumen 2004-6 provides for fluid injection or infusion through a fluid injection/infusion port 2010-6 for injection of fluid through an aperture 2012-6 located close to the sensor location P3. A central lumen 2004-7, which has an opening 2012-7 at the distal tip 2120, has an internal diameter which is sized to receive a standard guidewire, such as a 0.025-inch guidewire, to allow for over-the-guidewire directed insertion of the PA catheter. Thus, of the seven ports 2010-n (n=1 to 7), four of those ports 2010-2, 2010-3, 2010-4, 2010-5 comprise standard optical fiber connectors and the other three ports 2010-1, 2010-6 and 2010-7 are standard ports, such as luer fittings, i.e. for attachment of an air filled syringe for balloon inflation/deflation, for fluid injection or for guidewire insertion.

The positioning of the optical sensors 10, 20 within the catheter tubing 2002 is illustrated in more detail in the schematic longitudinal cross-sectional view shown in FIG. 6. There are three optical sensors 10, at sensor locations P1, P2 and P3, for measuring pressure and one optical sensor 20, at sensor location T, for measuring temperature. Each optical sensor 10 and 20 is optically coupled to a respective individual optical fiber 2011. That is, each optical sensor is integral with a sensor end of the fiber, or is bonded to the optical fiber, to provide an optical coupling of the sensor and fiber. Each optical fiber, carrying its sensor at the end, extends through its own individual lumen 2004-2, 2004-3, 2004-4, 2004-5 of the multi-lumen catheter, as illustrated in the transverse cross-sectional view in FIGS. 7 and 8, which are taken through plane A-A and B-B, respectively, of FIG. 6. The central lumen 2004-7 is sized to accept a guidewire, such as a standard 0.025 inch guidewire to facilitate insertion of the catheter. The other six lumens are arranged symmetrically around the central lumen. A first lumen 2004-1 and its port 2010-1 provides for balloon inflation, as is conventional, with a distal opening (2012-1 not visible) coupled to the balloon. The proximal port 2010-1 is coupled via the hub 2006 to lumen 2004-1 via a length of flexible tubing 2007, and the port 2010-1 is typically a luer type fitting for connection to an air-filled syringe (2100 in FIG. 5) for inflation and deflation of the balloon 2160. Second, third and fourth lumens, i.e. lumens 2004-2, 2004-3, 2004-4, each accommodate one of the optical pressure sensors 10 and its optical fiber 2011. Each of these lumens have a respective distal aperture 2012-2, 2012-3, 2012-4, adjacent to the respective sensor locations P1, P2, P3 for fluid contact. A fifth lumen 2004-5 accommodates the optical temperature sensor 20 and its optical fiber 2011. At the proximal end, the optical fibers 2011 for each sensor extend through a length of flexible tubing 2008 from the hub 2006 to the respective optical connector 2010-2, 2010-3, 2010-4, 2010-5. Thus, the fibers are protected within the flexible tubing 2008 to provide a flexible optical connection of a desired length for connection to the control system. The sixth lumen, 2004-6 is provided for fluid injection of a bolus of cold fluid, to allow for flow to be determined by thermo-dilution by detection of temperature changes by optical temperature sensor 20. This fluid injection lumen 2004-6 has a distal opening 2012-6 positioned for delivering fluid to the right atrium, e.g. approximately 30 cm from the distal tip 2120, close to the sensor position P3. When the sixth lumen is not being used for injectate for thermo-dilution measurements, it may alternatively be used for fluid infusion or injection for other purposes. As mentioned above, the central or seventh lumen 2004-7 is provided for a guidewire, if guidewire assisted insertion is required. After withdrawal of the guidewire, optionally this lumen may be used for other purposes, such as blood sampling at the tip of the PA catheter, e.g. for mixed venous oxygen saturation ($SvO_2$) measurements, or for measurement of cardiac output by the method of Fick. If required, markers 2014, such as radiopaque markers, may be provided in the catheter tubing, e.g. near the sensors and at the tip.

As illustrated schematically in FIG. 6, the three optical pressure sensors 10 at sensor positions P1, P2, P3, and the optical temperature sensor 20 at position T, are provided along a length of the distal end portion 2130 spaced by distances $L_1$, $L_2$ and $L_3$ from sensor position P1. P1 is located at or close to the distal tip 2120, distal to the balloon 2160. P2 and P3 are arranged spaced apart lengthwise so that, in use, they can be located, respectively in the RV and the RA, when P1 is positioned in the PA. In use, corresponding apertures 2012-2, 2012-3, 2012-4 near each optical pressure sensor 10 allow for fluid contact with the optical pressure sensors. By way of example, P2 is located at a distance $L_2$ from P1, typically $L_2$ is about 20 cm; and P3 is located at a distance $L_3$ from P1, typically $L_3$ is about 30 cm. That is, the distance between P1 and P2, is about 20 cm and the distance between P2 and P3, is about 10 cm. The location of the optical temperature sensor T is proximal to the balloon and at a distance $L_1$ from P1, where $L_1$ is approximately 4 cm, so that the temperature sensor T is located in the PA when the pressure sensors locations P1, P2 and P3 are positioned, respectively, in the PA, the RV and the RA.

The transverse cross-sectional view shown in FIG. 7 through plane A-A of FIG. 6, illustrates the arrangement of the seven lumens of the catheter tubing of the catheter 2001 of this embodiment. There is a central lumen 2004-7 for a guidewire, e.g. of a suitable diameter to receive a standard 0.025 inch guidewire. As mentioned above, the central lumen may also be used for fluid injection or infusion, or for blood sampling. The other six lumens 2004-1 to 2004-6 are arranged symmetrically around the central guidewire lumen 2004-7. As mentioned above, three of the lumens accommodate the three pressure sensors 10 at locations P1, P2 and P3 and their optical fibers 2011. One of the lumens accommodates the temperature sensor 20 at location T and its optical fiber 2011. One lumen, for example 2004-1, is provided for balloon inflation. The other lumen, for example 2004-6, is provided for fluid injection or infusion. Thus, as shown schematically in the cross-sectional view in FIG. 8, through B-B of FIG. 6, an aperture or orifice 2012-4 is provided adjacent sensor P3 for fluid contact. Correspondingly, as shown in longitudinal cross-sectional view in FIG. 6, an aperture is also provided near each of the other pressure sensors 10 for fluid contact The lumen for fluid injection has an opening 2012-6 that is located proximal to the aperture 2012-4 for P3 by a short distance, e.g. by 1 cm, or a distance $L_4$, of about 31 cm from P1 at the distal tip 2120. The spacings of the three pressure sensors 10 are selected to allow sensor locations P2 to be placed in the RV and sensor location P3 to be placed in the RA when sensor P1 is in the PA, and so that the temperature sensor location T is positioned in the PA for measurement of blood flow in the PA by thermo-dilution.

Referring back to FIG. 5, the proximal part of the apparatus 2001 provides for optical coupling of the proximal end 2102 to the control unit 2151. Four of the proximal ports 2010-2, 2010-3, 2010-4 and 2010-5, for the four optical sensors (P1, P2, P3 and T), comprise a standard type of optical fiber connector, each of which connects to a corresponding optical input/output connector 2153 of the control unit 2151. The control unit 2151 houses a control system comprising a controller with appropriate functionality, e.g. including a processor, data storage, and optical source and optical detector, and it provides a user interface, e.g. a keypad 2154, and touch screen display 2152, suitable for tactile user input, and for graphical display of sensor data. The user interface connection 2155 (e.g. a standard USB cable, or alternatively, a wireless connection) is used to transfer data between the control unit 2151 to the touch screen display 2152. The control unit 2151 and touch screen display 2152 may optionally be integrated within a single housing or module. As illustrated schematically in FIG. 5, each of the optical sensors is connected by an individual optical connector to the control unit. Alternatively, in other embodiments, the proximal ends of the optical fibers for each of the optical sensors may be bundled together and coupled into a single multi-fiber proximal optical connector for connection to a multi-fiber optical port of the control unit. At the proximal end 2102 of apparatus 2001, a hub 2006 couples each lumen of the catheter via a respective length of flexible tubing to an individual proximal port. The other three ports, 2010-1, 2010-6 and 2010-7 comprise standard connections, such as Luer fittings, for attachment of a syringe or tubing. When not in use, the latter ports would typically be supplied with sterile plugs. In use, port 2010-1 is connected to a small air filled syringe 2100 for inflation/deflation of the balloon tip 2160. Port 2010-6 is used for fluid injection or infusion. Port 2010-7 is sized to accept a guidewire 2200, e.g. a standard 0.025 inch guidewire, or this port can be used for blood sampling at the tip of the catheter.

The optical pressure sensors 10 (P1, P2, P3) are preferably Fabry-Perot (FP) Micro-Opto-Mechanical System (MOMS) sensors, such as described by FISO Technologies (E. Pinet, "Pressure measurement with fiber-optic sensors: Commercial technologies and applications" 21st International Conference on Optical Fiber Sensors, edited by Wojtek J. Bock, Jacques Albert, Xiaoyi Bao, Proc. of SPIE Vol. 7753, (2011)). These optical pressure sensors comprise an optical fiber having a FP MOMS sensor at the sensor end of the fiber for sensing pressure. By way of example, for standard diameter optical fibers, each fiber (e.g., fibers 2011 in FIGS. 7 and 8) has a diameter of 0.155 mm (0.006 inch) and each optical pressure sensor (e.g., sensors 10 in FIG. 8) has a diameter of 0.260 mm (0.010 inch).

For measurement of flow by thermo-dilution, the optical temperature sensor 20 (T) may, for example, be a GaAs (Gallium Arsenide) fiber optic temperature sensor, as described by FISO technologies (E. Pinet et al., "Temperature fiber-optic point sensors: Commercial technologies and industrial applications", MIDEM Conference Proceedings, Sep. 29-Oct. 1, 2010, Radenci, Slovenia).

A typical material for fabrication of the multi-lumen catheter is a flexible polymer, such as, 4033 Pebax® (a Polyether block amide or PEBA, or other suitable thermoplastic elastomer (TPE)), which has regulatory approval for fabrication of conventional PA catheters. The wall thickness of the tubing may be ~0.005 inch. The guidewire lumen has a diameter, for example, of 0.029 inch to accommodate a standard 0.025 inch guidewire. Conventional coloring of the standard ports may be provided. A different color coding may be provided for the optical ports to facilitate quick recognition and connection to correspondingly color coded ports of the optical controller. As illustrated schematically the transverse cross-sectional views in FIGS. 7 and 8, sensors and fibers of these dimensions can be accommodated within catheter tubing 2002 having an outside diameter of 6 French (0.079 inch or 2.0 mm—see Table 1).

For some applications a larger diameter catheter, e.g. 7 French, may be acceptable.

For smaller optical fibers, e.g. 0.100 mm fibers, and smaller diameter sensors, if a guidewire lumen is not required, or if the guidewire to be used is smaller than 0.025 inch, e.g. 0.018 inch, the dimensions of the lumens and the outside diameter of the catheter tubing may be reduced in size accordingly, e.g. to 5 French or less.

It is preferable that the arrangement of the lumens has rotational symmetry about the longitudinal axis, and the wall thickness of each lumen is selected to provide the required mechanical characteristics, such as an appropriate degree of flexibility and stiffness, with symmetric torque characteristics along its length. For over the guidewire insertion, a more flexible catheter may be selected. For insertion without a guidewire, a stiffer catheter may be desirable. For example, while the catheter requires sufficient flexibility to traverse from the RA into the RV and then be guided into the PA, it is also desirable that the catheter has sufficient stiffness or rigidity (i.e. is not too floppy) to withstand turbulent blood flow within the ventricles, to withstand distortion or kinking, and to maintain a minimum bend radius of the optical fibers.

When the optical pressure sensors are FP MOMs sensors, they measure pressure at point locations of the sensor at the end of the fiber, i.e. pressure exerted on the FP membrane, and optical measurements are based on interference measurements, i.e. frequency shifts, rather than amplitude measurements. Blood pressure measurements are made with greater accuracy and reliability compared to conventional pressure sensing with a fluid filled catheter and an external pressure transducer. FP MOMS sensors can provide significantly more accurate pressure measurements, with minimal drift, compared to electrical pressure sensors, such as piezoelectric sensors. Optical pressure sensors avoid the need for multiple long thin electrical connections, which not only have significant electrical drift, but are subject to cross-talk and electro-magnetic interference. For similar reasons, it is also preferable that for measurement of flow by thermo-dilution or thermo-convection, the temperature sensor is preferably also an optical sensor rather than an electrical sensor. For example, for thermo-dilution measurements, the temperature sensor may be a fiber optic sensor which measures temperature based on the temperature dependence of a GaAs sensor at the tip of the fiber, i.e. a temperature dependent shift in the peak wavelength of light reflected from the sensor.

Figure 9:
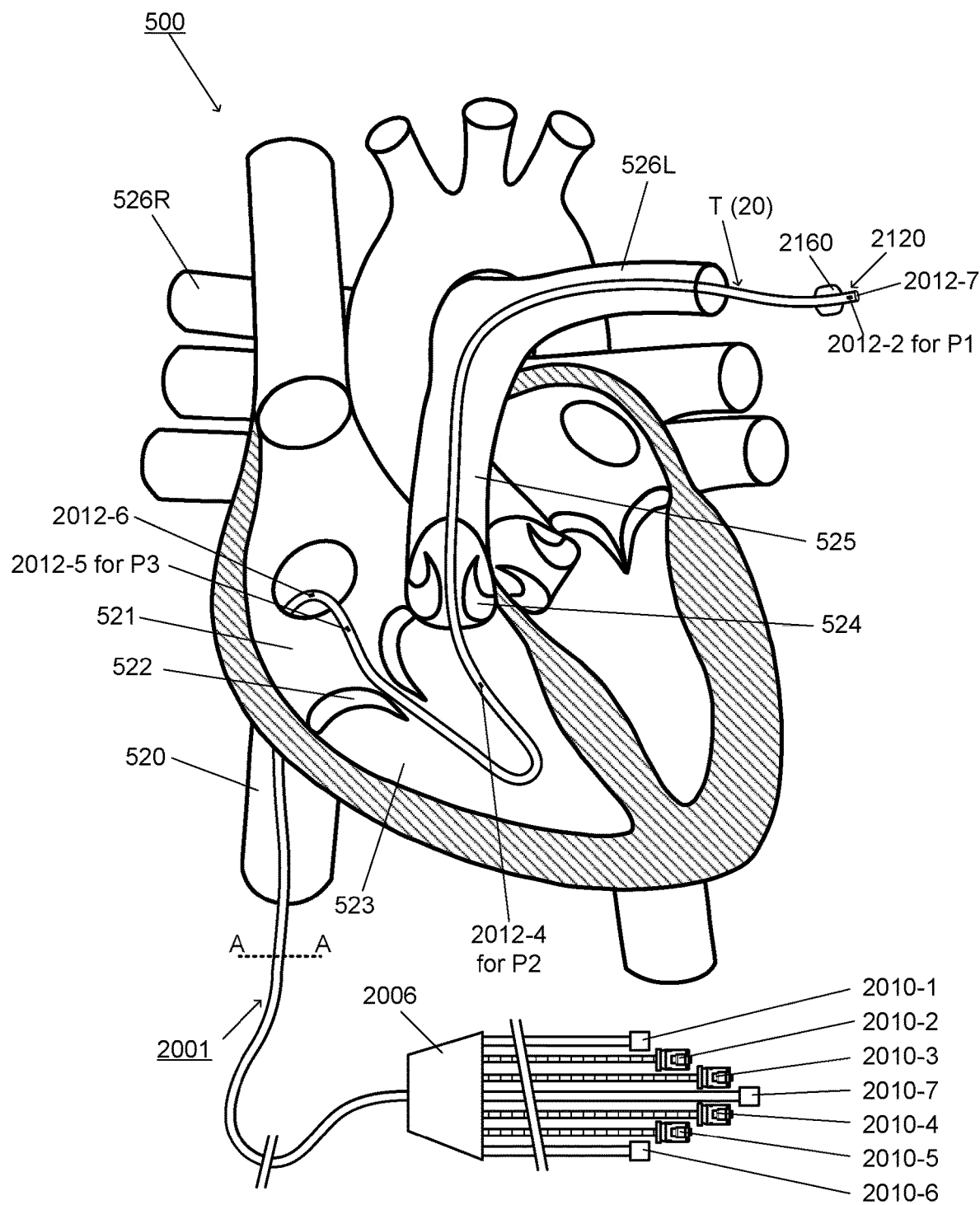
FIG. 9 shows a schematic partial cross-sectional diagram of a human heart to illustrate placement of the multi-sensor PA catheter of the first embodiment within the right heart and PA for diagnostic measurements of hemodynamic parameters, including concurrent measurements of blood pressure in the RA, in the RV, in the PA and the PCWP.

FIG. 9 provides a schematic diagram of the heart 500 to illustrate placement of the multi-sensor catheter 2001 of the first embodiment during a right heart and PA catheterization procedure to measure pressure concurrently in the right atrium 521, right ventricle 523 and PA 525. In this example, the multi-sensor catheter 2001 is introduced into the heart through the inferior vena cava 520, through the right atrium 521, through the tricuspid valve 522 into the right ventricle 523, through the pulmonic valve 524 and into the PA 525. The tip 2120 of the catheter extends into the left branch 526L of the PA. The aperture 2012-2 for pressure sensor P1, which is distal to the balloon 2160 is located in the left branch of the PA 526L. The temperature sensor T is also in the left branch of the PA 526L, proximal to the balloon. Aperture 2012-3 for pressure sensor P2 is located in the right ventricle 523. Aperture 2012-4 for pressure sensor P3 is located in the right atrium 521. The proximal fluid injection port 2012-6 is also located in the right atrium 521. Ports 2010-1 to 2010-7 are provided at the proximal end of the multi-sensor catheter 2001, as described above. Thus, when the optical connectors 2010-2, 2010-3, 2010-4, for the three optical pressure sensors P1, P2 and P3, and optical connector 2010-5 for the optical temperature sensor T are connected to the optical control system, the pressure measurements in the RA, RV and PA can be made concurrently. Also, the optical temperature sensor T can be used for measurement of flow by a conventional thermo-dilution technique.

For some applications, a temperature sensor for measurement of flow by thermo-dilution may not be required, and it may be omitted.

Figure 10:
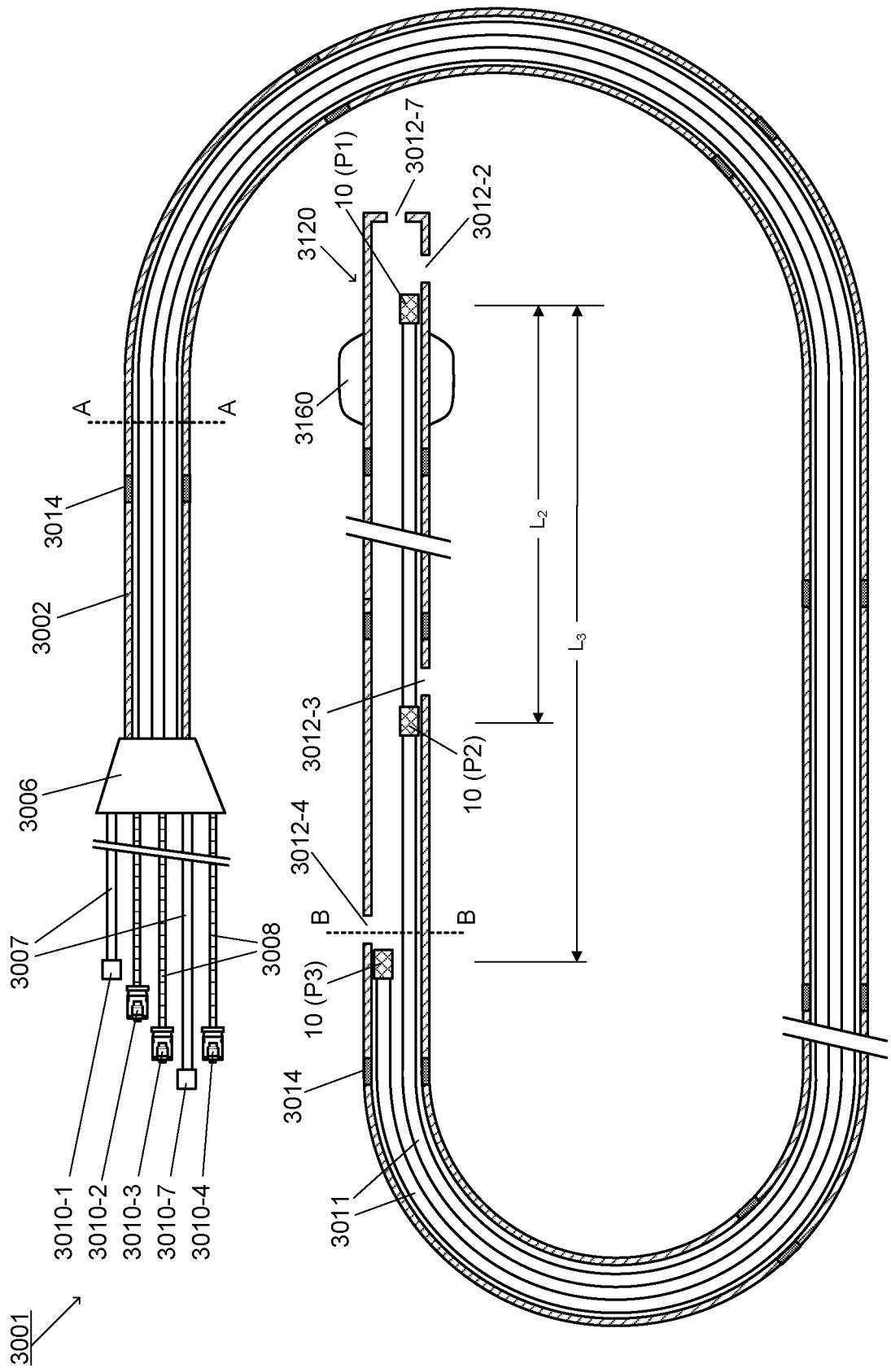
FIG. 10 shows a schematic longitudinal cross-sectional view of an apparatus for right heart and PA catheterization comprising a multi-sensor PA catheter according to the second embodiment.
Figure 11:
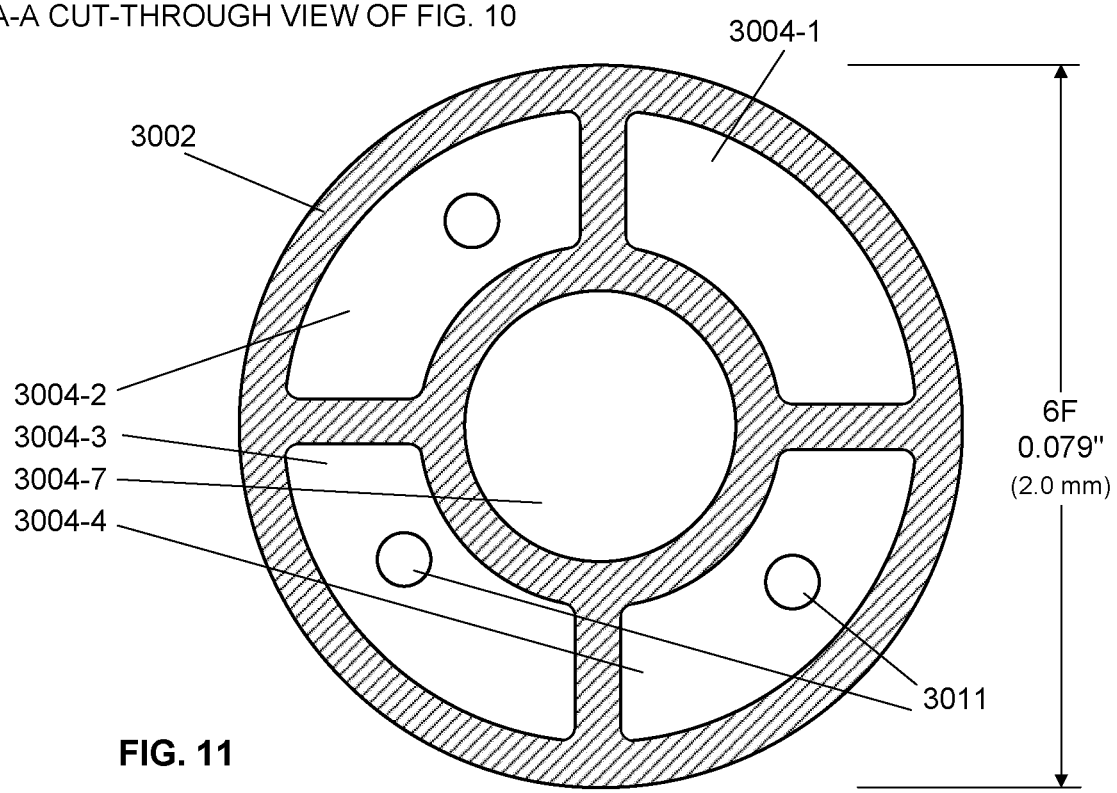
FIG. 11 shows an enlarged axial cross-sectional view of the multi-lumen catheter illustrated in FIG. 10 taken through plane A-A of FIG. 10.
Figure 12:
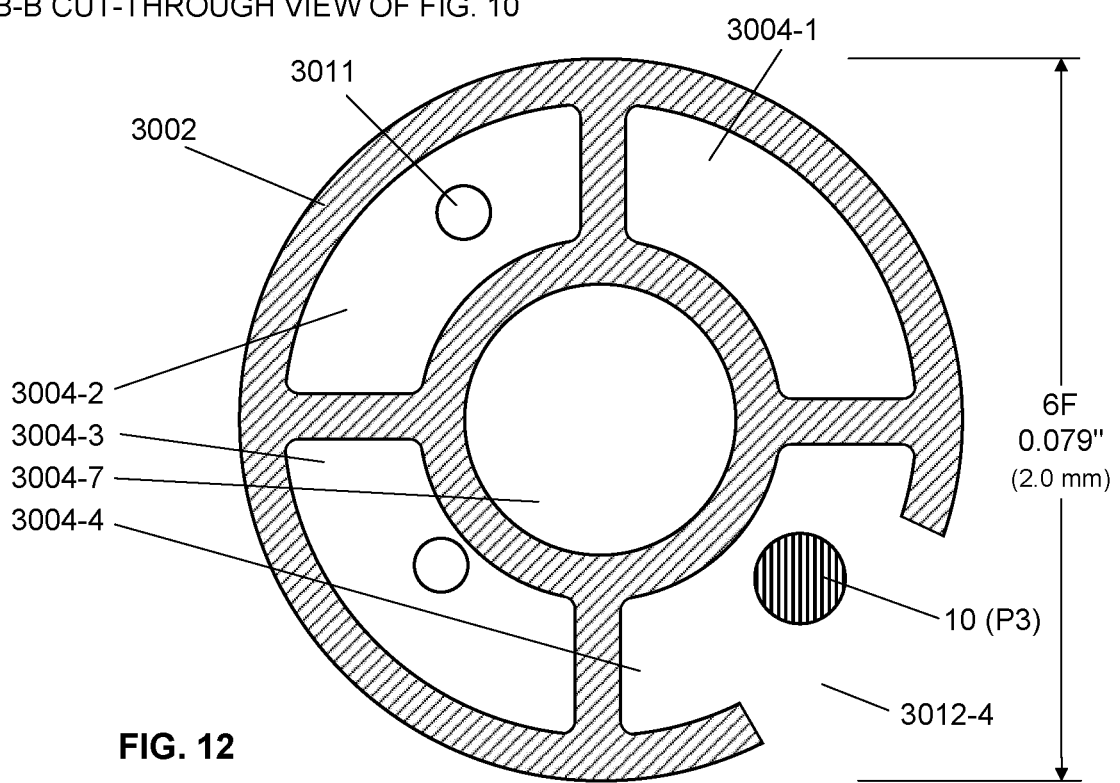
FIG. 12 shows an enlarged axial cross-sectional view of the multi-lumen catheter illustrated in FIG. 10 taken through plane B-B of FIG. 10.

A multi-sensor PA catheter 3001 of a second embodiment is illustrated in FIGS. 10, 11 and 12. As shown in a longitudinal cross-sectional view of FIG. 10, in this embodiment, the multi-sensor catheter comprises three optical pressure sensors 10, at sensor locations similar to those of the multi-sensor PA catheter 2001 of the first embodiment, but there is no temperature sensor. As illustrated in the transverse cross-sectional views in FIGS. 11 and 12, in this simplified version of the multi-sensor PA catheter, the catheter tubing 3002 comprises five lumens, i.e. a first lumen 3004-1 for balloon inflation; three lumens 3004-2, 3004-3, 3004-4, one for each of the three pressure sensors 10 and its respective optical fiber 3011; and the central lumen 3004-7 is provided for a guidewire, and/or for blood sampling, as described for the multi-sensor PA catheter of the first embodiment. As shown in FIG. 10, the optical fibers 3011 for the optical pressure sensors 10 are connected from the respective lumens, through connection hub 3006, and via flexible tubing 3008 to respective ports 3010-2, 3010-3 and 3010-4. Ports 3010-2, 3010-3, 3010-4 comprise optical connectors for the three optical pressure sensors 10 in the second, third and fourth lumens 3004-2, 3004-3, 3004-4. Each of the three lumens 3004-2, 3004-3, 3004-4 has a respective aperture 3012-2, 3012-3 and 3012-4 for fluid contact with the respective optical pressure sensors 10. Port 3010-1 connects via tubing 3007 to the hub 3006 and the first lumen for inflation/deflation of the balloon 3160. Port 3010-7 connects via tubing 3007 to the central lumen which has an opening 3012-7 at the distal tip 3120 for a guidewire, or for blood sampling at the tip of the catheter. Radiopaque markers 3014 are provided along the length of the catheter tubing to assist in positioning the sensors 10 within the heart. As illustrated, by way of example, in FIGS. 11 and 12, the catheter tubing has an external diameter of 6 French and provides a central lumen 3004-7 having an inside diameter which can accept a guidewire, e.g. a standard 0.025 inch guidewire, and four lumens arranged symmetrically around the central lumen. That is, one lumen for balloon inflation, and three lumens for three optical fibers of 0.155 mm diameter and FP-MOMS optical pressure sensors of 0.260 mm diameter. The outside diameter of the PA catheter tubing may be reduced if smaller diameter optical fibers and sensors are used, or for use with a smaller diameter guidewire.

In comparing the multi-sensor catheters of the first and second embodiments, comprising 7 lumens and 5 lumens respectively, it will be appreciated that the dimensions of each of the catheters, such as the external diameter, the number of lumens and the thicknesses of the internal walls of the catheter defining each lumen are described by way of example only. As mentioned above, smaller optical sensors and smaller optical fibers may be accommodated within smaller lumens, to provide a catheter having a smaller outside diameter. This may be desirable for some applications. The material from which the catheter is made, and the wall thicknesses defining the lumens, may be selected to provide the catheter with a required stiffness or flexibility, and size.

In other alternative embodiments, when the catheter is to be flow directed by the balloon tip, and introduction over a guidewire is not required, the guidewire lumen may be omitted.

For some applications, for example for pediatric or neonatal use, a significantly smaller diameter catheter may be required, e.g. 3 French. Correspondingly, the spacings of the optical pressure sensors would be closer together, i.e. matched to the smaller dimensions of the chambers of a patient's heart, for placement of one sensor in the RA, one in the RV and one in the PA. In such a case the guidewire lumen may be omitted so that three pressure sensors can be accommodated within a multi-lumen catheter of the required diameter. While three pressure sensors are desirable for concurrent measurements of RA, RV and PA pressure waveforms, when a guidewire lumen is required for a smaller diameter catheter, it may only be possible to accommodate two optical pressure sensors. In this arrangement, the two sensors would be spaced apart so that initially, one sensor can be positioned in the RA and one in the RV for concurrent measurement of RA and RV pressure waveforms, and then subsequently the catheter would be advanced to position one sensor in the RV and one in the PA for concurrent measurement of RV and PA pressure waveforms, and for RV and PCWP pressure waveforms.

The lengthwise spacings ($L_2$ and $L_3$) of the optical pressure sensors at locations P1, P2 and P3 described with respect to the multi-sensor catheters of the first and second embodiments, i.e. for measurement of pressure waveforms concurrently in the RA, RV and PA refer to typical spacings required for an adult human heart, where the distance from the RA to the RV is about 10 cm and the distance from the RV to the PA, in a region downstream of the pulmonic valve, is about 10 cm. The PCWP position is typically a further 10 cm into one of the right or left branches of the pulmonary artery, i.e. about 20 cm from the RV. Thus, to position P1 in the PA near the wedge position, P2 in the RV, and P3 in the RA, $L_2$ is about 20 cm and $L_3$ is about 30 cm. If a temperature sensor is included, the location of the temperature sensor T is typically positioned between P1 and P2, spaced a distance $L_1$ from P1, for measurement of blood flow within the PA, where $L_1$ is e.g. about 4 cm to 10 cm. For pediatric and neonatal use, i.e. for smaller sized hearts, the spacings of the sensors would be reduced accordingly.

While it is envisaged that multi-sensor catheters for right heart and PA catheterization may comprise more than three optical pressure sensors, there is a practical limit to how many sensors can be accommodated within a multi-lumen catheter of a particular outside diameter.

Since multi-sensor PA catheters are intended as disposable, single use catheters, in practice, the number of optical sensors may also be limited by component costs and fabrication costs. Currently, standard diameter optical fibers and optical pressure sensors are lower cost than smaller diameter optical fibers and optical pressure sensors. Since each pressure sensor is in an individual lumen of the multi-lumen catheter, the available space for each lumen is also limited by the wall thickness and tolerances for each lumen of a multi-lumen catheter. As described herein, it is currently feasible to manufacture a multi-sensor PA catheter with three optical pressure sensors and one optical temperature sensor, within a 6 French multi-lumen catheter. Use of smaller fibers and sensors or smaller guidewire may allow the diameter to be reduced to 5 French or less.

In a multi-sensor catheter of yet another embodiment, instead of three optical pressure sensors and one optical temperature sensor, e.g. as described for the first embodiment, it may be desirable to have four optical pressure sensors to enable concurrent pressure measurements in the right atrium, in the right ventricle, in the PA near the pulmonic valve and also in a branch of PA for measurement of the PCWP.

For example, if a temperature sensor is not required for blood flow measurements, for example where blood flow is measured by an alternative technique, e.g. by the Fick method, a fourth optical pressure sensor may be provided instead of the optical temperature sensor, so that the multi-sensor catheter can be introduced so as to position one sensor in the RA, one sensor in the RV, one sensor in the PA, and one sensor for measuring PCWP when the balloon is inflated. By way of example, in such an arrangement, four pressure sensors P1, P2, P3 and P4 are spaced at intervals of ~10 cm, i.e. the distance P1 to P2 ($L_1$) is 10 cm, P1 to P3 ($L_2$) is 20 cm, and P1 to P4 ($L_3$) is 30 cm.

This arrangement may be desirable for longer term monitoring of pressure waveforms in the RA, RV, PA, as well PCWP pressure waveforms. That is, the catheter may be positioned in a fixed and stable location, to enable observation of pressure waveforms at each sensor location over an extended time period, e.g. for ICU patients requiring monitoring over several days or more.

Alternatively, where it is not feasible to accommodate an optical temperature sensor as well as the desired number of optical pressure sensors, or for cost reasons, a conventional small sized, low cost, electrical flow sensor, i.e. a thermistor, may be used, with conventional electrical connections to the control system.

In the embodiments described above, radiopaque markers may be provided near the balloon, and optionally near each sensor, to assist in locating the tip and positioning the sensors in use, i.e. using conventional radio-imaging techniques, when introducing the guidewire and positioning the pressure sensors in the right atrium, right ventricle and PA. The radiopaque markers typically comprise a suitable heavy metal e.g. barium, tantalum, gold or platinum. Alternatively, markers are provided at regular intervals, e.g. at 10 cm intervals along the length of the catheter tubing as is conventional for PA catheters.

Preferably that the optical fibers have some freedom to move or slide within the lumen when the catheter is flexed. The fibers are of the appropriate length so that the sensors at the sensor end (distal end) of the fibers are appropriately positioned at sensor locations in the distal end portion of the catheter. Each of fibers may be secured near the proximal end, e.g. by adhesive bonding where they pass through the hub. Each fiber may also be secured in its lumen, near the sensor location, e.g. by injection of a medical grade adhesive through the wall of the lumen.

If required, in use, the lumens containing the optical fibers and sensors may be flushed with fluid, e.g. saline solution, to remove air from the catheter lumens. Alternatively, an adhesive, or a medical grade gel, may serve to plug the lumen each side of the aperture surrounding the optical sensor, while leaving the sensor exposed for fluid contact. For example, a bolus of medical grade adhesive may be injected through the tubing to secure the fiber near each sensor and to plug the lumen around the fiber. Similarly, the adhesive may also be injected into the lumen distal to the aperture. Also, if required, components of the multi-sensor catheter may be coated to reduce blood clotting, for example, if the multi-sensor catheter is to be left in place for an extended period.

The optical pressure sensors 10 are preferably Fabry-Perot Micro-Opto-Mechanical-Systems (FP MOMS) pressure sensors. As an example, a suitable commercially available FP MOMS pressure sensor is the Fiso FOP-M260. These FP MOMS sensors meet specifications for an appropriate pressure range and sensitivity for blood pressure measurements. They have an outside diameter of 0.260 mm (260 µm). Typically, they would be attached and optically coupled (i.e. integral with or bonded to) to a sensor end of an optical fiber with an outside diameter of 0.100 mm (100 µm) to 0.155 mm (155 µm). Optical fibers and FP MOMS sensors of smaller diameter tend to be more expensive, and may be used, when appropriate.

The optional optical flow sensor 20 may comprise an optical thermo-dilution or an optical thermo-convection flow sensor, e.g. as described in U.S. patent application Ser. No. 14/354,588.

For operation of the optical sensors, the optical output ports 2010-2, 2010-3, 2010-4, 2010-5 couple to the respective optical ports of the control unit 2151 (e.g. see FIG. 5) for controlling operation of the optical sensors 10 and 20. The flexible tubing 2008 surrounding each of the optical fibers extends between the hub 2006 and the optical connector of the control unit to provide a flexible optical coupling from the hub 2006 to the control unit 2151. This tubing is provided to protect the optical fibers and can have any appropriate diameter and flexibility. Since the catheter is intended for single use only, preferably the optical connectors are standard low-cost optical connectors. Similarly, the flexible tubing, and other connectors for the other ports are preferably standard materials and components, such as luer fittings or other medical standard fluid ports and electrical connectors, as appropriate, which can be sterilized, and so that the multi-sensor catheters can be provided in single-use sterile packaging, using conventional standard processes for medical devices.

For protection of the sensors during assembly, it may be preferred to insert optical fibers and optical sensors through the respective lumen from the distal end of the catheter and subsequently form the optical connector at the proximal end, and then close the lumen at the distal tip. On the other hand, when the optical connector is pre-formed at the proximal end of the sub-assembly before insertion, the sensor end of the sub-assembly is inserted into the catheter from proximal end of the respective lumen. In either case, it is preferable that the catheter lumens have smooth rounded surfaces, with non-stick internal surfaces, i.e. to avoid sharp edges, so that the sensors and optical fibers can slide smoothly into their catheter lumen without catching on sharp edges or corners, to avoid mechanical damage to the sensors or optical fibers. However, in use of the multi-sensor catheter, it is preferable that the fibers are fixed at the proximal end only of the catheter tubing so that the fibers have some freedom to move or slide within the lumens when the catheter is flexed. If required, the optical fibers may also be adhesively bonded near the aperture to secure the sensor at the appropriate sensor location.

As mentioned above, it is desirable that the multi-sensor PA catheter has mechanical characteristics, such as stiffness and flexibility, similar to a standard PA catheter. The optical fibers and optical sensors do not add significant stiffness to the catheter, and thus these characteristics are primarily determined by the type of material and wall thickness used for the multi-lumen catheter tubing.

Other factors for consideration are: regulatory requirements for medical devices, ease of use and safety. For these reasons, it is desirable that the materials for fabrication of a multi-sensor PA catheter are based on a conventional tried and tested PA catheter or other medical device, i.e. based on a predicate device structure which has regulatory approval and which is fabricated with materials and components which already have FDA and/or CE mark regulatory approval.

It will be appreciated that in alternative embodiments or variants of the multi-sensor catheters of the embodiments described in detail above, different combinations of one or more features disclosed herein, and features disclosed in the related patent applications referenced herein, may provide multi-sensor catheters of further alternative embodiments.

As disclosed herein, the cardiologist is offered multi-sensor catheters which have particular application for right heart and PA catheterization. These multi-sensor catheters are configured for monitoring and diagnostic measurements of hemodynamic parameters, including concurrent measurement of blood pressure within the RA, RV and PA.

Control System and Graphical Display of Pressure Waveforms and Associated Hemodynamic Parameters.

Figure 13:
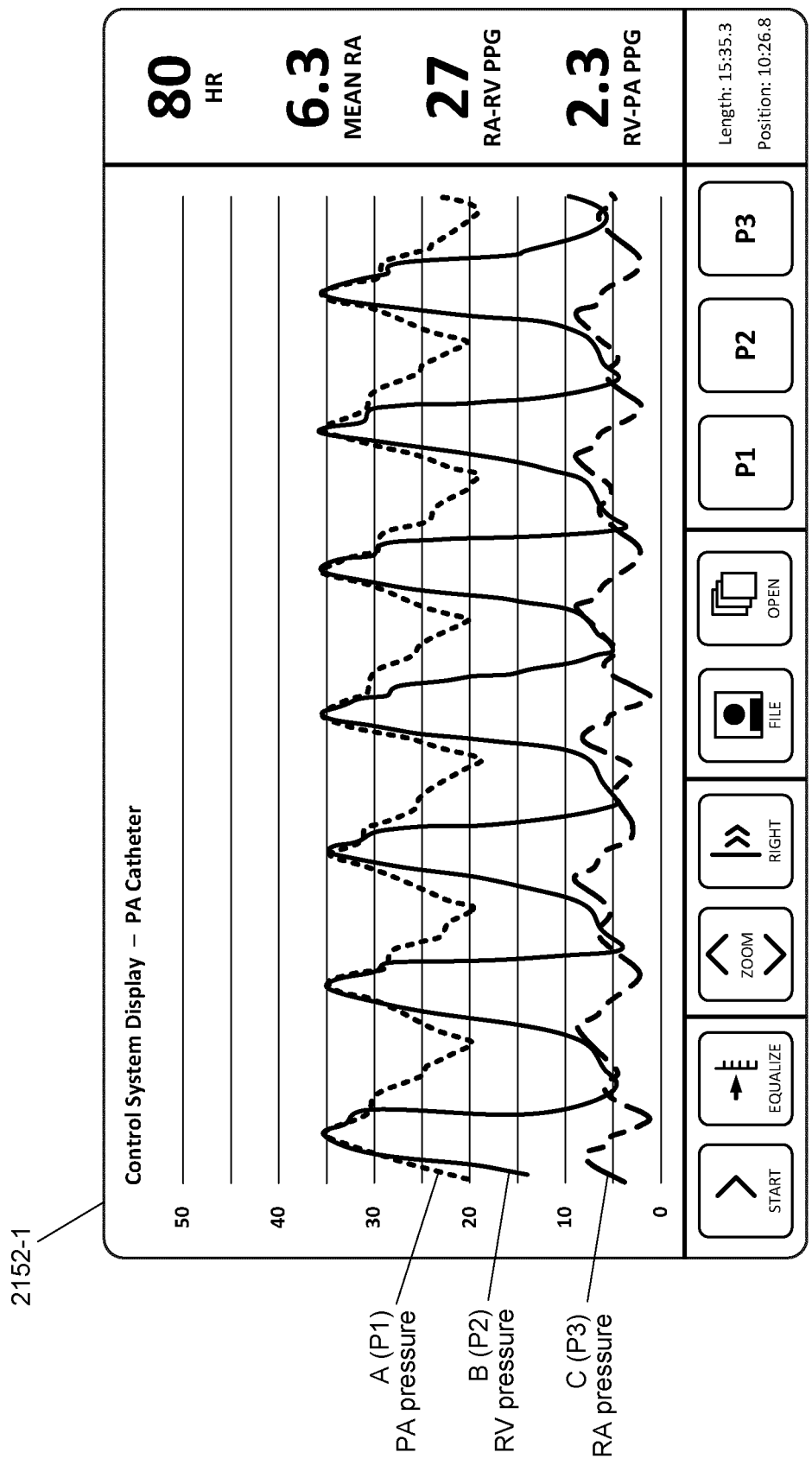
FIG. 13 illustrates schematically a graphical display of the control system showing three concurrent blood pressure waveforms from: A. sensor position P1 in the pulmonary artery (balloon deflated); B. sensor position P2 in the right ventricle; and C. sensor position P3 in the right atrium; together with selected numeric data comprising hemodynamic parameters derived from the pressure waveforms.
Figure 14:
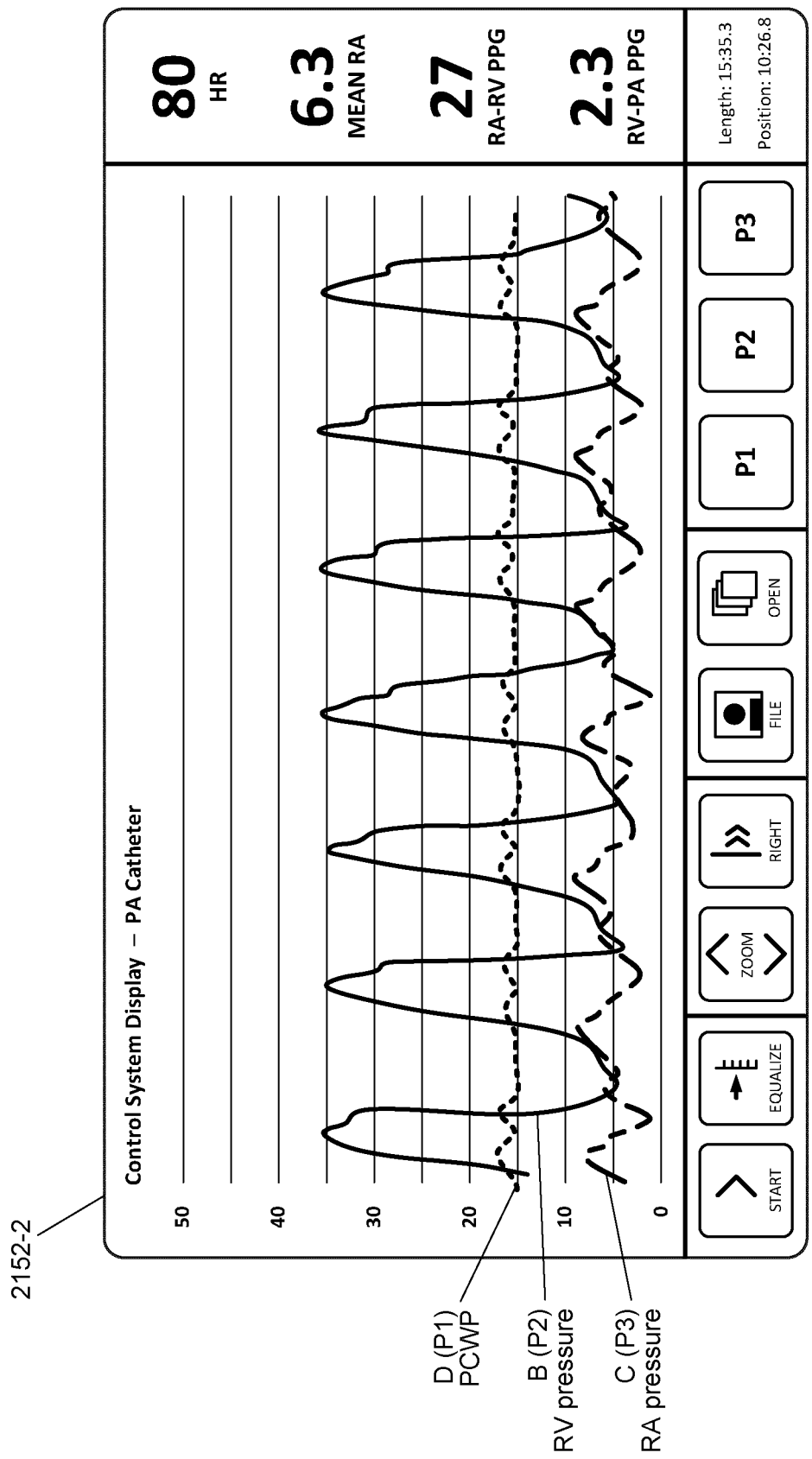
FIG. 14 illustrates schematically a graphical display of the control system showing three concurrent blood pressure waveforms from: D. sensor position P1 in the pulmonary capillary wedge position with the balloon inflated; B. sensor position P2 in the right ventricle; and C. sensor position P3 in the right atrium; together with selected numeric data comprising hemodynamic parameters derived from the pressure waveforms.

Referring to the control system, which was described above with reference to FIG. 5, and as described in the above referenced related patent applications, it will be apparent that the control system may be used with multi-sensor catheters and multi-sensor guidewires for concurrent blood pressure measurements at each pressure sensor location, using, two, three or more optical pressure sensors. Optionally, for flow measurements, the multi-sensor catheter or guidewire is further equipped with an optical or electrical flow sensor. The control system comprises a light source and detector and an optical interface for coupling, via respective input/output ports, to each of the optical fibers and optical sensors of the multi-sensor catheter or guidewire. The control system also comprises data storage and processing means configured for processing optical data indicative of pressure values and optionally, optical or electrical data indicative of flow velocity values. For use with multi-sensor catheters and multi-sensor guidewires, for example, the multi-sensor catheter disclosed herein having three optical pressure sensors, and an optional optical flow sensor, the control system would have a corresponding number of signal processing channels with optical inputs for each of the optical sensors. The signal processing elements for each channel may be referred to as a signal conditioning unit. For measuring blood pressure and flow within the heart and blood vessels, in particular for measuring intravascular or transvalvular blood pressure gradients, the processing means is further configured for graphically displaying pressure data, and optionally flow velocity data, comprising a plurality of blood pressure waveforms, i.e. a pressure waveform from each optical pressure sensor. The concurrent blood pressure waveforms for each of the optical sensors may be displayed for one or more time intervals, and during one or more cardiac cycles. Preferably, the processing means is further configured to derive hemodynamic parameters from the blood pressure data, and optionally from flow velocity data, and display numeric values of the parameters as well as display the pressure waveforms from each sensor. By way of example only, some schematic representations of pressure waveforms and associated numeric data, for a patient with a healthy or normally functioning heart, are shown in FIGS. 13 and 14. In practice, pressure waveforms and pressure values vary from patient to patient and may be dependent on a number of factors, such as, whether or not the patient has a healthy or diseased heart, or other conditions that may affect functioning of the heart. Skilled medical practitioners will recognize characteristic variations in each pressure waveform and associated pressure values, indicative of e.g. valvular stenosis or other patient physiology. Advantageously, in use of a multi-sensor catheter, concurrent pressure measurements from multiple optical pressure sensors enable the cardiologist to directly compare multiple pressure waveforms, in real-time, the RA, RV and PA/PCWP.

As an example, FIG. 13 represents a graphical display 2152-1 showing three blood pressure waveforms from a three sensor PA catheter: A. pressure sensor location P1 in the pulmonary artery; B. pressure sensor location P2 in the right ventricle; and C. pressure sensor location P3 in the right atrium. Pressure units are displayed in mmHg. Optionally, it may be desirable to select and display one or multiple pressure waveforms and related parameters in different formats. For example, during right heart and pulmonary artery catheterization with a multi-sensor catheter as disclosed herein, in addition to displaying concurrent blood pressure waveforms from each the right atrium, right ventricle and pulmonary artery, a plurality of numeric values, such as, peak pressures, mean pressures, peak-to-peak (PK-PK) pressure differentials for each curve, and pressure differentials or gradients between the right atrium and right ventricle, and between the right ventricle and pulmonary artery may be displayed in real time. For example, as illustrated schematically by the numeric data to the right of the graphical display shown in FIG. 13, numeric data selected for display may include the mean pressure of the RA, systolic/diastolic pressure for RV/PA, a peak-to-peak gradient (PPG) for RV to PA, a PPG for RA to RV, and heart rate HR. As is conventional, the user interface may include a number of buttons or keys, such as shown at the bottom of the display in FIG. 13, e.g. to select parameters for display, change display modes, and input identification. FIG. 14 represents a graphical display 2152-2 for three pressure waveforms, similar to that shown in FIG. 13, except that waveform A for the PA pressure is replaced with waveform D for the pressure sensor location P1 is in the pulmonary capillary wedge position with the balloon inflated.

In one embodiment, the control system comprises a signal processing unit for receiving optical data and optionally electrical data, from a multi-sensor catheter or guidewire. The signal processing unit is coupled by a data connection to a general purpose computer system, which may be personal computer (PC), such as a laptop or tablet PC, comprising processing means, i.e. one or more processors and a computer program product, embodied in a non-transitory computer readable medium storing instructions, in the form of code, for execution by the processing means. The computer program product is, for example, a software application comprising instructions for execution in a processor of the tablet PC for receiving or retrieving data, and displaying a plurality of concurrent pressure waveforms from the optical pressure sensors, and for computing, and displaying in real-time, associated hemodynamic parameters.

For example, the tablet PC is configured for graphically displaying pressure data, and optionally flow velocity data, e.g. comprising a plurality of blood pressure waveforms. The concurrent blood pressure waveforms for each optical sensor may be displayed for one or more time intervals, and during one or more cardiac cycles. The processing means is further configured to derive and display hemodynamic parameters from the blood pressure data. For example, during right heart and pulmonary artery catheterization with a multi-sensor catheter as disclosed herein, in addition to displaying blood pressure waveforms from pressure sensors in one or more of the right atrium, right ventricle and pulmonary artery, a selected plurality of numeric values such as peak pressures, mean pressures, peak to peak pressure differentials for each curve, and pressure differentials or gradients between the right atrium and right ventricle, and between the right ventricle and pulmonary artery can be displayed in real time.

As is conventional, the system may comprise a user interface, such as a keyboard or touchscreen, to allow the operator to select from available information which waveforms or parameters are to be displayed. The interface may allow the operator to input user data such as patient identification, and data interfaces may be provided to output data to other devices or systems, or receive data from other sources, such as from other sensors or monitoring systems, which are typically used in an ICU or OR. For example, in a cardiac catheterization laboratory, the control system for a multi-sensor catheter or guidewire may be coupled to, or part of, a computing system controlling other equipment, and which is equipped with one or more large screen displays close to the operating table, and other remote displays in a monitoring area. The latter are used to display various forms of data, sequentially, concurrently, or on demand. Such data may include, e.g. fluoroscopic imaging, with or without contrast media, and transesophageal echocardiography (TEE) images, as well as sensor data comprising pressure waveforms from the multi-sensor catheter or guidewire and associated hemodynamic parameters calculated or derived from the received optical pressure sensor data.

While a specialized signal processing unit or interface, which may be referred to as a "signal conditioner", is used to receive optical data from the multi-sensor catheter or multi-sensor guidewire, and generate output data indicative of pressure for display of pressure waveforms, the output data may be fed by a standard data connection, wired or wireless, to a processor, such as a general purpose computer, which is configured to provide the required functionality. For example, the system includes a processor and a computer program product (typically referred to as a software application or computer code), embodied in a non-transitory computer readable medium storing instructions, for execution in a processor of a control system for a multi-sensor catheter or a multi-sensor guidewire, for processing optical data received concurrently from a plurality of optical pressure sensors indicative of blood pressure, displaying a corresponding plurality of blood pressure waveforms, and optionally flow velocity data, and displaying numeric data relating to selected hemodynamic parameters and indexes.

Dual Pressure Sensor PA Catheter and Control System Configured for Heart Failure Monitoring and Management Heart failure (HF), which may be referred to as congestive heart failure (CHF), is a condition in which the heart is unable to pump well enough to maintain blood flow to meet the demands of the body. Heart failure may be associated with systolic disfunction and/or diastolic disfunction. In summary, in systolic disfunction, the heart is unable to contract sufficiently to eject blood effectively, resulting in poor output; in diastolic disfunction, the heart is unable to relax sufficiently to allow in-flow of blood, and congestion occurs because sufficient blood cannot get into the heart. Heart failure may occur with a reduced ejection fraction, resulting from systolic disfunction. Heart failure may occur with a normal ejection fraction, resulting from diastolic disfunction.

Treatment of heart failure may centre around reaching an optimal fluid level. Pulmonary artery pressures (PA and PCWP) and central venous pressure CVP are two important measurements of fluid status in heart failure patients.

Mild heart failure may be monitored by physical examination, e.g. examination for edema, JVP (jugular venous pressure), lung sounds, blood chemistry analysis (e.g. BUN/CR (blood urea nitrogen to creatinine ratio), BNP (brain natriuretic peptide)) and non-invasive ultrasound methods. Current methods of monitoring heart failure in new patients with acute exacerbations may require more invasive methods, such as use of Swann-Ganz (SG) catheters to measure CVP and pulmonary artery pressures. As mentioned above, SG catheters are fluid-filled catheters that transmit internal blood pressure to external pressure sensors, e.g. piezoresistive pressure sensors, through fluid-filled lumens of the catheter; the external pressure sensors need to be adjusted to the same level as a patient's heart to accurately measure internal cardiac pressures. To get accurate pressure measurements, the fluid-filled lumens must be of a sufficient size, requiring that SG catheters have a large external diameter, typically 8 or 9 French. Thus, the SG catheter must be inserted through a large central blood vessel, requiring insertion by specially trained physicians, increasing infection risks, and limiting the patient's mobility. Implantable heart monitoring devices, e.g. CardioMEMS™, involve additional long term risks, higher costs, and require placement by physicians in a cardiac catheterization lab. As a result, there is a higher threshold for using cardiac monitoring implants of this type, e.g. it is reserved for inpatients in long-term care, with more severe heart failure.

There is a need for further improvements or alternatives to existing devices, systems and method, e.g. simplified and lower cost devices, systems and methods for monitoring and management of heart failure.

Changes in PA pressure are an early and leading indicator of worsening heart failure. Thus, it is desirable to be able to monitor changes in PA pressure by direct blood pressure measurements within the heart.

Simplified multi-sensor PA catheters of exemplary embodiments are now described, which are configured more specifically for heart failure monitoring and management.

For monitoring of CVP and pulmonary artery pressures (i.e. PA pressure and PWCP), a flow-directed multi-sensor PA catheter of a third embodiment comprises two optical pressure sensors, having pressure sensor positions which are located to place one optical pressure sensor in the pulmonary artery and one optical pressure sensor in the right atrium. Since only two optical pressure sensors are required for pressure measurements in the RA and PA, the outer diameter of a dual-sensor PA catheter may be reduced, e.g. to 5 French or less, to facilitate insertion through one of the veins of the lower or upper arm (e.g. median cubital vein or basilic vein). A smaller outside diameter allows for the PA catheter to be inserted in a manner similar to insertion of a peripherally inserted central catheter (PICC). A PICC line is a soft, flexible catheter that provides for central venous access for administration of drugs and medications for long-term care, e.g. days or months. A PICC nurse is a specially-certified and accredited registered nurse, who is trained to insert PICC lines into patients, e.g. at the bedside, without requiring access to a cardiac catheterization lab.

Figure 15:
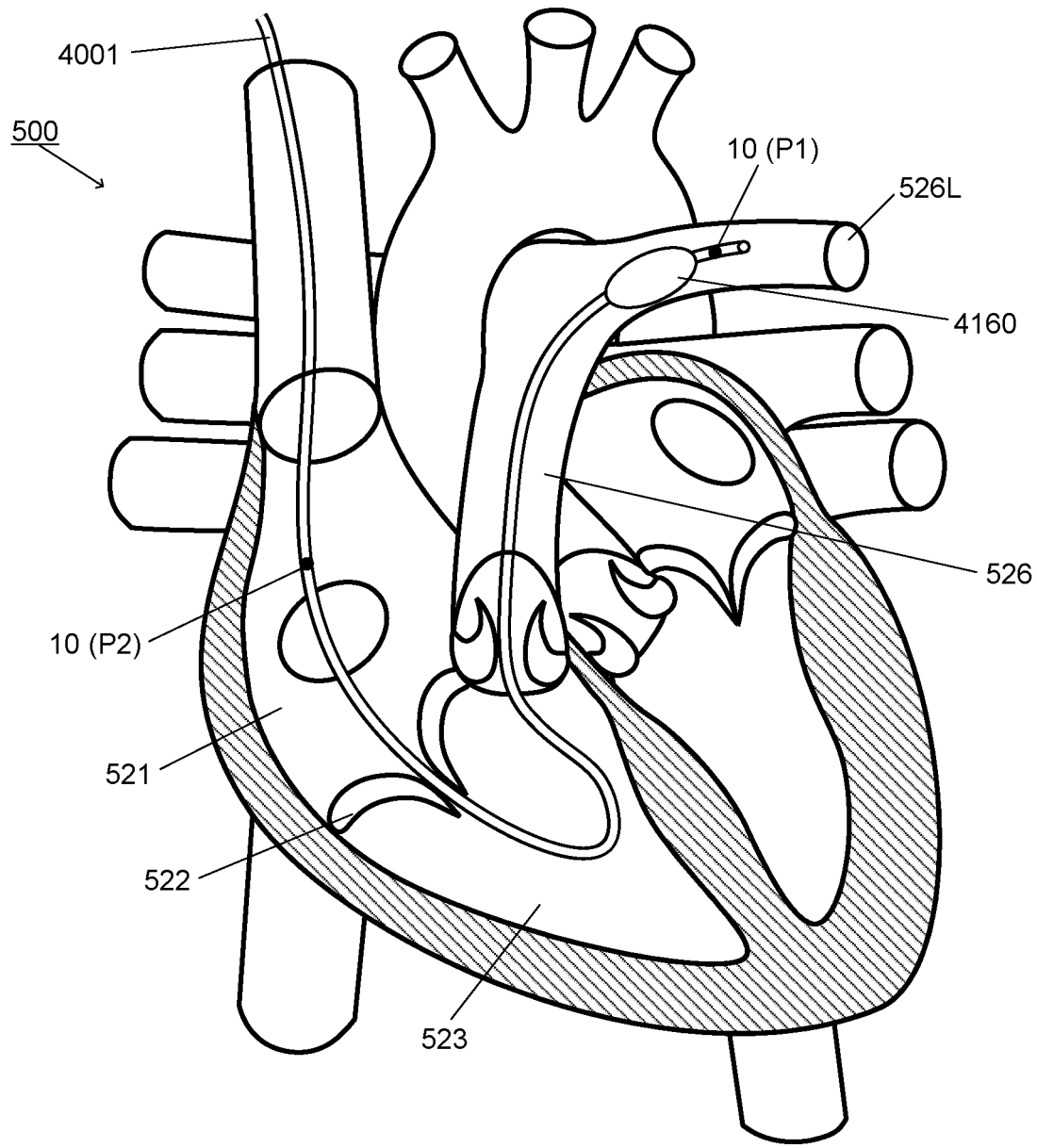
FIG. 15 shows a schematic partial cross-sectional diagram of a human heart to illustrate placement of a multi-sensor PA catheter of a third embodiment within the right heart and PA for concurrent measurements of blood pressure in the RA and in the PA.

FIG. 15 shows a schematic partial cross-sectional diagram of a human heart 500 to illustrate placement of a multi-sensor PA catheter 4001 of a third embodiment within the right heart and PA 526 for diagnostic measurements of hemodynamic parameters. The tip of the PA catheter is introduced from the superior vena cava into the RA 521, advanced through the tricuspid valve 522, into the RV 523, and then through the pulmonic valve 524 into the PA 526. During insertion, the inflatable balloon tip 4160 is inflated in the RV so that it is flow directed from the RV into the PA, until the balloon tip reaches the PCWP position, e.g. in the left branch of the pulmonary artery 526L. The balloon is then deflated. First and second pressure sensors 10 (P1 and P2) are positioned at sensor locations that enable concurrent measurements of blood pressure in the RA 521, to determine the CVP, and in the PA 526 to determine the PA pressure and, when the balloon is inflated, the PCWP.

Potential catch points during insertion of a PICC line into the heart through a vein in the arm are at the shoulder and in the RV. These potential catch points will also be encountered during insertion of the multi-sensor PA catheter. As will be described in detail with reference to FIGS. 17, 18A and 18B, the PA catheter includes a guidewire lumen so that a small diameter guidewire, e.g. 0.018 inch guidewire, may be used to assist with insertion. During insertion of the multi-sensor PA catheter 4001 over the guidewire, operation of the optical pressure sensors and observation of the blood pressure waveforms on the PCM screen will provide guidance with regard to positioning of the optical sensors as the tip of the PA catheter is advanced into the heart. That is, as the catheter is introduced into the heart and the first pressure sensor P1 moves from the RA 521, to the RV 523 and into the PA 526, characteristic pressure waveforms for the RA, RV and PA will be observed sequentially on the pressure trace for P1, and when the second sensor P2 is positioned in the RA the pressure waveform for the RA will be observed on the pressure trace for P2 (e.g. see characteristic waveforms illustrated schematically in FIG. 4 for a conventional SG catheter).

Figure 16:
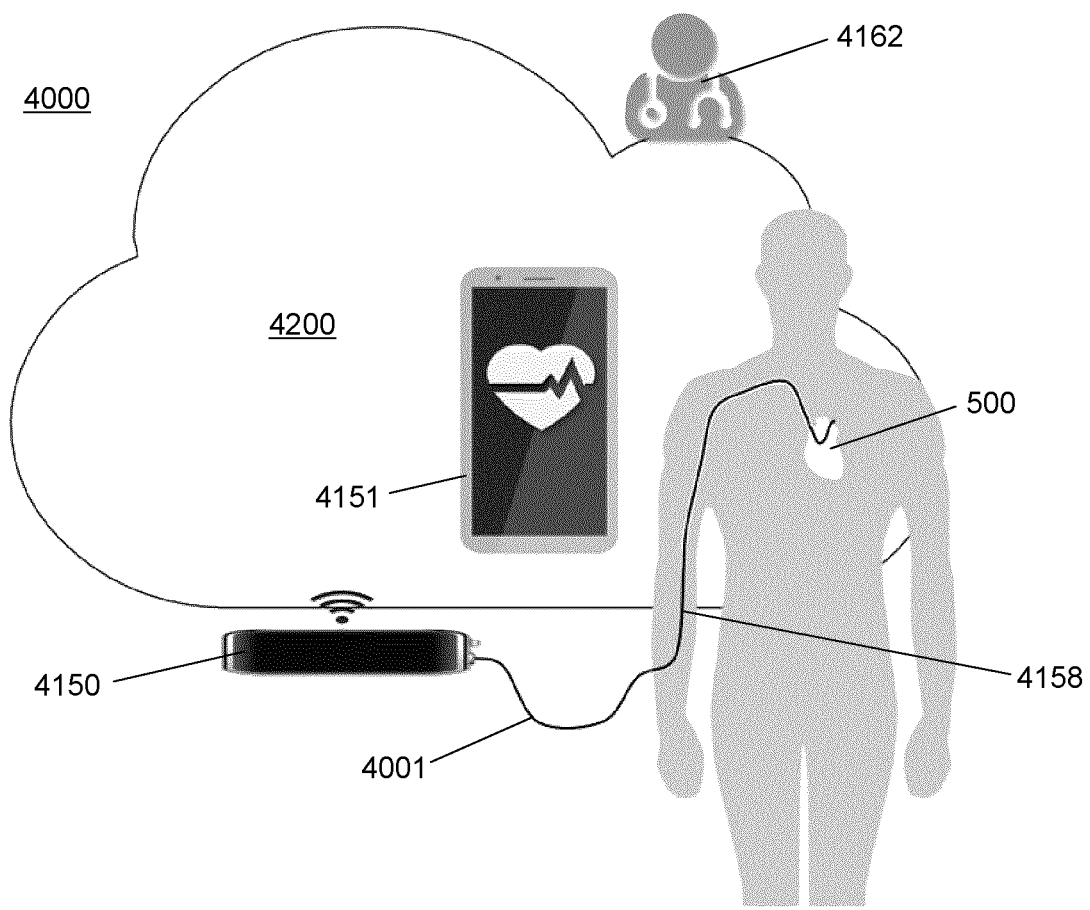
FIG. 16 shows a schematic representation of a system comprising the multi-sensor PA catheter of the third embodiment and a control system.

FIG. 16 shows a schematic representation of a system 4000 comprising a multi-sensor PA catheter 4001 of the third embodiment and a control system 4150 for heart failure monitoring. As illustrated schematically, by providing a smaller diameter PA catheter and miniaturization of the control system in the form of a portable unit, e.g. a bedside unit, or a small wearable unit, a multi-sensor PA catheter may be used for continuous or periodic monitoring of CVP and PA blood pressures for patients with less severe heart failure, while providing the patient with more mobility. If the multi-sensor PA catheter is provided in a smaller diameter catheter, e.g. 4 French or less, so that it can be inserted into the heart 500 through one of the veins of the lower or upper arm 4158, it is more comfortable and convenient for the patient, and it becomes feasible to provide longer term monitoring, e.g. over days or months. For example, a system with a portable controller would allow for more mobility for patients within a hospital situation or in a care facility. With further miniaturization of the control system, it is envisaged that the controller may be a wearable device which would allow for in-home use and remote monitoring. For example, as illustrated schematically the control system 4150 may comprise a portable unit which communicates with a remote patient monitoring system 4151, which can be accessed by a healthcare professional 4162. For example, the control system 4150 may communicate with a remote patient monitoring system 4151, directly through a communications interface to a hospital network or through a communications network 4200, e.g. via a personal computing device or an app on the patient's smartphone.

Figure 17:
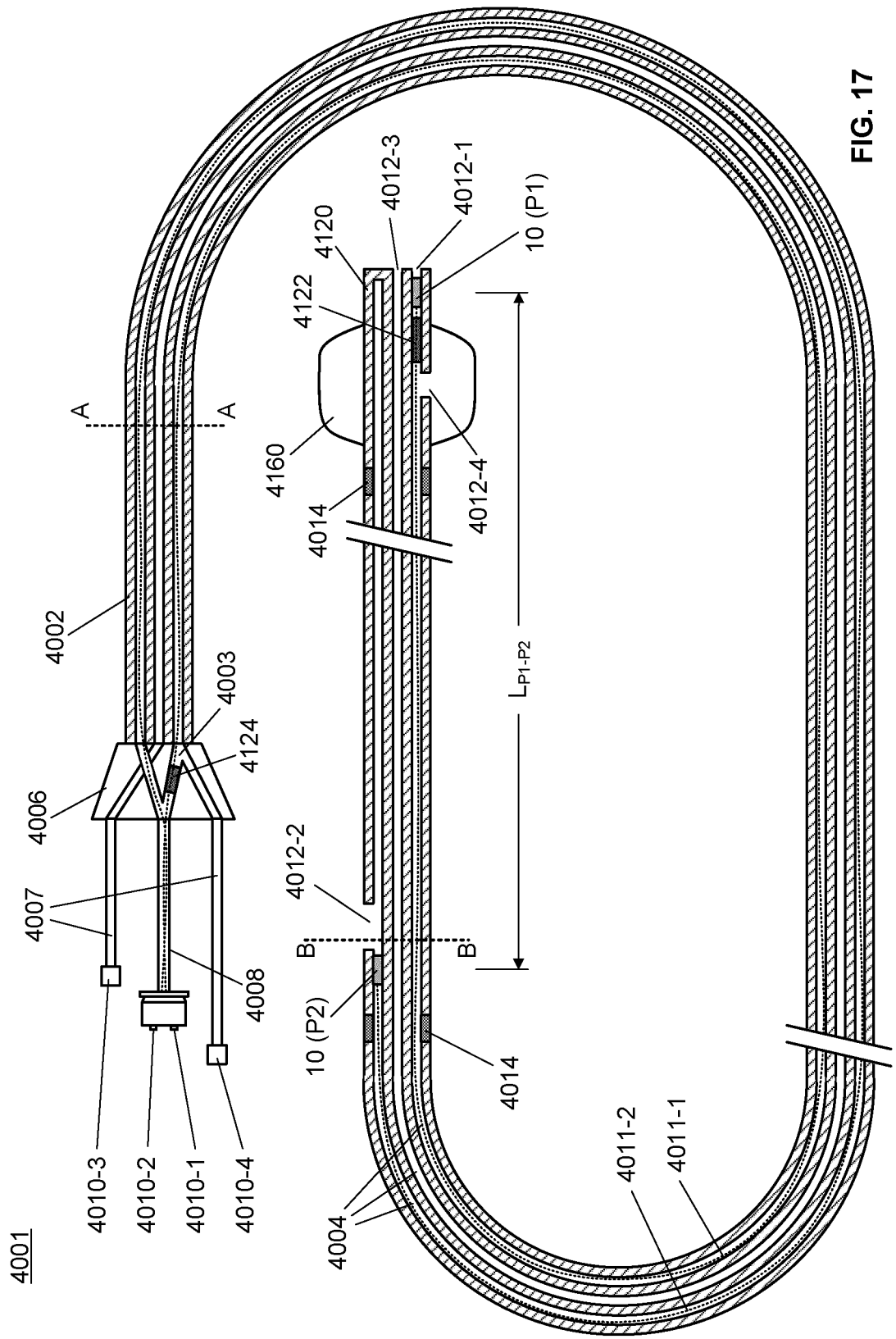
FIG. 17 shows a schematic longitudinal cross-sectional view of an apparatus for right heart and PA catheterization comprising a multi-sensor PA catheter of the third embodiment.
Figure 18A:
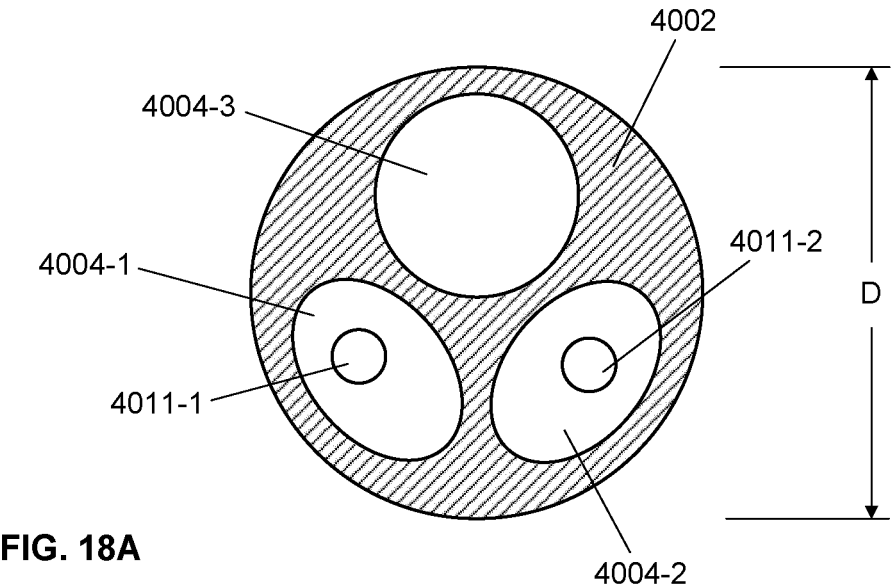
FIG. 18A shows a schematic enlarged axial cross-sectional view of the multi-lumen catheter illustrated in FIG. 17 taken through plane A-A of FIG. 17.
Figure 18B:
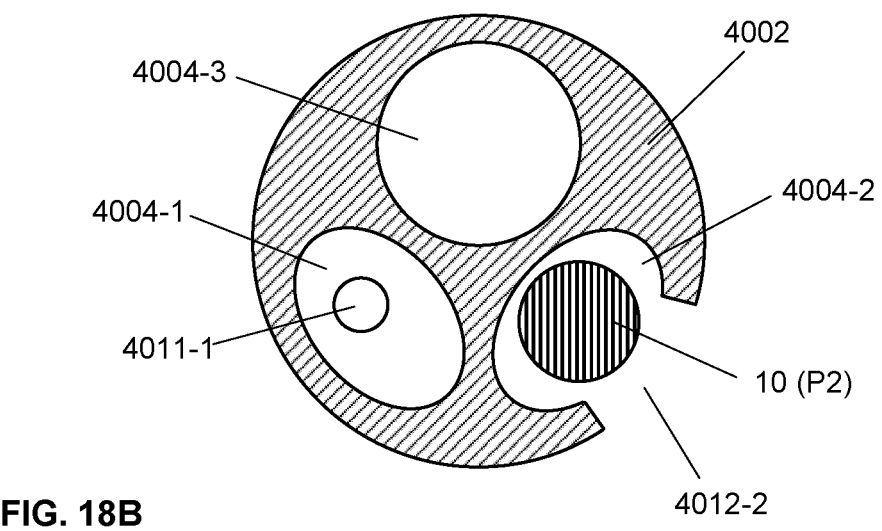
FIG. 18B shows a schematic enlarged axial cross-sectional view of the multi-lumen catheter illustrated in FIG. 17 taken through plane B-B of FIG. 17.

As illustrated schematically in FIGS. 17, 18A and 18B, the multi-sensor PA catheter 4000 of the third embodiment comprises a length of multi-lumen catheter tubing 4002 having three lumens 4004, extending from a connection hub 4006 at the proximal end to a distal end which comprises an atraumatic tip 4120. There is an inflatable balloon 4160 near the distal tip 4120. A first optical fiber 4011-1 and a first optical pressure sensor 10 (P1) are provided in a first lumen 4004-1 and the first optical pressure sensor P1 is located close to the distal tip 4120. A second optical fiber 4011-2 and a second pressure sensor 10 (P2) are provided in a second lumen 4004-2, with the second optical pressure sensor P2 located a distance $L_{P1-P2}$, e.g. ~30 cm (e.g. in a range of 20 cm to 30 cm, depending on the size and anatomy of the heart and blood vessels) from the first optical pressure sensor P1 for positioning one sensor in the RA and one in the PA. Apertures 4012-1 and 4012-2 are provided near each sensor P1 and P2 for fluid contact. A third lumen 4004-3 extends from an opening at the distal tip 4012-3 through the hub 4006, through tubing 4007, to fluid port 4010-3. This lumen is provided for insertion of a small diameter guidewire, such as a 0.018 inch guidewire, and may also be used for fluid injection and fluid sampling. At the proximal end, the optical fibers 4011-1 and 4011-2 within the first and second lumens extend through the hub 4006 to optical connectors 4010-1 and 4010-2, respectively. The first lumen 4004-1 is also connected through the hub 4006 to a fluid injection port 4010-4, e.g. through a Y branch connection 4003 in the connection hub 4006, and the first lumen is also connected to the inflatable balloon through aperture 4012-4. This arrangement enables the first lumen to accommodate the first pressure sensor P1, and its optical fiber, and also serve as a balloon inflation/deflation lumen. To isolate the first pressure sensor P1 from the balloon inflation port, a plug of sealant 4122 is provided to seal the first lumen between the balloon inflation aperture 4012-4 and the optical pressure sensor P1. Another plug of sealant 4124 for the first lumen is also provided within the hub 4006 at the proximal end, to seal around the optical fiber 4011-1. Thus, there are three lumens, and the hub has three external ports comprising lengths of flexible tubing 4007 and 4008. The optical fibers 4011-1 and 401102 extend through flexible tubing 4008 to a dual port optical connector with ports 4010-1 and 4010-2 for each of the optical fibers 4011-1 and 4011-2, i.e. for optical pressure sensors at P1 and P2. A first length of flexible tubing 4007 extends to a guidewire port 4010-3, which may also be used for fluid withdrawal or injection. A second length of flexible tubing extends to a balloon inflation/deflation port 4010-4. If required, a marker 4014 is provided near each sensor to allow for imaging to locate of the sensors during insertion and within the heart, e.g. radiopaque markers for radiographic imaging, or markers for MRI imaging. FIG. 18A shows a schematic enlarged axial cross-sectional view of the multi-lumen catheter illustrated in FIG. 17 taken through plane A-A of FIG. 17. FIG. 18B shows a schematic enlarged axial cross-sectional view of the multi-lumen catheter illustrated in FIG. 17 taken through plane B-B of FIG. 17. As illustrated schematically, the first and second lumens 4004-1 and 4004-2 of the multi-lumen catheter tubing 4002 are sized to accommodate the optical pressure sensors P1 and P2 and their optical fibers 4011-1 and 4011-2, and the third lumen 4004-3 is sized to accept a guidewire, e.g. a 0.018 inch diameter guidewire.

Figure 19:
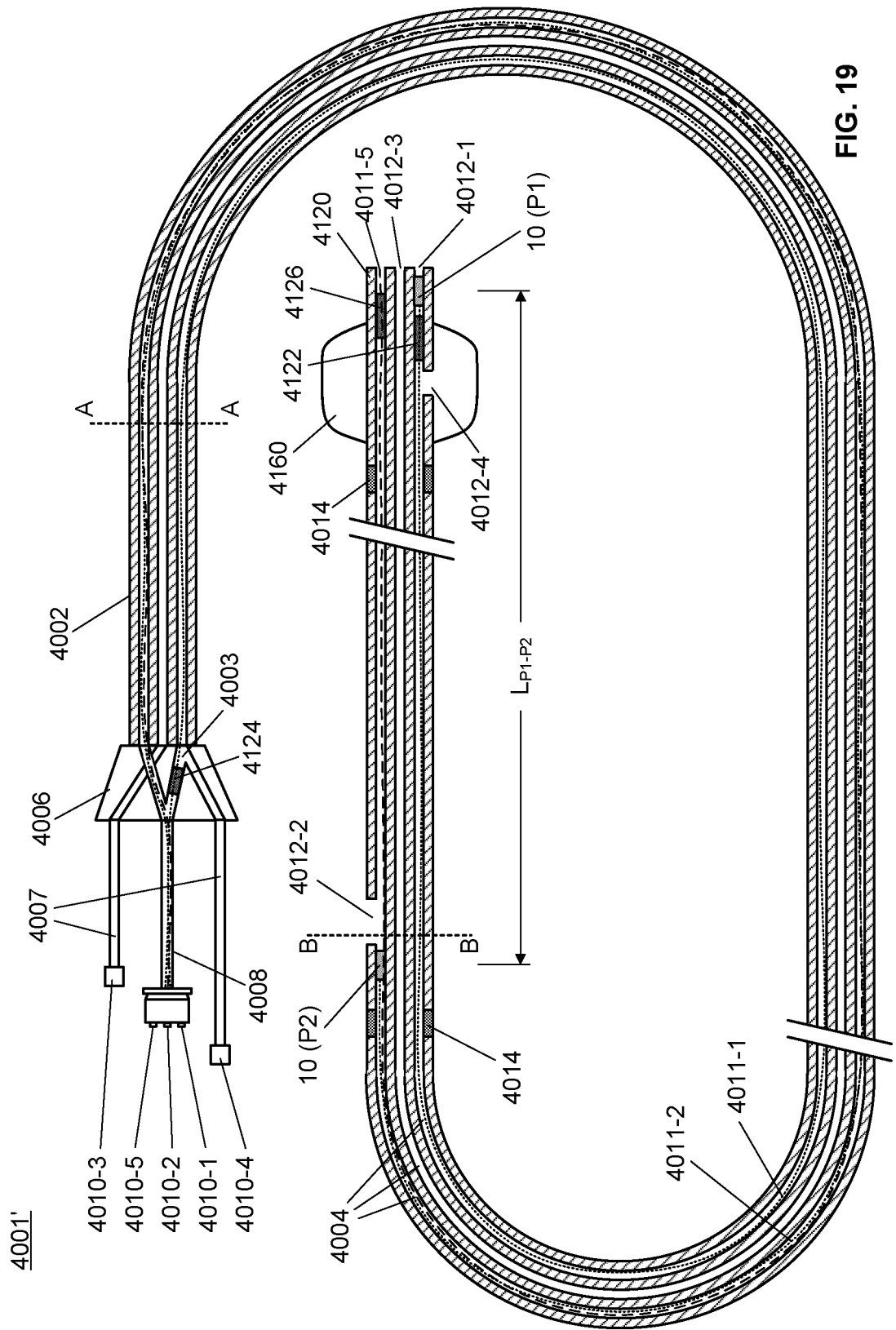
FIG. 19 shows a schematic longitudinal cross-sectional view of an apparatus for right heart and PA catheterization comprising a multi-sensor PA catheter of a fourth embodiment.
Figure 20A:
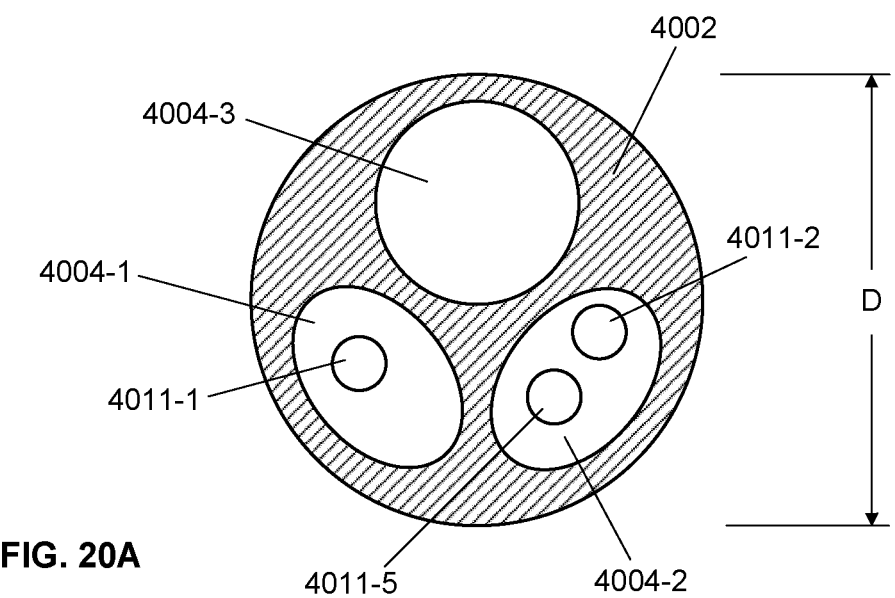
FIG. 20A shows a schematic enlarged axial cross-sectional view of the multi-lumen catheter illustrated in FIG. 19 taken through plane A-A of FIG. 19.
Figure 20B:
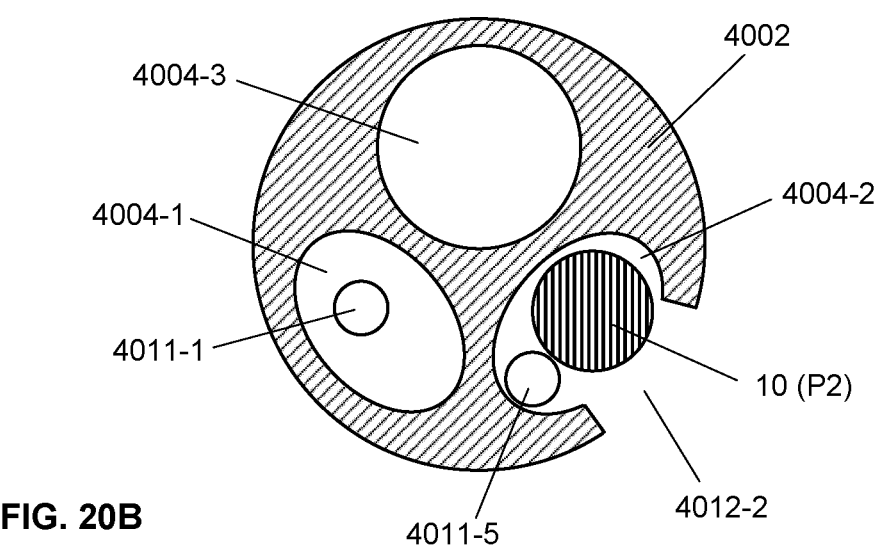
FIG. 20B shows a schematic enlarged axial cross-sectional view of the multi-lumen catheter illustrated in FIG. 19 taken through plane B-B of FIG. 19.

A multi-sensor PA catheter of a fourth embodiment 4001' is illustrated schematically in FIGS. 19, 20A and 20B. The multi-sensor PA catheter of this embodiment differs from that illustrated in FIGS. 17, 19A and 19B in that it also includes a third optical fiber 4011-5 in the second lumen 4004-2, which allows for optical oximetry for monitoring blood oxygen levels. The multi-sensor PA catheter comprises a length of multi-lumen catheter tubing 4002 having three lumens 4004, extending from a connection hub 4006 at the proximal end to a distal end which comprises an atraumatic tip 4120. There is an inflatable balloon 4160 near the distal tip 4120. A first optical fiber 4011-1 and a first optical pressure sensor 10 (P1) are provided in a first lumen 4004-1 and the first optical pressure sensor P1 is located close to the distal tip 4120. A second optical fiber 4011-2 and a second pressure sensor 10 (P2) are provided in a second lumen 4004-2, with the second optical pressure sensor P2 located a distance $L_{P1-P2}$ from the first optical pressure sensor P1. Apertures 4012-1 and 4012-2 are provided near each sensor P1 and P2 for fluid contact. A third lumen 4004-3 extends from an opening at the distal tip 4012-3 through the hub 4006, through tubing 4007, to a port 4010-3. This lumen is provided for insertion of a small diameter guidewire, such as a 0.018 inch guidewire, and may also be used for fluid injection and fluid sampling. At the proximal end, the optical fibers 4011-1 and 4011-2 within the first and second lumens extend through the hub 4006 and through flexible tubing 4008 to optical connectors 4010-1 and 4010-2, respectively of a multi-port optical connector. The first lumen 4004-1 is also connected through the hub 4006 and through flexible tubing 4007 to a fluid injection port 4010-4, e.g. through a Y branch connection 4003 in the connection hub 4006, and near the distal tip, the first lumen is also connected to the inflatable balloon through aperture 4012-4. This arrangement enables the first lumen to accommodate the first pressure sensor P1 and also serve as a balloon inflation/deflation lumen. To isolate the first pressure sensor P1 from the balloon inflation port, a plug of sealant 4122 is provided to seal the first lumen between the balloon inflation aperture 4012-4 and the optical pressure sensor P1. Another plug of sealant 4124 for the first lumen is also provided within the hub 4006 at the proximal end, to seal around the optical fiber. For optical oximetry, the third optical fiber 4011-5 extends through the second lumen 4004-2, i.e. in the same lumen as optical fiber 4011-2 and sensor P2 to an opening at the distal tip 4120 for fluid contact with the blood. The distal tip of the third optical fiber 4011-5 is positioned at the tip 4120 of the catheter for optical sampling of blood oxygen level, and the proximal tip of the third optical fiber 4011-5 extends through the hub 4006 and tubing 4008, to another port 4010-5 of the multiport optical connector at the proximal end of the catheter, i.e. for connection to an optical oximeter within the control system. A plug of sealant 4126 is provided around the fiber 4011-5 near the distal tip, to isolate the second optical sensor 10 (P2) from the aperture at the distal tip. If required, a marker 4014 is provided near each sensor to facilitate location of the sensors by imaging, e.g. radiopaque markers for radiographic imaging, or markers for MRI imaging.

For optical oximetry within the PA, the distal tip of the third optical fiber is located near aperture 4012-5 at the distal tip 4120 of the catheter, for fluid contact with blood and the proximal end of the third optical fiber is connected via optical connector and port 4010-5 to an oximetry device comprising a light source and detector, and electronics within the control system. The oximetry device measures reflectance or absorption of light by the blood, which is used to compute a blood oxygen level, or a blood oxygen saturation parameter as a percentage value. For example, the oximetry device is configured for measuring reflectance or absorption of light of first and second wavelengths, typically red (R) and infrared (IR) wavelengths which are differentially absorbed and reflected by deoxy-hemoglobin and oxy-hemoglobin in the blood. In principle, this form of optical oximetry is based on the relationship between blood oxygen saturation $SvO_2$ and the ratio of the infrared-to-red (IR/R) light backscattered from red blood cells in blood, e.g. $SvO2=A-B(IR/R)$, where, A and B are empirically derived calibration coefficients. Any suitable oximetry device may be used.

FIG. 20A shows a schematic enlarged axial cross-sectional view of the multi-lumen catheter illustrated in FIG. 19 taken through plane A-A of FIG. 19. FIG. 20B shows a schematic enlarged axial cross-sectional view of the multi-lumen catheter illustrated in FIG. 19 taken through plane B-B of FIG. 19. As illustrated schematically, the first lumen 4004-1 of the multi-lumen catheter tubing 4002 is sized to accommodate the optical pressure sensors P1 and optical fiber 4011-1; the second lumen 4004-2 is sized to accommodate the optical pressure sensor P2, its optical fiber 4011-2, and the optical fiber 4011-5 for oximetry; the third lumen 4004-3 is sized to accept a small diameter guidewire, e.g. a 0.018 inch diameter guidewire.

Figure 21A:
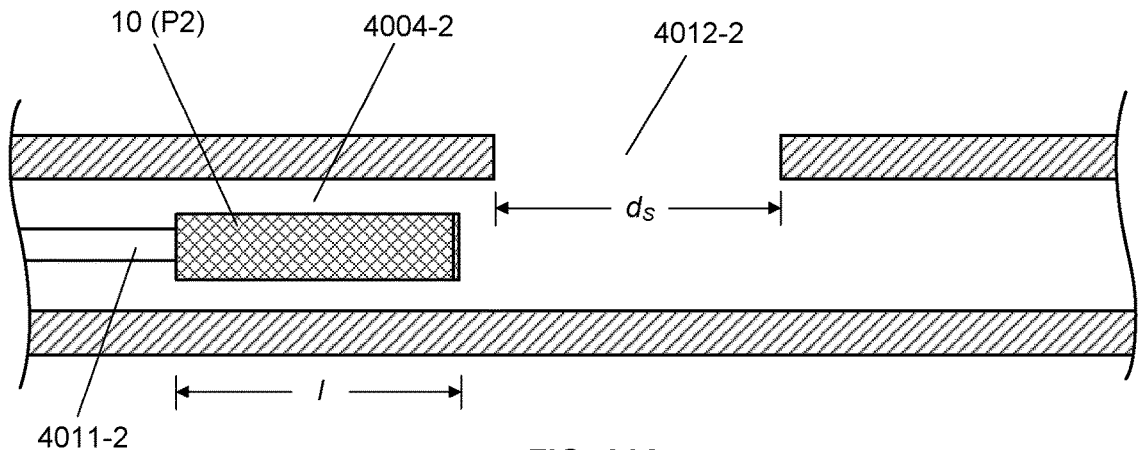
FIG. 21A shows a schematic enlarged transverse cross-sectional view of part of the multi-lumen catheter of FIG. 17 in the region near sensor P2.

FIG. 21A shows a schematic enlarged transverse cross-sectional view of part of the multi-lumen catheter of FIG. 17 comprising the second lumen 4004-2 in the region near sensor P2, showing the aperture 4012-2 of diameter d, near sensor P2 for fluid contact with the sensor P2. The sensor is contained within a protective sleeve comprising a short length l of reinforcing tubing, e.g. 2 mm stainless steel or polyimide tubing to reinforce the region where the sensor P2 is bonded to the optical fiber 4011-2.

Figure 21B:
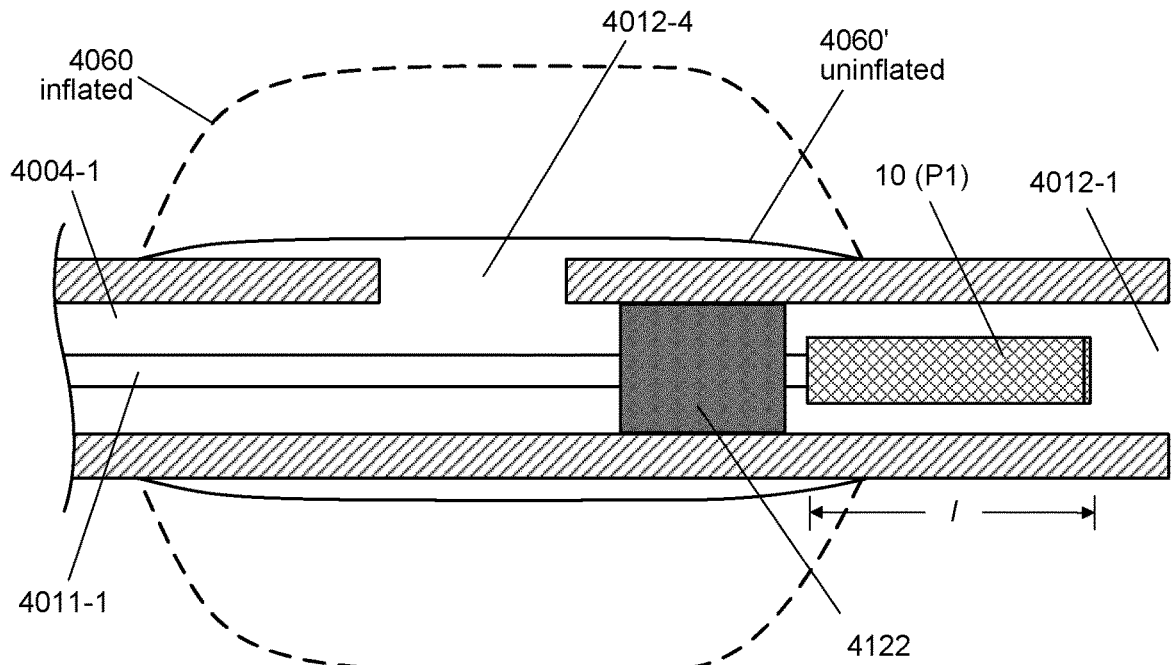
FIG. 21B shows a schematic enlarged transverse cross-sectional view of part of the multi-lumen catheter of FIG. 17 in the region near the distal tip comprising the inflatable balloon and sensor P1.

FIG. 21B shows a schematic enlarged transverse cross-sectional view of part of the multi-lumen catheter of FIG. 17 comprising the first lumen 4004-1 in the region near the distal tip comprising an inflatable balloon 4060 and sensor P1. There is an aperture 4012-1 at the end of the first lumen provided for fluid contact with the sensor P1, which is similarly reinforced by a protective sleeve l as described for P1. Also shown is the aperture 4012-4 for inflation/deinflation of the balloon. Since the optical sensor P1, and its optical fiber, and the balloon share the same lumen, the lumen is plugged, e.g. with gel or other sealant 4124, to isolate the pressure sensor P1 from the balloon inflation lumen.

Figure 22:
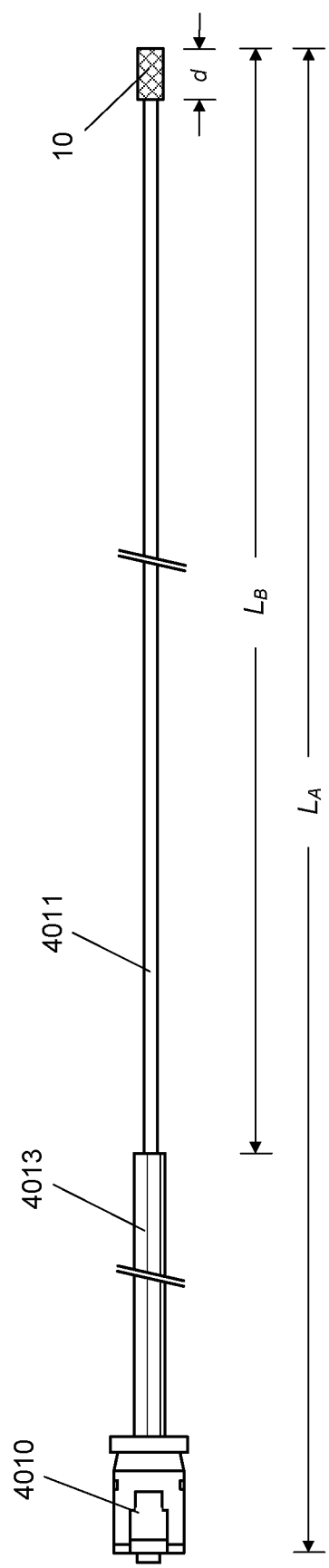
FIG. 22 shows a schematic view of an assembly of an optical fiber having a sensor at the distal end and an optical connector at the proximal end.

FIG. 22 shows a schematic view of a fiber optic sensor assembly of an optical fiber 4011 having a sensor 10 within a protective sleeve of length d at the distal end and an optical connector 4010 at the proximal end. The length $L_B$ of the bare section of the optical fiber and the optical sensor is, for example, 120 cm, and the total length of the assembly $L_A$ including the optical connector and protective nylon tubing at the proximal end, is for example, 170 cm.

Figure 23:
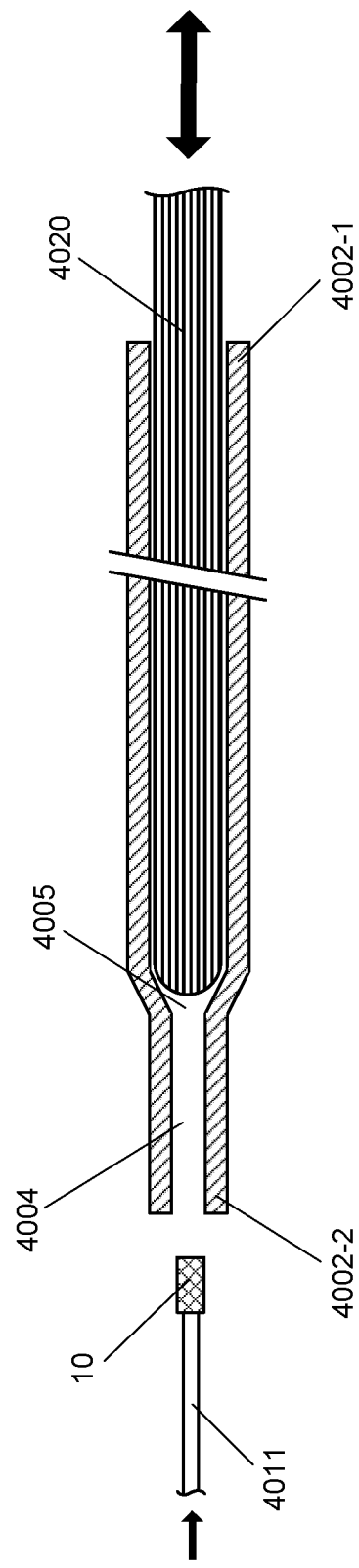
FIG. 23 shows a schematic diagram to illustrate a step of preparation of a catheter lumen for insertion of a pressure sensor and its optical fiber.

FIG. 23 shows a schematic diagram to illustrate a step of preparation of a catheter lumen for insertion of a pressure sensor, when the optical sensor and optical fiber is inserted from the proximal end of the catheter tubing. To facilitate insertion of the fiber optic sensor assembly into a lumen of the multi-lumen catheter, a mandrel may be used to stretch or dilate the lumen temporarily during insertion.

Referring back to the cross-sectional schematic views shown in FIGS. 18A and 18B, and 20A and 20B, by way of example, the size and shape of the three lumens are selected to accommodate the optical fibers and optical sensors, and a guidewire of the required diameter, while providing the required mechanical properties, e.g. stiffness or flexibility of the catheter tubing. The tip of the catheter may be shaped to form an atraumatic distal tip, e.g. a rounded or soft tip. With respect to sizing, by way of example, the multi-sensor catheters of the third and fourth embodiments may comprise 4 French catheter tubing, optical fibers having a diameter of 100 μm or 155 μm, and FP MOMs optical pressure sensors having a 260 μm diameter; the FP MOMS optical pressure sensors may be protected within reinforcing tubing, e.g. comprising a 2 mm length of 307 μm diameter stainless steel tubing, or other suitable reinforcing material. Smaller diameter sensors and optical fibers would allow for use of multi-lumen tubing having a smaller outside diameter, i.e. <4 French, which may be preferred to facilitate insertion through a smaller vein, and for patient comfort for longer term monitoring of heart failure. However, since the multi-sensor PA catheter is a single-use medical device, and it is desirable to use lower cost components, these examples described herein demonstrate that the PA catheter for heart failure monitoring may be fabricated with a 4 French outside diameter, using standard diameter optical fibers, such as low cost 100 μm or 155 μm optical fibers used for telecommunications, and optical pressure sensors which are currently commercially available. It is expected that commercial availability of smaller dimension optical pressure sensors and optical fibers at competitive prices, will allow for further miniaturization of multi-sensor PA catheters of the embodiments described herein.

Figure 24A:
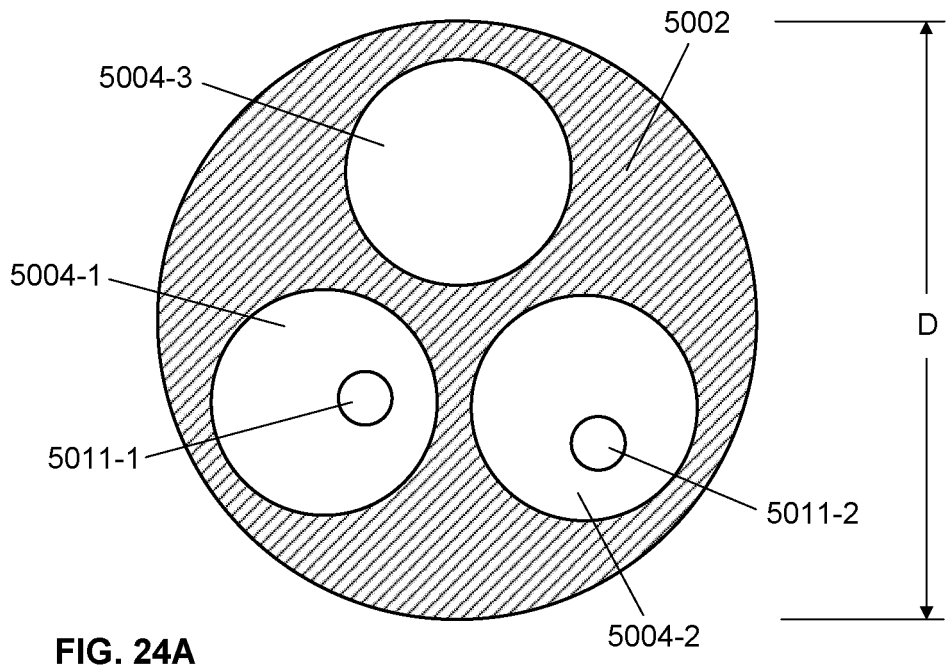
FIG. 24A shows schematic enlarged axial cross-sectional view of a multi-lumen catheter which is a variant of the embodiment shown in FIG. 18A.
Figure 24B:
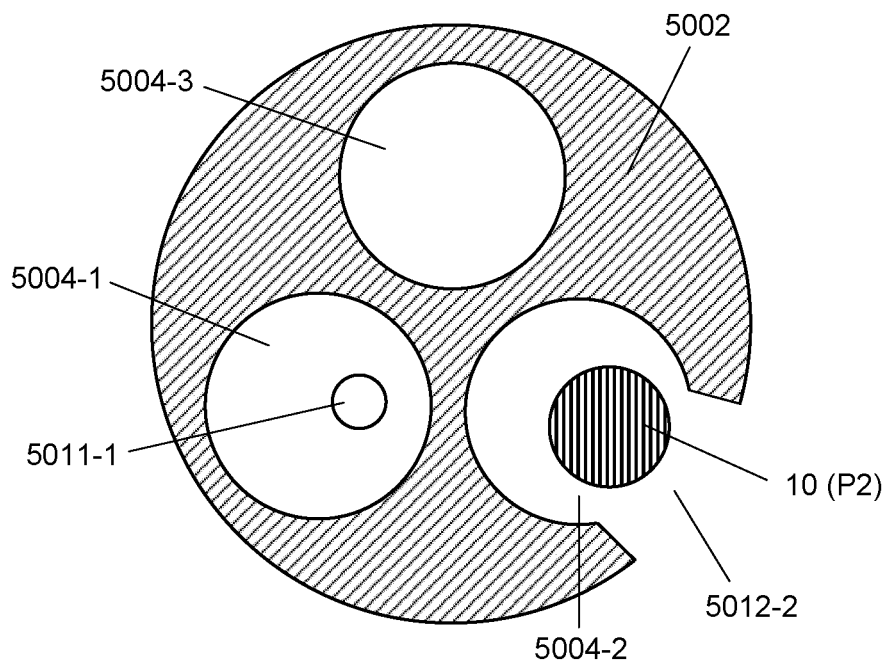
FIG. 24B shows a schematic enlarged axial cross-sectional view of a multi-lumen catheter which is a variant of the embodiment shown in FIG. 18B.

In other embodiments, the multi-lumen catheter may comprise lumens of a different form and dimensions. For example, FIGS. 24A and 24B shows schematic enlarged axial cross-sectional views of a multi-lumen catheter which is a variant of the embodiment shown in FIGS. 18A and 18B comprising multi-lumen tubing 5002, e.g. 5 French diameter, with three equally sized lumens 5004-1, 5004-2 and 5004-3. Lumen 5004-3 is a guidewire lumen, and the first and second lumens 5004-1 and 5004-2 each contain an optical fiber 5011-1 and 5011-2 and optical pressure sensors, e.g. as shown in FIG. 24B, optical pressure sensor 10 (P2) with an aperture 5012-2 adjacent P2 for fluid contact. For example, in some scenarios, three equal sized lumens may be selected for rotational symmetry of mechanical properties of the multi-lumen tubing. On the other hand, an arrangement of lumens, such as shown in FIGS. 18A and 18B, can accommodate a 0.018 inch (0.45 mm) diameter guidewire in the third lumen, while the two smaller, oval shaped lumens, accommodate the optical fibers and optical sensors, all within a smaller diameter multi-lumen catheter, e.g. about 4 French.

For example, to achieve a target outside diameter of e.g. ≤4 F (1.3 mm), to enable insertion of the catheter through a smaller peripheral vein, e.g. a vein in the upper or lower arm, it is important to make effective use of the available cross-section of the catheter to accommodate a guidewire lumen as well as lumens for the optical fibers and sensors, and an inflation channel for the inflatable balloon. For example, for a 4 F outside diameter catheter tubing, to accommodate a guidewire lumen for a 0.018 inch (0.45 mm) diameter guidewire in the third lumen, as illustrated in FIGS. 18A and 18B, a suitably sized guidewire lumen with a circular cross-section is provided, e.g. having a diameter of 0.022 inch (0.56 mm). Allowing for a typical minimum exterior wall thickness of e.g. 0.004 inch, it is then possible to include two oval lumens as shown schematically in FIGS. 18A and 18B, each having lateral dimensions of e.g. 0.016 by 0.022 inch. For some embodiments, an oval shaped lumen may be preferred to a circular lumen. For example, as illustrated in FIGS. 18A and 18B, oval lumens occupying available space may be beneficial where a lumen has a dual purpose, e.g. when a lumen provides a space for an optical fiber with an optical pressure sensor and also serves as a channel for inflation/deflation of a balloon, and when a lumen accommodates both an optical fiber with optical pressure sensor and an optical fiber with an optical oximeter. Also, for fabrication, this arrangement of lumens, provides a more stable design for an extrusion molding process as the wall thickness is more uniform which helps to prevent warping and an inconsistent lumen and extrusion profile.

For insertion of the multi-sensor catheter into the right atrium through a smaller vein, e.g. through one of the veins in the upper or lower arm and through the superior vena cava, the outside diameter of catheter tubing is appropriately sized, e.g. having an outside diameter of ≤5 French, and preferably ≤4 French. For insertion of the multi-sensor catheter into the right heart via through a larger vein, e.g. through a femoral vein in the groin and through the inferior vena cava, catheter tubing with a larger outside diameter, e.g. >5 French may be used. It will be appreciated that, for longer term monitoring of heart failure, insertion of a multi-sensor PA catheter through a vein in the arm is more convenient (e.g. simplifies insertion by a PICC nurse) and is more comfortable for the patient, so a multi-sensor catheter with an outside diameter of ≤4 French is beneficial for this scenario, which may also enable use of a miniaturized portable control system, or a wearable control system with remote monitoring, as mentioned above.

Figure 25:
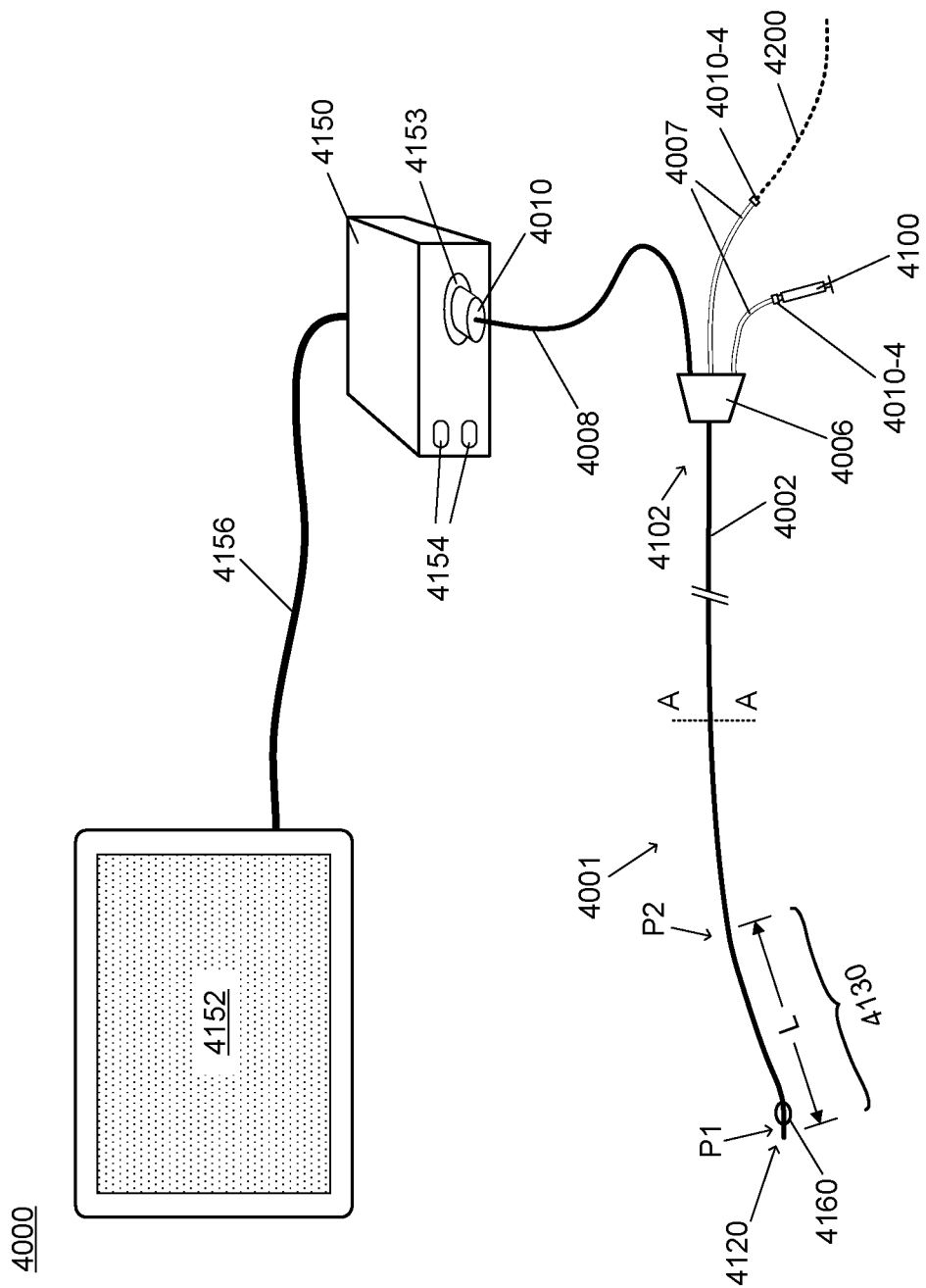
FIG. 25 illustrates schematically a system comprising an apparatus for right heart and PA catheterization comprising the multi-sensor PA catheter of the third embodiment and a controller.

FIG. 25 illustrates schematically a system of an embodiment comprising a multi-sensor PA catheter 4001 and a controller, i.e. control module 4150, and graphical display 4152 of a PCM. Elements of the multi-sensor PA catheter 4001 are labelled with the same reference numerals as shown in FIG. 17. The optical connector 4010 comprising optical ports for the optical fibers for P1 and P2 (and optionally for an additional fiber for oximetry as described with reference to FIG. 19) are connected to optical port 4153 on the control module 4150, which includes the optical signal conditioner, similar to the unit 2151 described with reference to FIG. 5, except that control unit 4150 is a simplified two sensor control unit for the two optical sensors P1 and P2. The controller 4150 also includes a signal converter unit, which enables the control unit 4150 to be directly connected to a BP-22 compliant PCM. In this embodiment, the signal converter unit is integrated with the control unit 4150, in the same housing. If required, the control unit 415 includes a user interface e.g. one or more switches/indicator lights 4154 for basic functions such as power on/off, standby power indicate, start/activate, etc. Of course, it is preferred that the control unit also includes a communications interface that allows functions to be controlled remotely, e.g. using a touch screen interface of the display 4152, or through an interface to another controller of the patient monitoring system.

Reference above to "a BP-22 compliant PCM" means a patient monitoring system or patient care monitor that is configured for use with conventional piezo-resistive pressure transducers producing analog signals indicative of blood pressure compliant with the ANSI BP-22 standard (ref.: ANSI/AAMI BP-22:1994/(R)2000 Blood Pressure Transducers). In use of conventional piezo-resistive pressure transducers, the piezo-resistor detects blood pressure by monitoring pressure in fluid filled catheter using an external piezo-resistive pressure transducer connected to the fluid filled catheter, in which the first and second piezo-resistive pressure transducers are each part of a Wheatstone bridge circuit, as shown in the circuit schematic of FIG. 26, which produces an analog signal output $V_S$ in response to an analog excitation signal $V_E$. The BP-22 standard sets out mechanical and electrical requirements (e.g. ref: section 4.2 of the BP-22 Standard). For example, the standard defines an excitation voltage $V_E$ in a range from direct current (DC) to 5000 Hz AC in a voltage range from 4V to 8V rms, and a sensitivity that provides an output signal of 5 μV/V/mmHg, i.e. an output of 5 μV per volt of $V_E$ per mmHg. To interface the digital signal outputs from the FP-MOMS optical pressure sensors to a BP-22 compliant PCM, a signal converter is required to convert the digital output signals indicative of pressure from the FP-MOMS optical pressure sensors to equivalent analog output signals $V_S$ that will be recognized by the BP-22 compliant PCM, based on a received analog excitation signal $V_E$, from the PCM.

Figure 27:
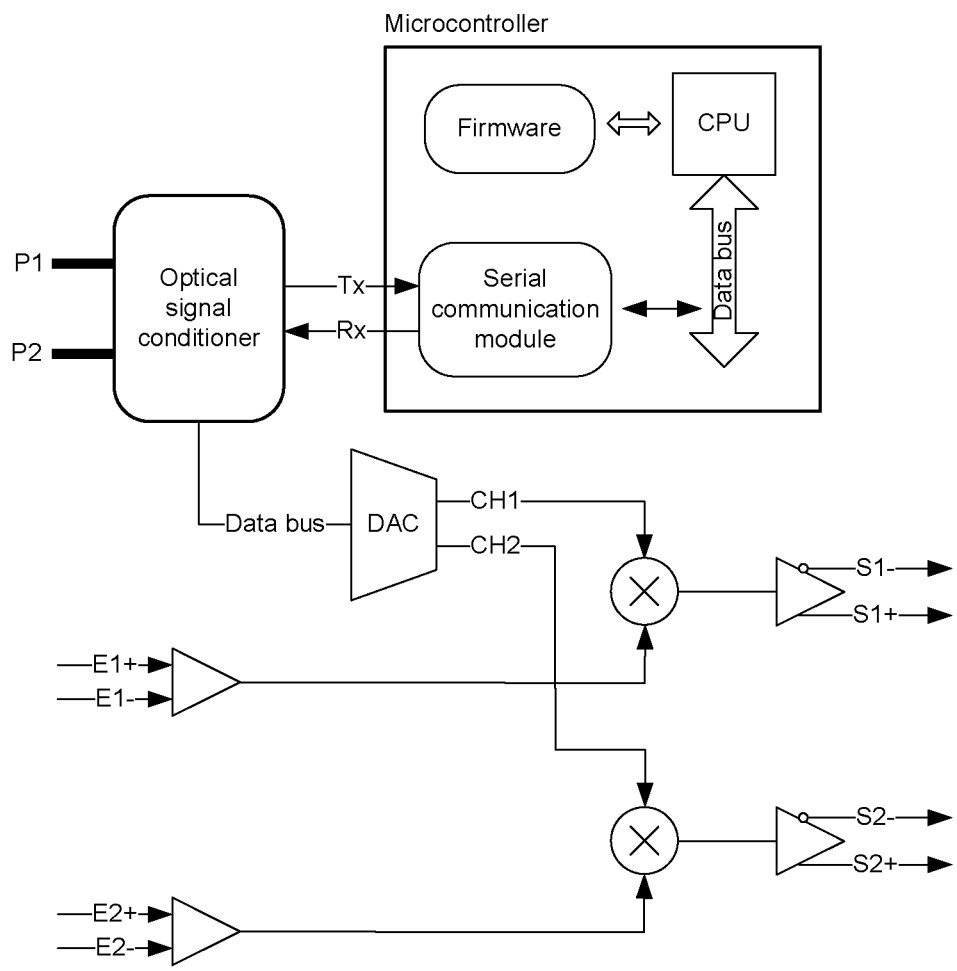
FIG. 27 shows a schematic block diagram of components of a controller comprising first and second channels for a dual pressure sensor PA catheter of embodiments described herein.

Thus, the system controller comprises an optical to BP-22 signal converter, e.g. as illustrated schematically in FIG. 27, the optical signal conditioner comprises a light source and detector with ports P1 and P2 for connection to optical connectors of the first and second optical pressure sensors. The optical signal conditioner generates digital output signals indicative of pressure, and receives digital control signals, through an interface to a serial communications module of a micro-controller. The signal conditioner may be integrated with, or be a separate module, from the interface which converts digital outputs to provide BP22 compliant analog signals.

Additionally, or alternatively, the optical control unit comprises ports for digital inputs and outputs, e.g. for wired or wireless coupling of the controller to a digital patient monitoring system and other peripherals, such as a network device or user device, e.g., a server, personal computer, or tablet which provides a user interface and/or data storage and analysis. (See PCT International patent application No, PCT/CA2018/051430).

Figure 26:
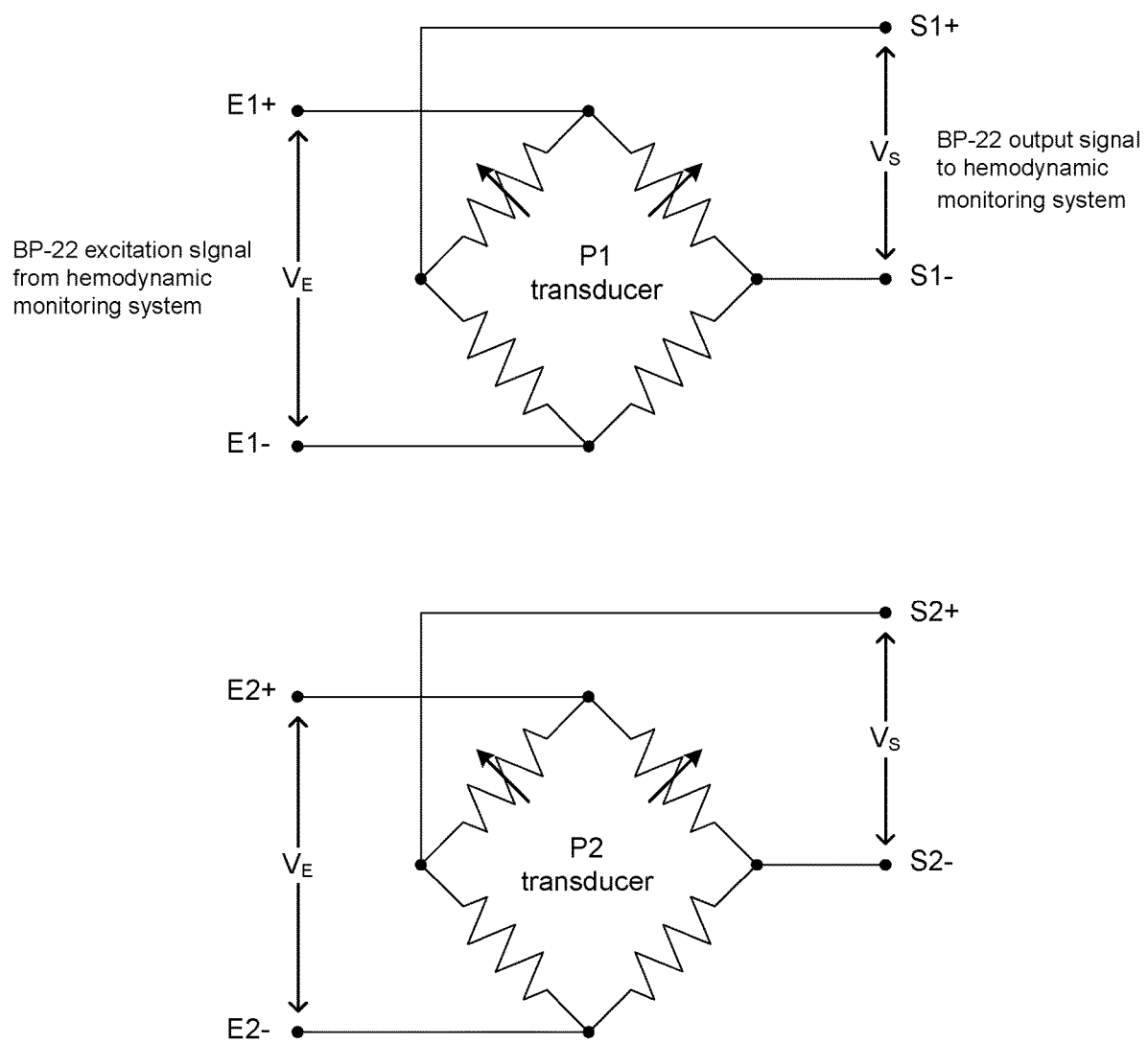
FIG. 26 shows a circuit schematic for a conventional piezoresistive pressure transducer arrangement in which the piezoresistive pressure transducer forms an arm of a Wheatstone bridge.

In a simplified form, as illustrated schematically in FIG. 27, a circuit emulating FIG. 26 with two BP-22 outputs from two blood pressure transducers P1 and P2 is provided. For each of the inputs P1 and P2 from the optical pressure sensors, digital signals indicative of pressure are fed from the optical signal conditioner through a data bus to a digital-to-analog-converter DAC. The control unit receives BP-22 compliant differential analog excitation (control) signals E1+ and E1− and E2+ and E2− from first and second channels of the hemodynamic monitoring systems of the PCM. These differential excitation signals are fed through respective buffers to provide non-differential signals E1 and E2. Digital signals indicative of pressure received from the signal conditioner are fed through the data bus to digital-to-analog converters (DAC) to generate corresponding analog signals. For each channel, the analog signals for first and second channels from the DAC are fed to an analog multiplier that also receives the analog excitation signal for the channel. The signal from the analog multiplier is then fed to a buffer to generate differential output signals S− and S+ for each channel.

Where the controller is to be interfaced to a BP-22 compliant PCM for monitoring blood pressure data, and the PCM is configured for displaying blood pressure waveforms, i.e. a pressure waveform from each optical pressure sensor, on a graphical user interface, the concurrent blood pressure waveforms for each of the FP optical pressure sensors may be displayed for one or more time intervals, and during one or more cardiac cycles. The PCM may be further configured to derive hemodynamic parameters from the blood pressure data and display numeric values of the parameters, as well as display the pressure waveforms from each sensor. The user interface of the PC or PCM may allow the operator to input user data such as patient identification, and data interfaces may be provided to output data to other devices or systems, or receive data from other sources, such as from other sensors or monitoring systems, which are typically used in an ICU or OR. For example, in a cardiac catheterization laboratory, the control system for a multi-sensor catheter may be coupled to, or part of, a computing system controlling other equipment, and which is equipped with one or more large screen displays close to the operating table, and other remote displays in a monitoring area. The latter are used to display various forms of data, sequentially, concurrently, or on demand. Such data may include, e.g. fluoroscopic imaging, with or without contrast media, and transoesophageal echo-cardiography (TEE) images, as well as sensor data comprising pressure waveforms from the sensor catheter and sensor guidewire and associated hemodynamic parameters calculated or derived from the received FP optical pressure sensor data.

Figure 28A:
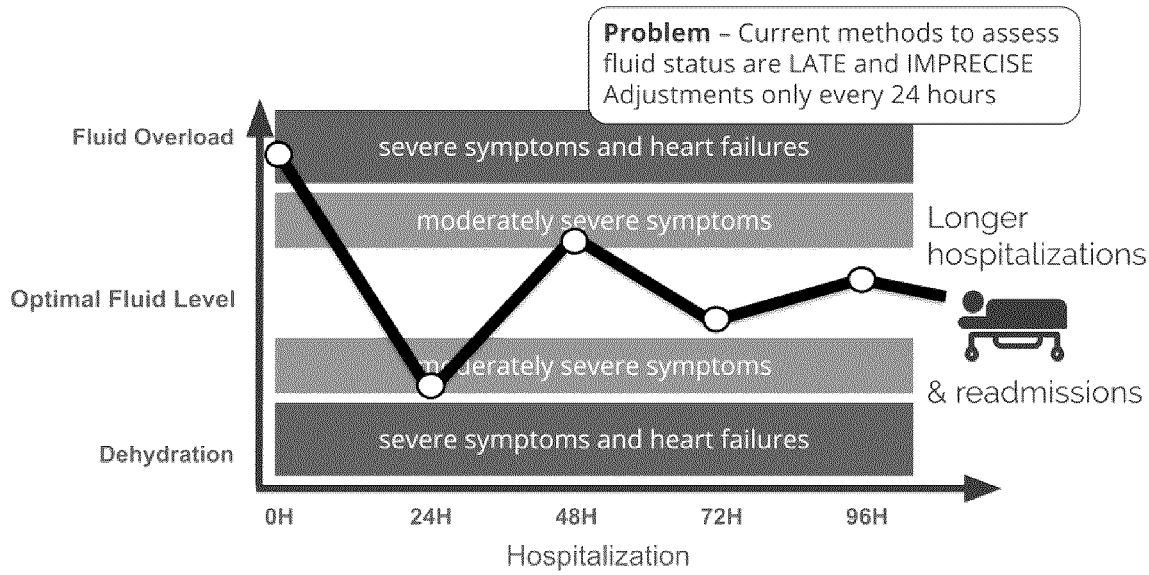
FIG. 28A and FIG. 28B are a schematic diagrams to represent a timeline for optimization of fluid levels for management of heart failure.
Figure 28B:
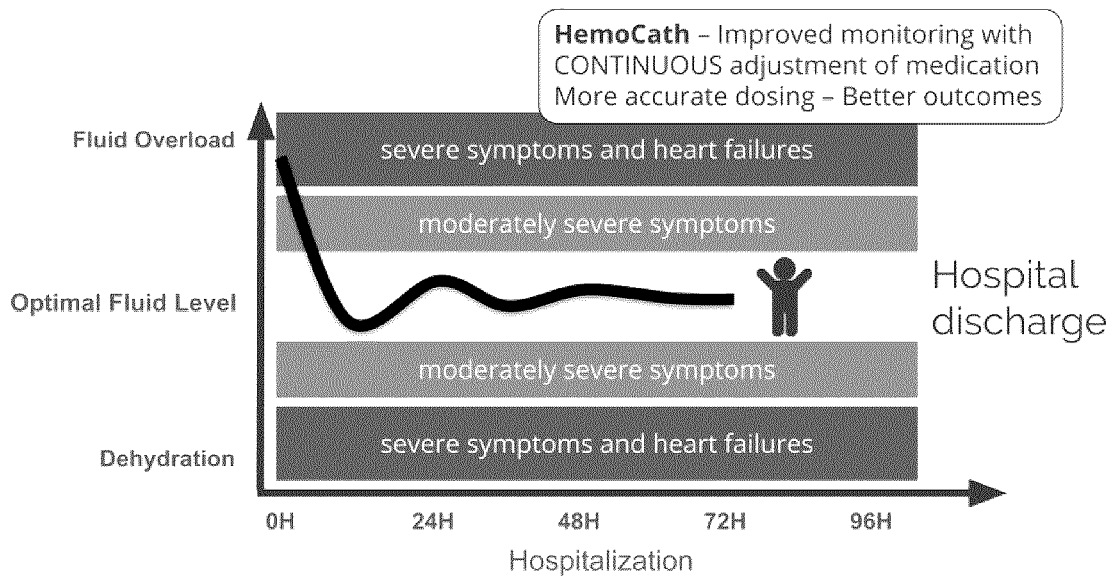

The schematic charts shown in FIGS. 28A and 28B represent comparative timelines for monitoring and management of heart failure patients using current non-invasive techniques, with adjustments to medications and treatment on a 24 hr schedule shown schematically in FIG. 28A (Prior Art), compared to use of a dual optical pressure sensor PA catheter of an embodiment that provides continual or more frequent periodic monitoring of CVP in the RA and PA pressure, which potentially enables more frequent adjustments to medications and treatments to optimize fluid levels, as shown schematically in FIG. 28B. For example, continual monitoring 24 hr day with a dual sensor PA catheter may allow for more frequent adjustment of treatments and more aggressive treatments, e.g. 12 hr adjustment in medications, instead of conventional 24 hr adjustment in medications.

A flow-directed multi-sensor catheter may be indicated for the assessment of a cardiac hemodynamic condition through direct, real-time monitoring of right atrial pressure and pulmonary artery or wedge pressure, and for infusing solutions. The distal (pulmonary artery) port also allows sampling of mixed venous blood for the assessment of oxygen transport balance and the calculation of derived parameters such as oxygen consumption, oxygen utilization coefficient, and intrapulmonary shunt fraction. Secondary indications are for sampling blood and infusing solutions.

Some embodiments of a dual optical pressure sensor PA catheter (HemoCath™) disclosed herein comprise a flow-directed multi-sensor right heart catheter for directly and concurrently monitoring of pulmonary artery pressure and central venous pressure, which is intended for use on critical care patients. The multi-sensor PA catheter has an outside diameter enabling insertion into the heart through a vein in the upper arm of a patient, or other peripheral veins. Two optical pressure sensors are integrated within the distal end portion of the PA catheter. The pressure sensor locations are configured to position the first pressure sensor in the pulmonary artery and the second pressure sensor in the right atrium during right heart and pulmonary artery catheterization, for blood pressure measurements concurrently at each sensor location. The catheter includes an inflatable balloon at the tip which facilitates its placement into the pulmonary artery through the flow of blood. A cable and connector at the proximal end of the PA catheter are used for connection to a control module (HemoLink™) The control module is to be interfaced with a compatible patient care monitor for monitoring blood pressure waveforms from each optical pressure sensor on a graphical user interface.

Dual Pressure Sensor Catheter and Control System Configured for Monitoring of Effectiveness of a Cardiac Shunt for Treatment of Heart Failure.

Figure 29:
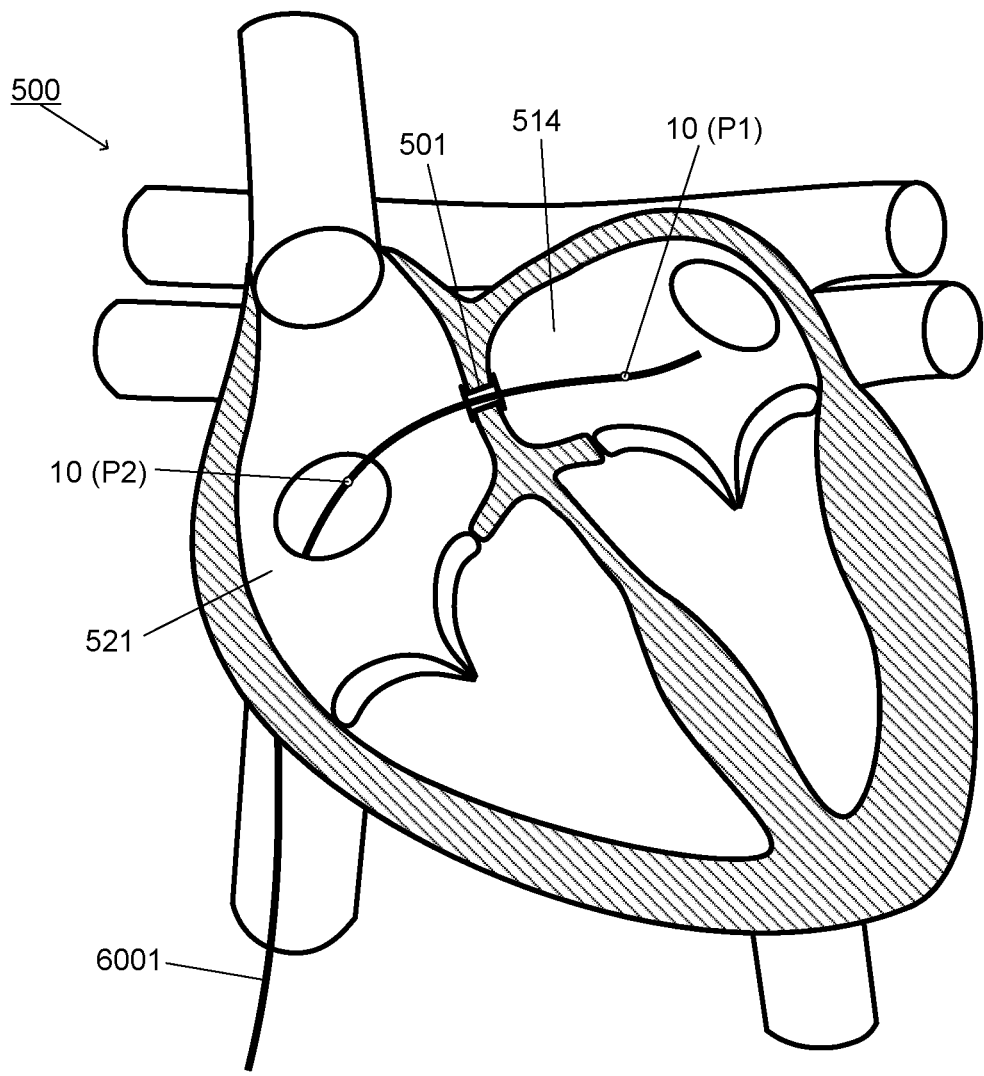
FIG. 29 shows a schematic partial cross-sectional diagram of a heart, in which an inter-atrial shunt has been inserted, and comprising a dual sensor catheter of another embodiment, which is configured for measuring pressure in the RA and CVP in the LA.

A dual sensor catheter 6001 of another embodiment is shown in FIG. 29. In this embodiment, the dual sensor catheter is configured for monitoring blood pressure upstream and downstream of an inter-atrial shunt, which is inserted in the wall between the right and left atria. The dual sensor catheter is configured for concurrent measurement of blood pressure in the LA and CVP in the RA, e.g. for monitoring of these pressures when an inter-atrial shunt 501 has been inserted between the RA and LA to reduce pressure in the LA, for treatment of heart failure. That is, an increase in pressure in the LA may occur in heart failure, and cause fluid build-up in the lungs. An inter-atrial shunt may be a small opening created in the heart wall (septum) or it may be a prosthetic device which is inserted in the heart wall (septum) between the RA and LA to provide a small opening or a prosthetic valve, which allows for a small amount of blood flow from the LA to the RA to reduce pressure in the LA, as described, for example in an article entitled: "Transcatheter Interatrial Shunt Device for Treatment of Heart Failure with Preserved Ejection Fraction" Circulation 2018: 137; pp. 364-375 Jan. 23, 2018. An inter-atrial shunt may be inserted into the heart over a guidewire, using a minimally invasive transcatheter procedure, e.g. by introduction through a femoral vein. In this scenario, there is a need for interventional cardiologists to be able to directly measure pressures in the LA and RA to monitor effectiveness of the inter-atrial shunt. The dual sensor catheter of this embodiment comprises first and second optical pressure sensors P1 and P2, wherein P1 is located near the tip of the catheter for measuring the LA pressure, and P2 is located a distance away from P1, to place P2 in the RA for measuring CVP. The spacing between pressure sensors P1 and P2 is selected to match dimensions of the heart which is being monitored, e.g. ~10 cm for an adult heart. A smaller P1 to P2 spacing and outside diameter may be required for paediatric patients.

An inter-atrial shunt may have an opening or valve having a diameter of a few millimeters, e.g. 8 mm. A dual pressure sensor with an outside diameter of 5 French or less, e.g. 4 French (0.45 mm), is suitable for monitoring of RA and LA pressures without significantly interfering with operation of the inter-atrial shunt (e.g. similar to the outside diameter of dual sensor catheter described with reference to FIGS. 17, 18A and 18B). However, in the dual sensor catheter for monitoring of an inter-atrial shunt, the first and second pressure sensors are spaced apart by an appropriate distance for directly monitoring pressures in the RA and LA, as shown schematically in FIG. 29. The spacing between pressure sensors P1 and P2 depends on the size of the heart, and may be, e.g. ~10 cm. The dual sensor catheter configured for monitoring of an inter-atrial shunt is inserted into the heart using a small diameter guidewire, and does not require an inflatable balloon, so a balloon and balloon inflation port are omitted This dual sensor catheter can be operated with a control system similar to that described above with reference to the dual pressure sensor PA catheter of the third embodiment.

Variants of the multi-sensor catheter of this embodiment for monitoring heart failure may be used to measure the blood pressure in the left atrium and other neighbouring blood vessels. In some instances, a cardiac shunt is inserted between the LA and a coronary sinus adjacent the LA, and the spacing of the pressure sensors P1 and P2 of a dual sensor catheter is selected to provide concurrent blood pressure measurements in the LA and the coronary sinus. The coronary sinus is a blood vessel that collects blood from the coronary veins of the heart and drains into the RA. Thus, the LA and RA are connected through the coronary sinus. A multi-sensor catheter having a third optical pressure sensor may be provided to enable concurrent measurement of blood pressures within the LA, coronary sinus and RA. That is, the distal region of the catheter containing the three optical pressure sensors is configured to allow for placement of one optical pressure sensor location in each of the LA, coronary sinus, and RA.

OTHER EMBODIMENTS

By way of example, some embodiments of catheters comprising multiple optical pressure sensors for cardiac catheterization have been described in detail above. Other modifications of these embodiments of a catheter comprising two or more optical pressure sensors may be provided. For example, optionally, additional sensors may be provided, e.g. a thermo-dilution sensor for measurement of blood flow, and/or an oximeter for measurement of oxygen saturation. Additional lumens to accommodate these sensors, and additional optical and electric connections of the sensors to the controller would then be required. For some applications, it may be desirable for some applications to include these additional sensors. However, there is a trade-off with respect to the outside diameter of the PA catheter required to accommodate more sensors, the complexity of the control system for additional sensor, and cost. Since a multi-sensor catheter is a single use, disposable device, a version with two optical pressure sensors, e.g. configured as illustrated schematically in FIGS. 17 and 19, allows for use of a multi-sensor catheter with a smaller outside diameter and a simplified, lower cost control system, which enables measurement of CVP in the RA, and PA pressure and PCWP in the PA, for monitoring of hemodynamic parameters, e.g. for monitoring of heart failure over a period of hours, days or months, using a small diameter catheter, e.g. ≤4 French. Restriction of the system to two optical pressure sensors (i.e. a dual pressure sensor catheter) simplifies the control system, e.g. to allow for miniaturization of the control system in the form of a portable or wearable unit. Beneficially, an optical fiber for oximetry, i.e. for measuring blood oxygen saturation, provides additional data for monitoring heart failure.

TABLE 2

| Abbreviations or acronyms | |
|---|---|
| ARi or AR Index | Aortic Regurgitation Index |

TABLE 2-continued

| Abbreviations or acronyms | |
|---|---|
| Cath Lab | Cardiac Catheterization Laboratory |
| CO | Cardiac Output |
| CVP | Central Venous Pressure |
| DBP | Diastolic Blood Pressure |
| FP MOMS Sensor | Fabry-Pérot Micro-Opto-Mechanical-System Sensor |
| ICU | Intensive Care Unit |
| LAP | Left Atrial Pressure |
| LVEDP | Left Ventricular End-Diastolic Pressure |
| OR | Operating Room |
| PA | Pulmonary Artery |
| PCM | Patient Care Monitor |
| PCWP | Pulmonary Capillary Wedge Pressure |
| PEBA | PolyEther Block Amide |
| RA | Right Atrium |
| RHC | Right Heart Catheterization |
| RV | Right Ventricle |
| $SvO_2$ | Mixed venous oxygen saturation |
| SBP | Systolic Blood Pressure |
| TAVI or TAVR | Transcatheter Aortic Valve Implantation or Replacement |
| TMVI or TMVR | Transcatheter Mitral Valve Implantation or Replacement |
| TPE | Thermoplastic elastomer |
| TVR | Transcatheter heart Valve Replacement |
| TVT | Transcatheter Valve Therapies |

Multi-sensor PA catheters according to some embodiments disclosed herein provide real-time, concurrent, multi-chamber (e.g. RA and RV) pressure measurements within the right heart and also in the PA. Each pressure measurement is taken concurrently under identical and stable conditions, while the multi-sensor catheter is positioned to locate one sensor in each of the RA, RV and PA.

In contrast, during RHC using a conventional PA catheter, it is necessary to move the catheter to get each pressure measurement, so each measurement is taken at a different time, under different conditions. For example, withdrawing a PA catheter from the PA to the RV may cause cardiac arrythmia or premature ventricular contraction (PVC). That is, the instantaneous condition for each pressure measurement is impacted by moving the catheter.

In some instances, such as monitoring in an ICU, it may be too risky to move the PA catheter once the catheter tip is placed in the PA. For a conventional PA catheter, it would then only provide the PA pressure, not a RV and RA pressure. Thus, where appropriate, the multi-sensor catheter offers continuous real-time and concurrent monitoring of all of RA, RV and PA pressures for an extended time, e.g. over a period of days, for an ICU patient. In this scenario, RA pressure monitoring provides alternative to monitoring of central venous pressure (CVP).

For post-operative monitoring, there may be risks in use of a Swan Ganz catheter, and there is a need to appropriately select patients who need Swan Ganz catheterization. For patients where Swan Ganz catheterization is appropriate, the multi-sensor PA catheter offers continuous real-time and concurrent monitoring of all of RA, RV and PA pressures.

Since these pressure measurements also provide an indirect measure of left heart hemodynamic parameters, these measurements can help to identify pathology and physiological problems and select appropriate therapies, drugs, and procedures. For example, pressure measurements may help to differentiate patient physiologies, and identify a filling problem vs. a valve problem, such as, an obstruction of the tricuspid valve.

For example, multiple concurrent blood pressure measurements during RHC may show, e.g., a high RA pressure and a low RV pressure, which may indicate tricuspid valve stenosis/obstruction. In conditions such as pulmonary edema, concurrent pressure measurements of the RA, RV, PA and PCWP may provide information which helps to determine or differentiate, e.g., whether is symptoms are caused by a RH or LH problem, a valve problem (stenosis or regurgitation), a muscle problem, cardiac restriction or constriction, PA hypertension, or a primary lung problem (such as Acute Respiratory Distress Syndrome).

In some embodiments, a flow-directed dual pressure sensor PA catheter is configured for directly monitoring blood pressures in the RA and PA, and optionally oxygen levels in the PA, to provide a cardiologist with additional data, based on continual or more frequent monitoring of these parameters, e.g. for patients with heart failure.

In other embodiments, systems and apparatus comprising a dual pressure sensor or multi-sensor catheter are disclosed, that allow for assessment of a cardiac hemodynamic condition, e.g. after a cardiac shunt has been created or inserted for treatment of heart failure, by direct measurement of blood pressures upstream and downstream of the cardiac shunt.

Although embodiments of the invention have been described and illustrated in detail, it is to be clearly understood that the same is by way of illustration and example only and not to be taken by way of limitation, the scope of the present invention being limited only by the appended claims.

The invention claimed is:

1. A flow-directed multi-sensor catheter for right heart and pulmonary artery catheterization configured for assessment of a cardiac hemodynamic condition, through direct monitoring of a right atrial pressure and a pulmonary artery pressure, comprising:
   a length of multi-lumen catheter tubing comprising a plurality of lumens extending between a proximal end and a distal end comprising an atraumatic distal tip;
   one of the lumens being a guidewire lumen having a proximal port and an opening at the distal tip of the catheter tubing,
   an inflatable balloon near the distal tip, and one of the lumens being a balloon inflation lumen, the inflatable balloon being coupled by the balloon inflation lumen to a balloon inflation port at the proximal end of the catheter tubing;
   a plurality of optical sensors and a plurality of optical fibers;
   a sensor end of each optical fiber being attached and optically coupled to an individual one of the plurality of optical sensors;
   each optical sensor and its optical fiber being inserted into a respective lumen of the multi-lumen catheter tubing;
   a proximal end of each of the plurality of optical fibers being coupled to an optical input/output connector at the proximal end of the catheter for connection to an optical control system; and
   the plurality of optical sensors forming a sensor arrangement comprising first and second optical pressure sensors at respective sensor locations spaced apart lengthwise within a distal end portion of the catheter tubing, with an aperture in the catheter tubing adjacent each optical pressure sensor for fluid contact; and
   wherein said pressure sensor locations are configured to position the first pressure sensor in the pulmonary artery and the second pressure sensor in the right atrium during right heart and pulmonary artery catheterization, for concurrent blood pressure measurements at each optical pressure sensor location.

2. A multi-sensor catheter configured for monitoring of a cardiac shunt, through direct monitoring of blood pressures upstream and downstream of the cardiac shunt, comprising:
   a length of multi-lumen catheter tubing comprising a plurality of lumens extending between a proximal end and a distal end comprising an atraumatic distal tip;
   one of the lumens being a guidewire lumen having a proximal port and an opening at the distal tip of the catheter tubing,
   an inflatable balloon near the distal tip, and one of the lumens being a balloon inflation lumen, the inflatable balloon being coupled by the balloon inflation lumen to a balloon inflation port at the proximal end of the catheter tubing;
   a plurality of optical sensors and a plurality of optical fibers;
   a sensor end of each optical fiber being attached and optically coupled to an individual one of the plurality of optical sensors;
   each optical sensor and its optical fiber being inserted into a respective lumen of the multi-lumen catheter tubing;
   a proximal end of each of the plurality of optical fibers being coupled to an optical input/output connector at the proximal end of the catheter for connection to an optical control system; and
   the plurality of optical sensors forming a sensor arrangement comprising first and second optical pressure sensors at respective sensor locations spaced apart lengthwise within a distal end portion of the catheter tubing, with an aperture in the catheter tubing adjacent each optical pressure sensor for fluid contact; and
   wherein the pressure sensor locations are configured to place the first pressure sensor in the left atrium (LA) for monitoring of LA pressure and to place the second pressure sensor downstream of the cardiac shunt, for concurrent blood pressure measurements at each optical pressure sensor location.

3. The multi-sensor catheter of claim 2, wherein the multi-sensor catheter is configured for monitoring of an inter-atrial cardiac shunt between the LA and the right atrium (RA) and the pressure sensor locations are configured to place the first pressure sensor in the LA for monitoring of LA pressure and the second pressure sensor in the RA for monitoring of central venous pressure (CVP).

4. The multi-sensor catheter of claim 2, wherein the multi-sensor catheter is configured for monitoring of a cardiac shunt between the LA and a coronary sinus, and the pressure sensor locations are configured to place the first pressure sensor in the LA for monitoring of LA pressure and the second pressure sensor in the coronary sinus.

5. The multi-sensor catheter of claim 4, wherein the optical sensors comprise a third optical pressure sensor, and the first, second and third optical pressure sensor locations are configured for concurrent measurements of blood pressure in the LA, and downstream of the cardiac shunt in the coronary sinus and in the RA.

6. A multi-sensor catheter system comprising:
   a multi-sensor catheter as defined in claim 1; and
   a control system comprising:
      a light source and detector, and an optical interface for coupling, via respective input/output ports, to each of the optical fibers and optical sensors of the multi-sensor catheter; data storage and processing means configured for processing optical data indicative of pressure values received from each of the optical pressure sensors.

7. The multi-sensor catheter system of claim 6, wherein the data storage and processing means is configured for processing optical data indicative blood oxygen levels received from an optical oximeter of the multisensory catheter.

8. The multi-sensor catheter system of claim 6, comprising:
   a circuit emulating two BP-22 outputs for each optical pressure sensor, which converts digital outputs from each optical pressure sensor for direct communication with a BP-22 compliant patient care monitor (PCM).

9. The multi-sensor catheter system of claim 6, comprising a portable unit having a communications interface for remote patient monitoring.

10. The multi-sensor catheter system of claim 6, comprising a wearable unit having a communications interface for remote patient monitoring.

11. The multisensor catheter of claim 1 wherein the guidewire lumen has a circular cross-section and other lumens have an oval cross-section.

12. The multisensor catheter of claim 1 wherein at least one of the lumens has an oval cross-section.

13. The multisensor catheter of claim 1 wherein each of the lumens has an oval cross-section.

* * * * *